United States Patent
Dupont-Passelaigue et al.

(10) Patent No.: US 8,946,225 B2
(45) Date of Patent: Feb. 3, 2015

(54) DERIVATIVES OF 2H PYRIDAZIN-3-ONES, THEIR PREPARATION AND THEIR USE AS SCD-1 INHIBITORS

(75) Inventors: Elisabeth Dupont-Passelaigue, Castres (FR); Samuel Mialhe, Castres (FR); Jean-Pierre Rieu, Castres (FR); Didier Junquero, Castres (FR); Karine Valeille, Palaiseau (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 42 days.

(21) Appl. No.: 13/388,884

(22) PCT Filed: Aug. 5, 2010

(86) PCT No.: PCT/EP2010/061426
§ 371 (c)(1),
(2), (4) Date: Feb. 3, 2012

(87) PCT Pub. No.: WO2011/015629
PCT Pub. Date: Feb. 10, 2011

(65) Prior Publication Data
US 2012/0178678 A1    Jul. 12, 2012

(30) Foreign Application Priority Data
Aug. 5, 2009   (FR) ...................... 09 55504

(51) Int. Cl.
*A61K 31/50*   (2006.01)
*A61K 31/501*   (2006.01)
*C07D 237/02*   (2006.01)

(52) U.S. Cl.
USPC ...................... 514/252.01; 544/224

(58) Field of Classification Search
USPC ...................... 544/224; 514/252.01
See application file for complete search history.

(56) References Cited

U.S. PATENT DOCUMENTS

| | | |
|---|---|---|
| 2008/0280916 A1 | 11/2008 | Bilich et al. |
| 2009/0155187 A1* | 6/2009 | Nishiyama et al. ............ 424/45 |
| 2009/0325956 A1 | 12/2009 | Taniguchi et al. |

FOREIGN PATENT DOCUMENTS

| | | |
|---|---|---|
| WO | WO 2008/044767 A1 | 4/2008 |
| WO | WO 2009/019566 A1 | 2/2009 |

OTHER PUBLICATIONS

International Search Report for PCT/EP2010/061426 dated Sep. 1, 2010.
Attie et al., "Relationship between stearoyl-CoA desaturase activity and plasma triglycerides in human and mouse hypertriglyceridema", Journal of Lipid Research, vol. 43 (2002) pp. 1899-1907.
Biddinger et al., "Leptin Suppresses Stearoyl-CoA Desaturase 1 by Mechanisms independent of Insulin and Sterol Regulatory Element-Binding Protein-1c", Diabetes, vol. 55 (2006) pp. 2032-2041.
Cohen et al., "Role for Stearoyl-CoA Desaturase-1 in Leptin-Mediated Weight Loss", Science, vol. 297 (2002) pp. 240-243.
Gomez et al., "Effects of steroulic acid on stearoyl-CoA desaturase in differentiating 3T3-L1 adipocytes", Biochemical and Biophysical Research Communications, vol. 300 (2003) pp. 316-326.
Grundy, "Drug therapy of the metabolic syndrome: minimizing the emerging crisis in polypharmacy", Nature Reviews Drug Discovery, vol. 5 (2006) pp. 295-309.
Hulver et al., "Elevated stearoyl-CoA desaturase-1 expression in skeletal muscle contributes to abnormal fatty acid partitioning in obese humans", Cell Metabolism, vol. 2 (2005) pp. 251-261.
Miyazaki et al., "A lipogenic diet in mice with a disruption of the stearoyl-CoA desaturase 1 gene reveals a stringent requirement of endogenous monounsaturated fatty acids for triglyceride synthesis", Journal of Lipid Research, vol. 42 (2001) pp. 1018-1024.
Ntambi et al., "Loss of stearoyl-CoA desaturase-1 function protects mice against adiposity", PNAS, vol. 99, No. 17 (2002) pp. 11482-11486.
Okada et al., "Plasma palmitoleic acid content and obesity in children", Am. J. Clin. Nutr., vol. 82 (2005) pp. 757-750.

* cited by examiner

*Primary Examiner* — Paul V. Ward
(74) *Attorney, Agent, or Firm* — Birch, Stewart, Kolasch & Birch, LLP

(57) ABSTRACT

The present invention concerns compounds of general formula (I) characterized in that (formula 1) wherein, in particular: —$R_1$ represents one or more groups such as: trifluoromethyl, halogen such as F, Cl, —when n=m=1, W represents CH then Y represents oxygen, —U represents: •either —(C═O)CH$_2$NH— and is branched at position 4 of pyridazinone, then R2 represents H, •or —(C═O)NH— and U is branched at positions (4), (5) or (6) of pyridazinone, then R2 represents H, —R3 represents a hydrogen or methyl and the addition salts with pharmaceutically acceptable bases and acids and the different isomers, and their mixtures in any proportion for use as SCD-1 enzyme inhibitors for the treatment of obesity, type-2 diabetes and lipid disorders.

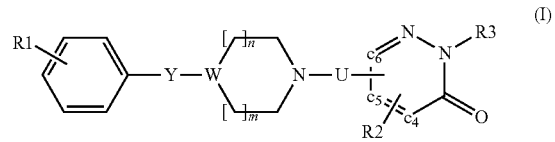

18 Claims, No Drawings

DERIVATIVES OF 2H PYRIDAZIN-3-ONES, THEIR PREPARATION AND THEIR USE AS SCD-1 INHIBITORS

The subject of the present invention concerns derivatives of 2H pyridazin-3-one inhibiting the activity of the SCD-1 enzyme, and their application in human therapy.

Metabolic syndrome results from increased peripheral resistance to insulin, and is characterized by obesity, intolerance to glucose, certain dyslipidaemias which may be associated with high blood pressure and with vascular inflammation. The combination of these multiple risk factors promotes the development of atheromatous pathology, the cause of thrombotic attacks and the development of coronary, cerebrovascular and peripheral arterial diseases (Grundy, S. M. Drug therapy of the metabolic syndrome: minimizing the emerging crisis in polypharmacy. *Nat Rev Drug Discov* 5, 295-309 (2006)).

Stearoyl-CoA Desaturase-1 (SCD-1), also called Δ9-desaturase, is an enzyme limiting the synthesis of mono-unsaturated fatty acids under the control of the transcription factor $SREBP_{1C}$ (Miyazaki, M., Kim, Y. C., Ntambi, J. M. A lipogenic diet in mice with a disruption of the stearoyl-CoA desaturase-1 gene reveals a stringent requirement of endogenous monounsaturated fatty acids for triglyceride synthesis. *J Lipid Res* 42, 1018-1024 (2001)). Disablement of the SCD-1 gene in mice imparts resistance to genetic or diet-induced obesity; the peripheral effects of leptin on the increase in energy expenditure, weight loss and insulin sensitivity are inversely correlated with the expression of the SCD-1 gene and with enzymatic activity (Cohen, P., Miyazaki, M., Socci, N. D. et al. Role for stearoyl-CoA desaturase-1 in leptin-mediated weight loss. *Science* 297, 240-243 (2002), Ntambi, J. M., Miyazaki, M., Stoehr, J. P. et al. Loss of stearoyl-CoA desaturase-1 function protects mice against adiposity. *Proc Natl Acad Sci* 99, 11482-11486 (2002), Biddinger, S. B., Miyazaki, M., Boucher, J. et al. Leptin suppresses stearoyl-CoA desaturase-1 by mechanisms independent of insulin and sterol regulatory element-binding protein-1c. *Diabetes* 55, 2032-2041 (2006)).

The involvement of SCD-1 in the pathogenesis of obesity is reinforced by the correlation between the plasma concentration of palmitoleic acid and abdominal adiposity in children (Okada, T., Furuhashi, N., Kuromori, Y. et al. Plasma palmitoleic acid content and obesity in children. *Am J Clin Nutr* 82, 747-750 (2005)), the association of SCD-1 overexpression in the skeletal muscles of obese adults with poor partitioning of fatty acids leading to inhibition of hepatic β-oxidation (Hulver, M. W., Berggren, J. R., Carper, M. J. et al. Elevated stearoyl-CoA desaturase-1 expression in skeletal muscle contributes to abnormal fatty acid partitioning in obese humans. *Cell Metab* 2, 251-261 (2005)). The plasma ratio 18:1/18:0, also called "desaturation index", appears to be the biomarker of SCD-1 activity in man and correlates with the plasma triglyceride level and in inverse proportional manner with the HDL level (Attie, A. D., Krauss, R. M., Gray-Keller, M. P. et al. Relationship between stearoyl-CoA desaturase activity and plasma triglycerides in human and mouse hypertriglyceridemia. *J Lipid Res* 43, 1899-1907 (2002)).

The treatment of lipid disorders in dermatology such as acne, rosacea or hyperseborrhea has also recently been claimed for SCD-1 inhibitors (US2008280916) and the inhibition of sebum production (WO2009019566).

Consequently, SCD-1 inhibition appears to be a choice therapeutic target for the treatment of obesity, Type-2 diabetes and lipid disorders related to metabolic syndrome, and in dermatology for lipid disorders of the skin.

The present invention concerns novel derivatives of 2H pyridazin-3-one inhibiting the activity of the SCD-1 enzyme, their preparation and their application in human therapy.

These compounds meet general formula I:

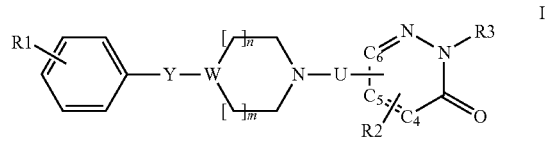

in which
$R_1$ represents one or more groups such as: trifluoromethyl, halogen such as F, Cl, Br, $C_1$-$C_4$ alkyl straight or branched, nitro, trifluoromethoxy, acetyl.
when n=m=1,
  W represents CH, then Y is oxygen or —$CH_2N(CH_3)$— or —$NHCH_2$—.
  or W represents nitrogen, then Y is C=O.
when n=m=0, W represents CH, then Y is O or —$OCH_2$—.
when n=1 and m=0, W represents CH, then Y is —$OCH_2$—.
U represents
  either —(C=O)$CH_2$O— and can be branched at position (4) or (5) of pyridazinone and R2 is hydrogen,
  or —(C=O)$CHR_4NR_5$— in which $R_4$=$R_5$=H or independently of each other can be equal to H or Me, and if U is branched at position (4) of pyridazinone then R2 is at position (5) and represents H or OMe, and if U is branched at position (5) of pyridazinone then R2 represents H.
  or —(C=O)NH— and can be branched at position (4) or (5) or (6) of pyridazinone and R2 represents H,
  or —(C=O)(C=O)NH—, —(C=O)CH=CH—, —(C=O)$CH_2CH_2$—, and can be branched at position (4) of pyridazinone, then R2 represents H,
$R_3$ represents:
  a hydrogen or
  a $C_1$-$C_6$ straight or branched alkyl radical, or a $C_1$-$C_3$ alkyl radical substituted by groups such as: trifluoromethyl, phenyl, or a $C_3$ alkynyl.

According to another embodiment of the invention, the compounds of general formula (I) are those in which:

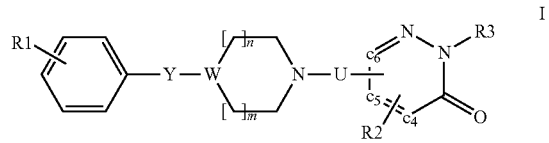

$R_1$ represents one or more groups such as: trifluoromethyl, halogen such as F, Cl, Br, $C_1$-$C_3$ alkyl straight or branched, trifluoromethoxy,
when n=m=1,
  W represents CH then Y is oxygen or —$CH_2N(CH_3)$— or W represents nitrogen, then Y represents C=O.
when n=m=0, W represents CH, then Y is —$OCH_2$—.
U represents:
  either —(C=O)$CH_2NH$— and if U is branched at position (4) of pyridazinone then $R_2$ is at position (5) and represents H or OMe, and if U is branched at position (5) of pyridazinone then $R_2$ is at position 4 and represents H or —(C=O)NH— and U can be branched at positions (4), (5) or (6) of pyridazinone, then R₂ represents H,
or —(C=O)(C=O)NH—, —(C=O)CH=CH—, —(C=O)CH₂CH₂—, and U is branched at position (4) of pyridazinone, then R2 represents H,
R₃ represents:
a hydrogen or
a C₁-C₄ straight or branched alkyl radical, and more particularly methyl, According to another embodiment of the invention, the compounds of general formula (I) are those in which:

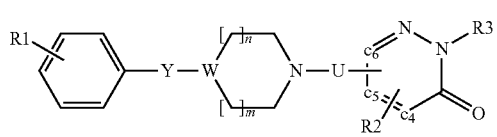

R₁ represents one or more groups such as: trifluoromethyl, halogen such as F, Cl,
n=m=1, W represents CH then Y is oxygen,
U represents
either —(C=O)CH₂NH— and is branched at position 4 of pyridazinone, then R2 represents H,
or —(C=O)NH— and U can be branched at positions (4), (5) or (6) of pyridazinone, then R₂ represents H,
R₃ represents a hydrogen or methyl According to another embodiment of the invention, the compounds of general formula (I) are those in which:

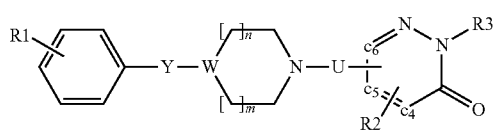

R₁ represents one or more groups such as: trifluoromethyl, halogen such as F, Cl,
when n=m=1, W represents CH then Y is oxygen,
U represents —(C=O)CH₂NH— and is branched at position 4 of pyridazinone then R2 represents H,
R₃ represents a hydrogen or methyl
and the addition salts with the pharmaceutically acceptable bases and acids and the different isomers, and their mixtures in any proportion.

The present invention concerns the compounds of general formula I characterized in that they are chosen from among:
1: 2-Methyl-4-{2-oxo-2-[4-(2-trifluoromethyl-phenoxy)-piperidin-1-yl]-ethylamino-2H-pyridazin-3-one
2: 4-{2-[4-(5-Fluoro-2-trifluoromethyl-phenoxy)-piperidin-1-yl]-2-oxo-ethylamino}-2-methyl-2H-pyridazin-3-one
3: 4-{2-[4-(3-Fluoro-5-trifluoromethyl-phenoxy)-piperidin-1-yl]-2-oxo-ethylamino}-2-methyl-2H-pyridazin-3-one
4: 4-{2-[4-(2-Chloro-5-trifluoromethyl-phenoxy)-piperidin-1-yl]-2-oxo-ethylamino}-2-methyl-2H-pyridazin-3-one
5: 4-{2-[4-(2-Bromo-4,5-difluoro-phenoxy)-piperidin-1-yl]-2-oxo-ethylamino}-2-methyl-2H-pyridazin-3-one
6: 4-{2-[4-(5-Bromo-2-chloro-phenoxy)-piperidin-1-yl]-2-oxo-ethylamino}-2-methyl-2H-pyridazin-3-one
7: 4-{2-[4-(2-Chloro-phenoxy)-piperidin-1-yl]-2-oxo-ethylamino}-2-methyl-2H-pyridazin-3-one
8: 4-{2-[4-(2-Chloro-5-fluoro-phenoxy)-piperidin-1-yl]-2-oxo-ethylamino}-2-methyl-2H-pyridazin-3-one
9: 4-{2-[4-(2-Chloro-5-nitro-phenoxy)-piperidin-1-yl]-2-oxo-ethylamino}-2-methyl-2H-pyridazin-3-one
10: 4-{2-[4-(3,4-Dichloro-phenoxy)-piperidin-1-yl]-2-oxo-ethylamino}-2-methyl-2H-pyridazin-3-one
11: 4-{2-[4-(2,4-Dichloro-phenoxy)-piperidin-1-yl]-2-oxo-ethylamino}-2-methyl-2H-pyridazin-3-one
12: 4-{2-[4-(2,5-Dichloro-phenoxy)-piperidin-1-yl]-2-oxo-ethylamino}-2-methyl-2H-pyridazin-3-one
13: 4-{2-[4-(5-Fluoro-2-methyl-phenoxy)-piperidin-1-yl]-2-oxo-ethylamino}-2-methyl-2H-pyridazin-3-one
14: 4-{2-[4-(5-Isopropyl-2-methyl-phenoxy)-piperidin-1-yl]-2-oxo-ethylamino}-2-methyl-2H-pyridazin-3-one
15: 4-({2-[4-(2-Chloro-phenoxy)-piperidin-1-yl]-2-oxo-ethyl}-methyl-amino)-2-methyl-2H-pyridazin-3-one
16: 5-{2-[4-(2-Chloro-5-fluoro-phenoxy)-piperidin-1-yl]-2-oxo-ethylamino}-2-methyl-2H-pyridazin-3-one
17: 5-{2-[4-(2-Chloro-5-trifluoromethyl-phenoxy)-piperidin-1-yl]-2-oxo-ethoxy}-2-methyl-2H-pyridazin-3-one
18: 5-{2-[4-(2,5-Dichloro-phenoxy)-piperidin-1-yl]-2-oxo-ethoxy}-2-methyl-2H-pyridazin-3-one
19: 2-Methyl-4-{2-oxo-2-[3-(2-trifluoromethyl-phenoxy)-azetidin-1-yl]-ethylamino}-2H-pyridazin-3-one
20: 2-Methyl-4-(2-oxo-2-{4-[(2-trifluoromethyl-phenylamino)-methyl]-piperidin-1-yl}-ethylamino)-2H-pyridazin-3-one
21: 4-(2-{4-[(2-Chloro-5-trifluoromethyl-phenylamino)-methyl]-piperidin-1-yl}-2-oxo-ethylamino)-2-methyl-2H-pyridazin-3-one
22: 4-{2-[3-(2-Chloro-5-trifluoromethyl-phenoxymethyl)-pyrrolidin-1-yl]-2-oxo-ethylamino}-2-methyl-2H-pyridazin-3-one
23: 2-[4-(2-Chloro-5-trifluoromethyl-phenoxy)-piperidin-1-yl]-N-(2-methyl-3-oxo-2,3-dihydro-pyridazin-4-yl)-2-oxo-acetamide
24: 4-{(E)-3-[4-(2-Chloro-5-trifluoromethyl-phenoxy)-piperidin-1-yl]-3-oxo-propenyl}-2-methyl-2H-pyridazin-3-one
25: 4-{3-[4-(2-Chloro-5-trifluoromethyl-phenoxy)-piperidin-1-yl]-3-oxo-propyl}-2-methyl-2H-pyridazin-3-one
26: 5-{2-[4-(2,4-Dichloro-phenoxy)-piperidin-1-yl]-2-oxo-ethoxy}-2-methyl-2H-pyridazin-3-one
27: 2-Methyl-4-{2-oxo-2-[3-(2-trifluoromethyl-phenoxy)-azetidin-1-yl]-ethylamino}-2H-pyridazin-3-one
28: 4-(2-{4-[(3,4-Dichloro-benzyl)-methyl-amino]-piperidin-1-yl}-2-oxo-ethylamino)-2-methyl-2H-pyridazin-3-one
29: 4-{2-[4-(5-Fluoro-2-trifluoromethyl-benzoyl)-piperazin-1-yl]-2-oxo-ethylamino}-2-methyl-2H-pyridazin-3-one
30: 2-Methyl-4-{2-oxo-2-[4-(2-trifluoromethyl-benzoyl)-piperazin-1-yl]-ethylamino}-2H-pyridazin-3-one
31: 2-Methyl-4-(2-oxo-2-{4-[(2-trifluoromethyl-phenylamino)-methyl]-piperidin-1-yl}-ethylamino)-2H-pyridazin-3-one
32: 4-(2-{4-[(2-Chloro-5-trifluoromethyl-phenylamino)-methyl]-piperidin-1-yl}-2-oxo-ethylamino)-2-methyl-2H-pyridazin-3-one
33: 4-{2-[3-(2-Chloro-5-trifluoromethyl-phenoxymethyl)-azetidin-1-yl]-2-oxo-ethylamino}-2-methyl-2H-pyridazin-3-one
34: 4-{2-[3-(2-Chloro-5-trifluoromethyl-phenoxymethyl)-pyrrolidin-1-yl]-2-oxo-ethylamino}-2-methyl-2H-pyridazin-3-one
35: 2-[4-(2-Chloro-5-trifluoromethyl-phenoxy)-piperidin-1-yl]-N-(2-methyl-3-oxo-2,3-dihydro-pyridazin-4-yl)-2-oxo-acetamide 36: 4-{(E)-3-[4-(2-Chloro-5-trifluoromethyl-phenoxy)-piperidin-1-yl]-3-oxo-propenyl}-2-methyl-2H-pyridazin-3-one
37: 4-{3-[4-(2-Chloro-5-trifluoromethyl-phenoxy)-piperidin-1-yl]-3-oxo-propyl}-2-methyl-2H-pyridazin-3-one
38: 4-{(R)-2-[4-(2-Chloro-5-trifluoromethyl-phenoxy)-piperidin-1-yl]-1-methyl-2-oxo-ethylamino}-2-methyl-2H-pyridazin-3-one
39: 4-{(S)-2-[4-(2-Chloro-5-trifluoromethyl-phenoxy)-piperidin-1-yl]-1-methyl-2-oxo-ethylamino}-2-methyl-2H-pyridazin-3-one
40: 4-{2-[4-(2-Chloro-5-trifluoromethyl-phenoxy)-piperidin-1-yl]-2-oxo-ethylamino}-2H-pyridazin-3-one
41: 4-{2-[4-(2,5-dichloro-phenoxy)-piperidin-1-yl]-2-oxo-ethylamino}-2H-pyridazin-3-one
42: 4-{2-[4-(5-Bromo-2-Chloro-phenoxy)-piperidin-1-yl]-2-oxo-ethylamino}-2H-pyridazin-3-one
43: 4-{2-[4-(2-Bromo-4,5-difluoro-phenoxy)-piperidin-1-yl]-2-oxo-ethylamino}-2H-pyridazin-3-one
44: 4-{2-[4-(3-trifluoromethyl-phenoxy)-piperidin-1-yl]-2-oxo-ethylamino}-2H-pyridazin-3-one
45: 4-{2-[4-(2-Chloro-5-trifluoromethyl-phenoxy)-piperidin-1-yl]-2-oxo-ethylamino}-2-(4,4,4-trifluoro-butyl)-2H-pyridazin-3-one
46: 2-But-2-ynyl-4-{2-[4-(2-chloro-5-trifluoromethyl-phenoxy)-piperidin-1-yl]-2-oxo-ethylamino}-2H-pyridazin-3-one
47: 4-{2-[4-(2-Chloro-5-trifluoromethyl-phenoxy)-piperidin-1-yl]-2-oxo-ethylamino}-2-(4-methyl-pentyl)-2H-pyridazin-3-one
48: 2-Benzyl-4-{2-oxo-2-[4-(2-trifluoromethyl-phenoxy)-piperidin-1-yl]-ethylamino}-2H-pyridazin-3-one
49: 2-Isopropyl-4-{2-oxo-2-[4-(2-trifluoromethyl-phenoxy)-piperidin-1-yl]-ethylamino}-2H-pyridazin-3-one
50: 2-Butyl-4-{2-[4-(2-chloro-phenoxy)-piperidin-1-yl]-2-oxo-ethylamino}-2H-pyridazin-3-one
51: 4-{2-[4-(2-Chloro-5-trifluoromethyl-phenoxy)-piperidin-1-yl]-2-oxo-ethylamino}-5-methoxy-2-methyl-2H-pyridazin-3-one
52: 4-(2-Chloro-5-trifluoromethyl-phenoxy)-piperidine-1-carboxylic acid (2-methyl-3-oxo-2,3-dihydro-pyridazin-4-yl)-amide
53: 4-(2-Chloro-5-fluoro-phenoxy)-piperidine-1-carboxylic acid (2-methyl-3-oxo-2,3-dihydro-pyridazin-4-yl)-amide
54: 4-(2-fluoro-5-trifluoromethyl-phenoxy)-piperidine-1-carboxylic acid (2-methyl-3-oxo-2,3-dihydro-pyridazin-4-yl)-amide
55: 4-(2,5-dimethyl-phenoxy)-piperidine-1-carboxylic acid (2-methyl-3-oxo-2,3-dihydro-pyridazin-4-yl)-amide
56: 4-(2-chloro-5-methyl-phenoxy)-piperidine-1-carboxylic acid (2-methyl-3-oxo-2,3-dihydro-pyridazin-4-yl)-amide
57: 4-(2-methyl-5-isopropyl-phenoxy)-piperidine-1-carboxylic acid (2-methyl-3-oxo-2,3-dihydro-pyridazin-4-yl)-amide
58: 4-(5-trifluoromethyl-phenoxy)-piperidine-1-carboxylic acid (2-methyl-3-oxo-2,3-dihydro-pyridazin-4-yl)-amide
59: 4-(2-methyl-phenoxy)-piperidine-1-carboxylic acid (2-methyl-3-oxo-2,3-dihydro-pyridazin-4-yl)-amide
60: 4-(4-fluoro-5-trifluoromethyl-phenoxy)-piperidine-1-carboxylic acid (2-methyl-3-oxo-2,3-dihydro-pyridazin-4-yl)-amide
61: 4-(5-fluoro-2-trifluoromethyl-phenoxy)-piperidine-1-carboxylic acid (2-methyl-3-oxo-2,3-dihydro-pyridazin-4-yl)-amide
62: 4-(2,5-dichloro-phenoxy)-piperidine-1-carboxylic acid (2-methyl-3-oxo-2,3-dihydro-pyridazin-4-yl)-amide
63: 4-(2-chloro-5-bromo-phenoxy)-piperidine-1-carboxylic acid (2-methyl-3-oxo-2,3-dihydro-pyridazin-4-yl)-amide
64: 4-(2-chloro-phenoxy)-piperidine-1-carboxylic acid (2-methyl-3-oxo-2,3-dihydro-pyridazin-4-yl)-amide
65: 4-(3,4-dichloro-phenoxy)-piperidine-1-carboxylic acid (2-methyl-3-oxo-2,3-dihydro-pyridazin-4-yl)-amide
66: 4-(2,4-dichloro-phenoxy)-piperidine-1-carboxylic acid (2-methyl-3-oxo-2,3-dihydro-pyridazin-4-yl)-amide
67: 4-(3-fluoro-5-trifluoromethyl-phenoxy)-piperidine-1-carboxylic acid (2-methyl-3-oxo-2,3-dihydro-pyridazin-4-yl)-amide
68: 4-(5-fluoro-2-methyl-phenoxy)-piperidine-1-carboxylic acid (2-methyl-3-oxo-2,3-dihydro-pyridazin-4-yl)-amide
69: 4-(2,5-difluoro-phenoxy)-piperidine-1-carboxylic acid (2-methyl-3-oxo-2,3-dihydro-pyridazin-4-yl)-amide
70: 4-(2,4,5-trichloro-phenoxy)-piperidine-1-carboxylic acid (2-methyl-3-oxo-2,3-dihydro-pyridazin-4-yl)-amide
71: 4-(2-bromo-4,5-difluoro-phenoxy)-piperidine-1-carboxylic acid (2-methyl-3-oxo-2,3-dihydro-pyridazin-4-yl)-amide
72: 4-(2-Chloro-5-trifluoromethyl-phenoxy)-piperidine-1-carboxylic acid (3-oxo-2,3-dihydro-pyridazin-4-yl)-amide
73: 4-(2-Chloro-5-trifluoromethyl-phenoxy)-piperidine-1-carboxylic acid (1-methyl-6-oxo-1,6-dihydro-pyridazin-4-yl)-amide
74: 4-(2-Chloro-5-trifluoromethyl-phenoxy)-piperidine-1-carboxylic acid (1-methyl-6-oxo-1,6-dihydro-pyridazin-3-yl)-amide.

The present invention also extends to the addition salts of the compounds of general formula (I) with the pharmaceutically acceptable bases and acids, and to the different isomers of the compounds of general formula (I) and their mixtures in any proportion.

By <<isomers>>, under the present invention, is meant the enantiomers and the isomers of cis or trans configuration.
The mixtures of the isomers in any proportion also include the racemic mixtures for the enantiomers.

The present invention also extends to the chemical methods to prepare the compounds of general formula (I).

The present invention also concerns the compounds of general formula (I) and the addition salts with the pharmaceutically acceptable bases and acids, and the different isomers, and their mixtures in any proportion for their use as inhibitor of the SCD-1 enzyme.

The present invention also concerns the compounds of general formula (I) and the addition salts with pharmaceutically acceptable bases and acids, and the different isomers, and their mixtures in any proportion, for their use and as medicinal product.

The invention also concerns the compounds of general formula (I) and the addition salts with pharmaceutically acceptable bases and acids, and the different isomers, and their mixtures in any proportion for their use as medicinal product intended for the treatment and/or prevention of diseases requiring inhibitors of the activity of the SCD-1 enzyme.

The invention also concerns the compounds of general formula (I) and their addition salts with pharmaceutically acceptable bases and acid, and the different isomers, and their mixtures in any proportion for their use as medicinal product intended for the treatment and/or prevention of diseases such as obesity, diabetic dyslipidaemia, hypertriglyceridaemia, hypercholesterolaemia, metabolic syndrome, atherosclerosis and its complications, hepatic steatosis, cardiovascular risks.

The invention also concerns the compounds of general formula (I) and their addition salts with pharmaceutically acceptable bases and acids, and the different isomers, and their mixtures in any proportion, for their use as medicinal product intended for the treatment and/or prevention of dermatological diseases related to lipid disorders of the skin, and inflammatory and microbial complications related to disturbed barrier function.

The dermatological diseases related to a lipid disorder of the skin are, for example, acne, psoriasis, hirsutism, rosacea.

The invention also extends to compositions characterized in that, as active ingredient, they contain a compound of general formula (I).

The invention also concerns a pharmaceutical composition characterized in that it contains a compound of general formula (I) in combination with any suitable excipient.

Synthesis

The compounds of the present invention can be synthesized using the synthesis routes described below or using synthesis methods known to persons skilled in the art.

Method 1

The synthesis of the compounds of general formula I is characterized (scheme 1) when U=—(C=O)CHR$_4$NR$_5$— is branched at positions (4) or (5) of pyridazinone and when R2=H in that:
a derivative of general formula II

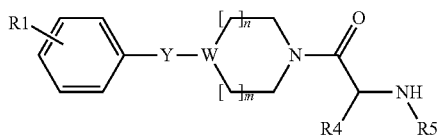

in which R$_1$ represents one or more groups: trifluoromethyl, Cl, F, C$_1$-C$_4$ alkyl straight or branched, trifluoromethoxy, acetyl, and R$_4$, and R$_5$, m, n, Y, W are such as defined in general formula I,
is condensed with a derivative of general formula III

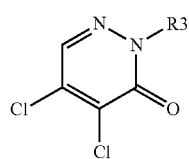

in which R$_3$ is a C$_1$-C$_6$ straight or branched alkyl radical, or a C$_1$-C$_3$ alkyl radical substituted by groups such as: trifluoromethyl, phenyl, under operating conditions such as Buchwald coupling in the presence of a catalyst such as palladium acetate, a phosphine such as BINAP and a base such as caesium carbonate in a solvent such as toluene;
the derivative of general formula IV previously obtained is dehalogenated under operating conditions such as in the presence of palladium on carbon under hydrogen in a solvent such as methanol.

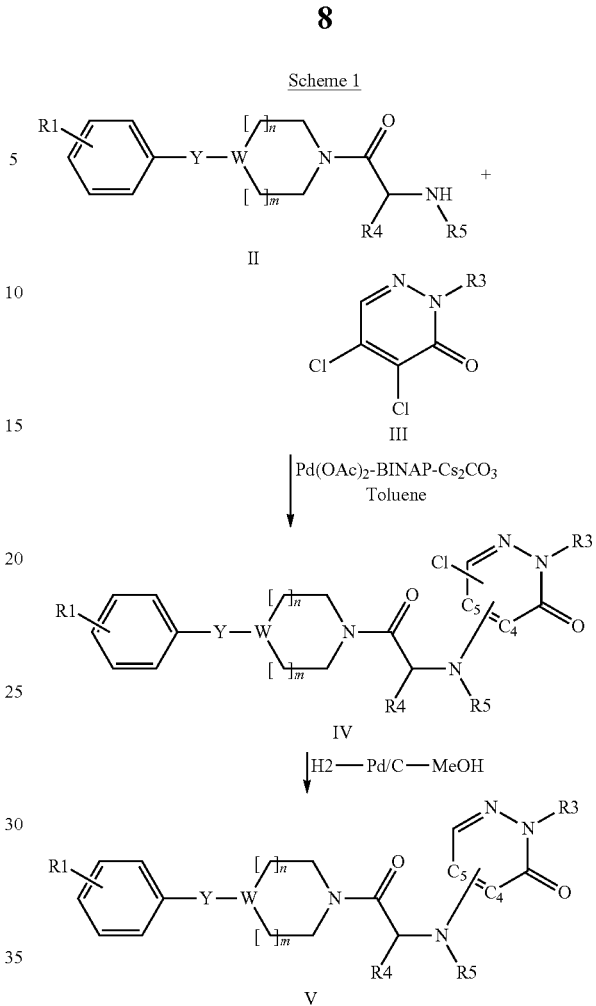

Method 2

This synthesis method of general formula I compounds is characterized (scheme 2) when U=—(C=O)CHR$_4$NR$_5$—, —(C=O)CH$_2$O—, —(C=O)(C=O)NH—, —(C=O)CH=CH—, —(C=O)(CH$_2$)$_2$— (for each definition of U the substitution positions of pyridazinone are such as defined in general formula I) in that: a derivative of general formula VI

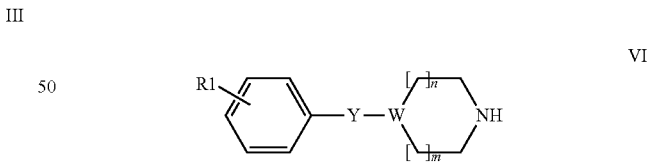

in which R$_1$, m, n, Y, W are such as defined in general formula I, is condensed with compounds of general formulas VII, IX, XIII, XV in which R$_2$, R$_4$, and R$_5$ are such as defined in general formula I, and R$_3$ represents a hydrogen or C$_1$-C$_6$ straight or branched alkyl radical, or C$_1$-C$_3$ alkyl radical substituted by groups such as: trifluoromethyl, phenyl, or compounds of general formula XI in which R$_3$ is such as defined in general formula I, under operating conditions such as those of peptide coupling with reagents such as hydroxybenzotriazole, EDCI in the presence of a base such as triethylamine in a solvent such as dichloromethane. This respectively leads to the end compounds of formula VIII, X, XIV, XVI and XII.

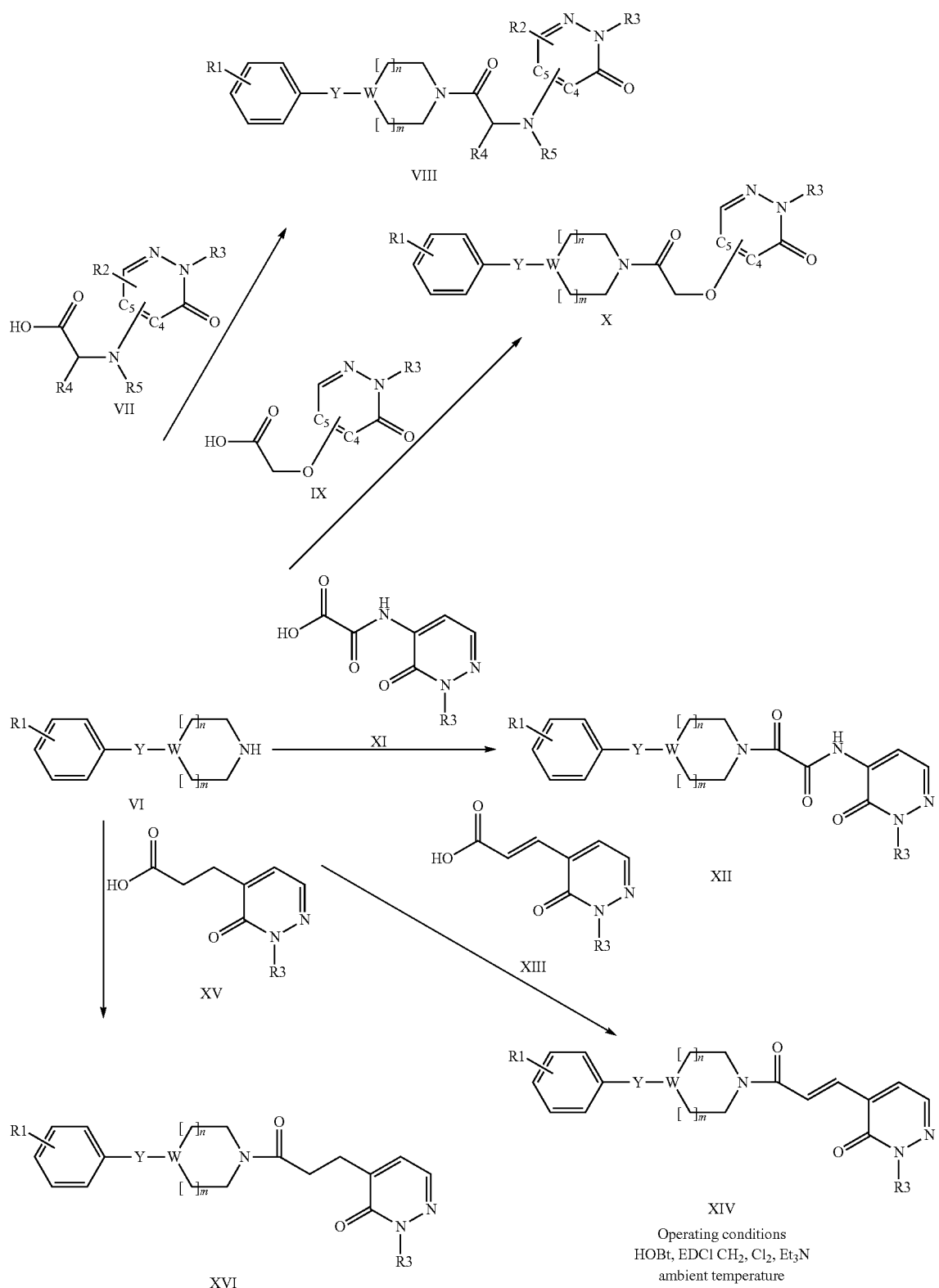
Scheme 2
Method 3
This synthesis method of general formula I compounds is characterized (scheme 3) when U=—(C=O)CHR$_4$NR$_5$— or —(C=O)CH$_2$O— (branched at positions (4) or (5) of pyridazinone) and R$_2$=H, in that derivatives of general formula

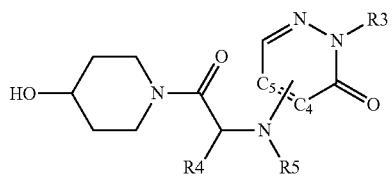

XVII

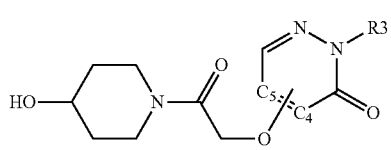

XVIII in which $R_3$ represents a $C_1$-$C_6$ straight or branched alkyl radical, or $C_1$-$C_3$ alkyl radical substituted by groups such as: trifluoromethyl or phenyl and $R_4$ and $R_5$ are such as defined in general formula I, are condensed with phenols of general formulas XIX:

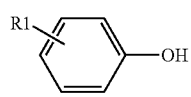

XIX in which $R_1$ is such as defined in general formula I:

Scheme 3

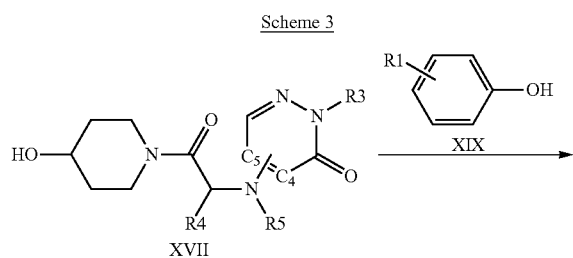

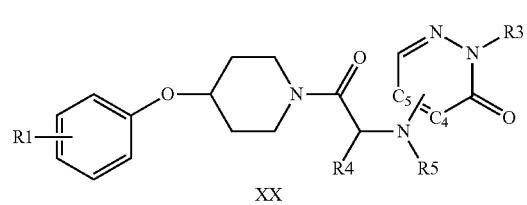

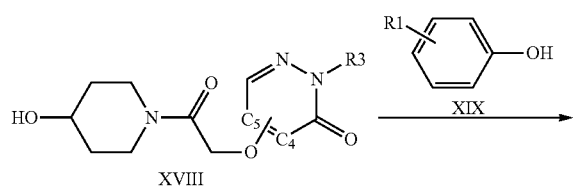

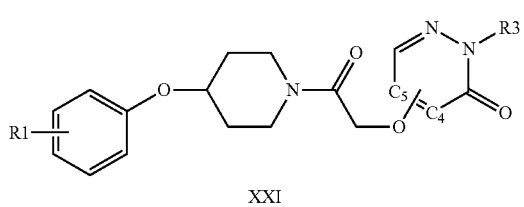

XXI under operating conditions such as those of Mitsunobu coupling in the presence of triphenylphosphine, of diisopropylazodicarboxylate in THF to arrive at the compounds XX and XXI respectively.

Method 4

This synthesis method of general formula I compounds is characterized (scheme 4) when U=—(C=O)CHR$_4$NR$_5$— is branched at position (4) of pyridazinone and $R_2$=H, in that derivatives of general formula II, in which $R_1$, $R_4$, $R_5$, n, m, Y, W are such as defined in general formula I, are condensed with compounds of general formula XXII in which $R_3$ is such as defined in general formula I, under operating conditions such as acetonitrile in the presence of triethylamine to arrive at compounds XXIII.

Scheme 4

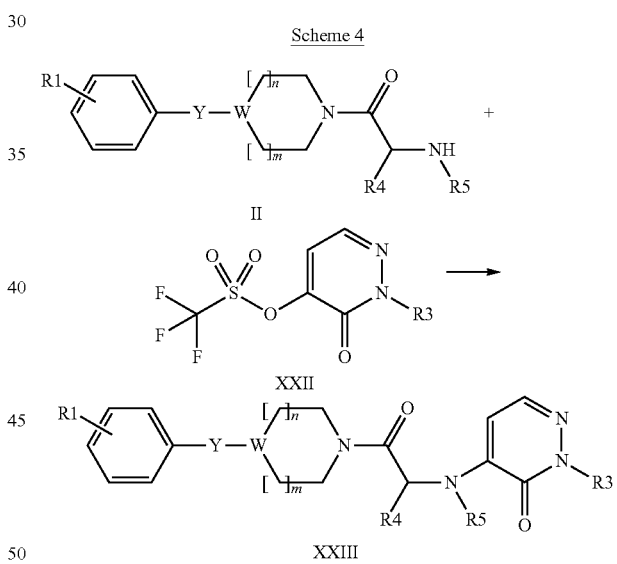

Method 5

This synthesis method of general formula I compounds is characterized (scheme 5) when U=—(C=O)CHR$_4$NR$_5$— is branched at position (4) of pyridazinone and $R_2$=H, in that the derivatives of general formula II, in which $R_1$, $R_4$, $R_5$, n, m, Y, W are such as defined in general formula I, are condensed with compounds of general formula XXII in which $R_3$ is a protector group such as 3,4 dimethoxybenzyl or benzyloxymethyl, under operating conditions such as acetonitrile in the presence of triethylamine to arrive at compounds XXIII. These compounds are then deprotected under conditions such as trifluoroacetic acid in dichloromethane (when R3=3,4 dimethoxybenzyl) or in the presence of palladium on carbon in THF under hydrogen (when R3=benzyloxymethyl) to arrive at compounds XXIV.

Scheme 5

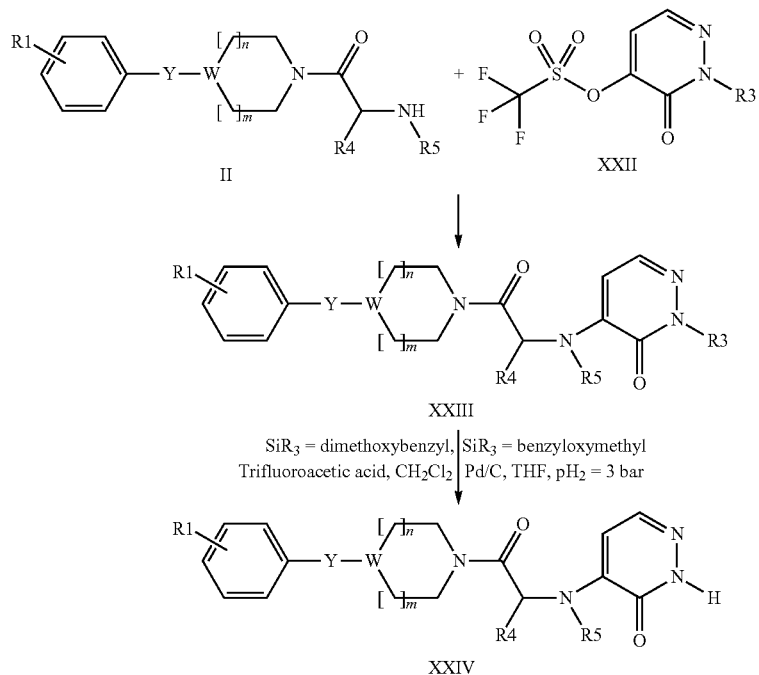

Method 6

This synthesis method of general formula I compounds is characterized (scheme 6) when U=—(C=O)CHR$_4$NR$_5$— is branched at position (4) of pyridazinone and R$_2$=H, in that the derivatives of general formula XXIV, in which R$_1$, R$_4$, R$_5$, n, m, Y, W are such as defined in general formula I, are treated with an alkylating agent R$_3$X in which X represents a halogen such as chlorine, bromine or iodine, and R$_3$ represents a C$_1$-C$_6$ straight or branched alkyl radical, or a C$_1$-C$_3$ alkyl radical substituted by groups such as: trifluoromethyl, phenyl, or a C$_3$ alkynyl under operating conditions such as DMF in the presence of K$_2$CO$_3$ to arrive at compounds XXV.

Scheme 6

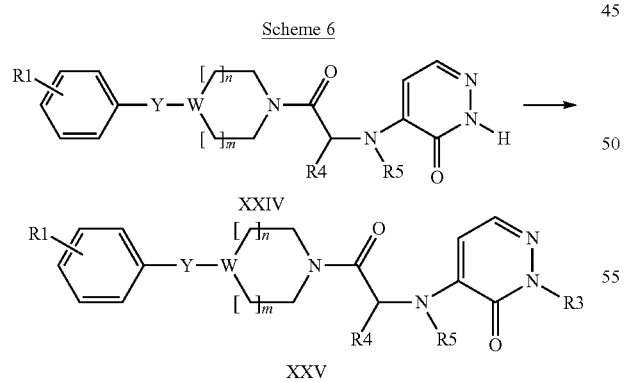

Method 7

This synthesis method of general formula I compounds is characterized (scheme 7) when U=—(C=O)NH— (branched at position 4 or 5 or 6 of pyridazinone) and R$_2$ represents H, in that the derivatives of general formula VI, in which R$_1$, m, n, Y, W are such as defined in general formula I, are condensed with compounds of general formula XXVI in which R$_3$ is such as defined in general formula I, under operating conditions such as in the presence of 4-nitrophenylchloroformiate, triethylamine in THF to arrive at compounds XXVII.

Scheme 7

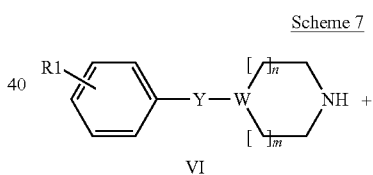

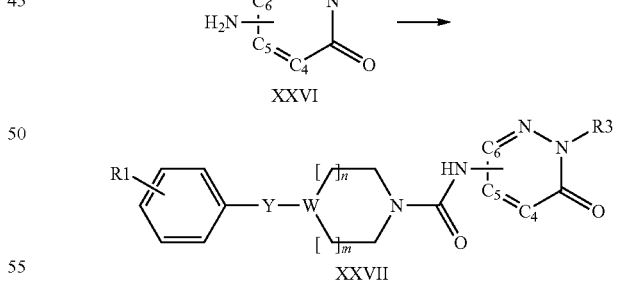

The intermediate and end compounds, if desired, may be purified following one or more purification methods chosen from among extraction, filtration, silica gel chromatography, normal or reverse phase preparative HPLC, crystallisation.

The raw materials used in the methods described above are commercially available or easily accessible to those skilled in the art following methods described in the literature.

The following examples illustrate the invention without limiting the scope thereof.

Elementary analyses, mass spectra and NMR confirm the structures of the compounds.

Intermediates 1 a) 4-(2-Trifluoromethyl-phenoxy)-piperidine hydrochloride (1a)

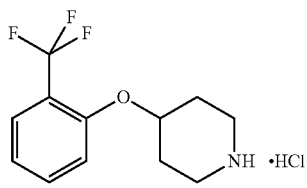 [SMILES: FC(F)(F)c1ccccc1OC1CCNCC1 ; Cl]

21.6 g (107 mmoles) of BOC-4-hydroxy-piperidine are placed in the presence of 19.1 g (118 mmoles) of 2-trifluoromethylphenol, 33.8 g (128 mmoles) of triphenylphosphine in 300 mL THF. At 0° C., 24.3 mL (128 mmoles) of DEAD are added dropwise. The reaction medium is agitated for one hour at ambient temperature then heated for 24 h at 70° C. After concentration, the residue obtained is solubilized in ether, washed with a sodium hydroxide solution (1N) then with a saturated NaCl solution. After drying over $Na_2SO_4$, the organic phases are concentrated to dryness, then solubilized in a petroleum ether-$Et_2O$ mixture 70:30 to remove the triphenylphosphine oxide. After filtering, the filtrate is concentrated, the residue obtained is purified by silica gel flash chromatography (petroleum ether-AcOEt, gradient 100:0 to 80:20 in 50 min). 17.8 g of clear oil are obtained (yield 48%). TLC silica gel 60 F 254 Merck, Petroleum ether-AcOEt 90:10, Rf=0.26. This oil is placed in 300 mL of dichloromethane in the presence of 23 mL (309 mmoles) of TFA, then this solution is agitated for 24 h at ambient temperature. The medium is concentrated and the residue obtained is solubilized in AcOEt, washed with an aqueous sodium hydroxide solution (1N), then with NaCl saturated water. After drying over $Na_2SO_4$, the organic phases are concentrated to dryness. 11.9 g of clear oil are obtained (yield 94%). This oil is solubilized in minimum EtOH then treated with 9 mL of HCl solution (5N in iPrOH). After agitation at ambient temperature for 3 h, the precipitate is filtered, rinsed with ethyl ether, then dried. 9.6 g of intermediate 1a are obtained in the form of a white solid (yield 70%). TLC silica gel 60 F 254 Merck, $CH_2Cl_2$-MeOH—$NH_4OH$, 90:9:1, Rf=0.26.

b) Intermediates 1b-1m

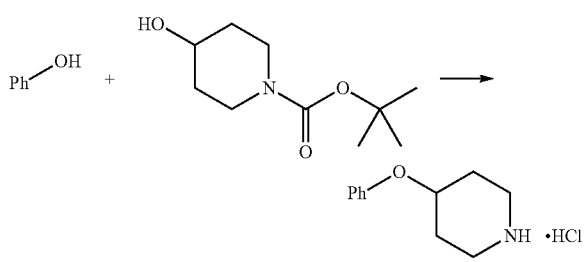

The synthesis of intermediates 1b-1m is conducted following the operating mode described for the synthesis of 1a using various phenols Ph-OH.

TABLE 1

| | Intermediates 1b-1m | | | |
|---|---|---|---|---|
| PhOH | Total yield | TLC | State | Intermediates 1b-1m |
| ![F,F,F,OH,F] | 88% | $CH_2Cl_2$—MeOH—$NH_4OH$: 90:9:1 Rf = 0.43 | solid | 1b: 4-(5-Fluoro-2-trifluoromethyl-phenoxy)-piperidine hydrochloride |
| ![Cl,OH,CF3] | 79% | $CH_2Cl_2$—MeOH—$NH_4OH$: 95:4.5:0.5 Rf = 0.37 | solid | 1c: 4-(2-Chloro-5-trifluoromethyl-phenoxy)-piperidine hydrochloride |
| ![Cl,OH,F] | 70% | $CH_2Cl_2$—MeOH—$NH_4OH$: 90:9:1 Rf = 0.24 | Solid | 1d: 4-(2-Chloro-5-fluoro-phenoxy)-pipéridine hydrochloride |

TABLE 1-continued

| Intermediates 1b-1m | | | | |
|---|---|---|---|---|
| PhOH | Total yield | TLC | State | Intermediates 1b-1m |
| 2-bromo-4,5-difluorophenol | 70% | CH₂Cl₂—MeOH: 90:10 Rf = 0.29 | solid | 1e: 4-(2-bromo-4,5-difluoro-phenoxy)-piperidine hydrochloride |
| 5-bromo-2-chlorophenol | 69% | CH₂Cl₂—MeOH—NH₄OH: 90:9:1 Rf = 0.20 | solid | 1f: 4-(5-bromo-2-chloro-phenoxy)-piperidine hydrochloride |
| 2-chlorophenol | 44% | CH₂Cl₂—MeOH—NH₄OH: 90:9:1 Rf = 0.26 | solid | 1g: 4-(2-chloro-phenoxy)-piperidine hydrochloride |
| 3,4-dichlorophenol | 79% | CH₂Cl₂—MeOH—NH₄OH: 90:9:1 Rf = 0.29 | solid | 1h: 4-(3,4-dichloro-phenoxy)-piperidine hydrochloride |
| 2,4-dichlorophenol | 73% | CH₂Cl₂—MeOH—NH₄OH: 90:9:1 Rf = 0.25 | solid | 1i: 4-(2,4-dichloro-phenoxy)-piperidine hydrochloride |
| 2,5-dichlorophenol | 77% | CH₂Cl₂—MeOH—NH₄OH: 90:9:1 Rf = 0.24 | solid | 1j: 4-(2,5-dichloro-phenoxy)-piperidine hydrochloride |
| 2,5-difluorophenol | 40% | CH₂Cl₂—MeOH—NH₄OH: 90:9:1 Rf = 0.26 | solid | 1k: 4-(2,5-difluoro-phenoxy)-piperidine hydrochloride |
| 3-trifluoromethoxyphenol | 58% | CH₂Cl₂—MeOH—NH₄OH: 90:9:1 Rf = 0.56 | solid | 1l: 4-(3-trifluoromethoxy-phenoxy)-piperidine hydrochloride |

TABLE 1-continued

Intermediates 1b-1m

| PhOH | Total yield | TLC | State | Intermediates 1b-1m |
|---|---|---|---|---|
| 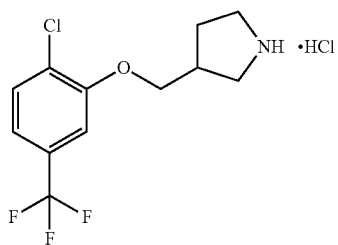 [SMILES: FC(F)(F)c1ccc(Cl)c(OCC2CCNC2)c1 ; Cl] | 45% | $CH_2Cl_2$—MeOH—AcOH: 90:9:1 Rf = 0.10 | solid | 1m: 4-(3-tert-butyl)-piperidine hydrochloride |

TLC: silica gel 60 F 254 Merck.

c) 3-(2-Chloro-5-trifluoromethyl-phenoxymethyl)-pyrrolidine hydrochloride (1n)

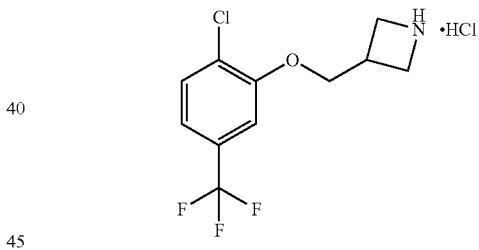

The synthesis of intermediate 1n is performed starting with 3-hydroxymethyl-1-BOC-pyrrolidine following the operating mode described for the synthesis of 1a (white solid, total yield 72%). TLC silica gel 60 F 254 Merck, $CH_2Cl_2$-MeOH—AcOH: 90:9:1, Rf=0.10 d) 3-(2-trifluoromethyl-phenoxy)-azetidine hydrochloride (1o)

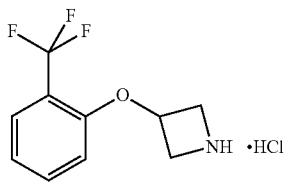 [SMILES: FC(F)(F)c1ccccc1OC1CNC1 ; Cl]

5 g (21 mmoles) of benzyhydrylazetan-3-ol are placed mL pyridine at −20° C., 2.5 mL (31 mmoles) mesyl chloride are added dropwise. The reaction medium is agitated for one hour at −20° C., placed at 6° C. for 48 h then poured into ice. The formed precipitate is filtered, rinsed with water then with petroleum ether and finally dried 48 h at 40° C. 6.59 g of a pale yellow solid are obtained (yield 99%). TLC silica gel 60 F 254 Merck, $CH_2Cl_2$—AcOEt: 80:20, Rf=0.48. 1.12 g (6.94 mmoles) of 2-trifluoromethylphenol are placed in 16 mL DMF under nitrogen. At 0° C., 0.38 g (9.46 mmoles) of NaH (60% in paraffin) are added in portions. The reaction medium is agitated for ten minutes at 0° C. then 2 g (6.31 mmoles) of the solid obtained previously are added in portions. The reaction medium is agitated for five minutes at 0° C., for one hour at ambient temperature then overnight at 80° C. After adding 5 mL water and concentrating to dryness, the residue obtained is solubilized in water and extracted with $CH_2Cl_2$. After drying over $Na_2SO_4$, the organic phases are evaporated and the residue obtained is purified by silica gel flash chromatography (petroleum ether-AcOEt, gradient 100:0 to 55:45 over 40 min). 2.05 g of colourless oil are obtained (yield 84%). TLC silica gel 60 F 254 Merck, $CH_2Cl_2$-MeOH: 90:10, Rf=0.63. This oil is placed in 35 mL 1,2-dichloroethane in the presence of 1.73 mL (16 mmoles) of 1-chloroethylchloroformate, and this solution is then agitated for 8 h at 70° C. 35 mL of MeOH are then added and the reaction medium is agitated overnight at 70° C. After concentrating to dryness, the residue obtained is triturated in petroleum ether, filtered then rinsed in petroleum ether. 1.10 g of intermediate 1o are thus obtained in the form of a pale yellow solid (yield 72%). TLC silica gel 60 F 254 Merck, $CH_2Cl_2$-MeOH—$NH_4OH$: 95:4.5:0.5, Rf=0.38.

e) 3-(2-Chloro-5-trifluoromethyl-phenoxymethyl)-azetidine hydrochloride (1p)

3 g (11.84 mmoles) of diphenylmethyl-3-(hydroxymethyl) azetidine are placed in the presence of 2.55 g (13.02 mmoles) 2-chloro-5-(trifluoromethyl)phenol and 3.72 g (14.20 mmoles) triphenylphosphine in 70 mL THF. At 0° C., 2.23 mL (14.20 mmoles) of DEAD are added dropwise. The reaction medium is agitated for one hour at ambient temperature then heated for 24 h at 70° C. After concentration, the residue obtained is solubilized in $CH_2Cl_2$ and washed with sodium hydroxide solution (1N). After drying over $MgSO_4$, the organic phases are concentrated to dryness and the residue obtained is purified by silica gel flash chromatography (petroleum ether-AcOEt, gradient 100:0 to 85:15 over 50 min). 5 g of yellow oil are obtained (yield 97%). TLC silica gel 60 F 254 Merck, petroleum ether-AcOEt: 80:20, Rf=0.39. This oil is placed in 75 mL of 1,2-dichloroethane in the presence of 3.71 mL (34.44 mmoles) of 1-chloroethylchloroformate and this solution is then agitated for 20 h at 70° C. 75 mL of MeOH are then added and the reaction medium is agitated for 24 h at 70° C. After concentrating to dryness, the residue obtained is triturated in petroleum ether, filtered then rinsed in petroleum ether. The solid obtained is solubilized in water and treated with NaHCO$_3$ then extracted with CH$_2$Cl$_2$. After drying over MgSO$_4$, the organic phases are concentrated to dryness and the residue obtained is purified by silica gel flash chromatography (CH$_2$Cl$_2$-MeOH—NH$_4$OH, gradient 100:0:0 to 90:9:1 over 50 min). 0.69 g of beige solid are obtained. This solid is solubilized in minimum EtOH then treated with 0.52 mL of HCl solution (5N in iPrOH). After agitation at ambient temperature for 3 h, the precipitate is filtered, rinsed with ethyl ether and dried. 0.691 g of intermediate 1p are thus obtained in the form of a white solid (yield 20%). TLC silica gel 60 F 254 Merck, CH$_2$Cl$_2$-MeOH—NH$_4$OH: 90:9:1, Rf=0.15.

f) (3,4-Dichloro-benzyl)-methyl-piperidin-4-yl-amine (1q)

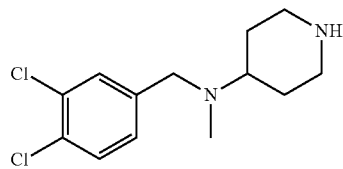 [SMILES: CN(Cc1ccc(Cl)c(Cl)c1)C1CCNCC1]

9.72 g (57 mmoles) of N-carbethoxy-4-piperidone are placed in the presence of 10 g (57 mmoles) of 3,4-dichlorobenzylamine in 170 mL of 1,2-dichloroethane. 16.9 g (79 mmoles) of sodium triacetoxyborohydride are added in portions and 3.2 mL of AcOH are then added dropwise. The reaction medium is agitated 6 h at ambient temperature then 6 g (28 mmoles) of sodium triacetoxyborohydride are added. After agitation overnight at ambient temperature, the reaction medium is treated with 60 mL of aqueous sodium hydroxide solution (2N) and extracted with CH$_2$Cl$_2$. After drying over Na$_2$SO$_4$, the organic phases are evaporated and the residue obtained is purified by silica gel flash chromatography (CH$_2$Cl$_2$—AcOEt, gradient 100:0 to 0:100 over 50 min). 19.7 g of pale yellow oil are obtained (quantitative yield). TLC silica gel 60 F 254 Merck, CH$_2$Cl$_2$-MeOH: 90:10, Rf=0.59. 0.4 g (9.96 mmoles) of NaH (60% in paraffin) are placed in 33 mL of DMF under nitrogen. At 0° C., 3 g (9.06 mmoles) of the previously obtained oil in 15 mL DMF) are added dropwise. After agitation for 15 minutes at ambient temperature, 0.62 mL (9.96 mmoles) iodomethane are added. After agitation overnight at ambient temperature, the reaction medium is treated with 300 mL water and extracted with AcOEt. After drying over Na$_2$SO$_4$, the organic phases are concentrated to dryness. 3.46 g of yellow oil are obtained (quantitative yield). TLC silica gel 60 F 254 Merck, CH$_2$Cl$_2$-MeOH: 90:10, Rf=0.78. This oil is placed in 14 mL EtOH in the presence of 1.72 g (30.8 mmoles) of potassium hydroxide (previously dissolved in 6 mL water). The reaction medium is agitated under reflux for 46 h then brought to pH 8 with an aqueous HCl solution (6N). After concentrating to dryness, the residue obtained is purified by silica gel flash chromatography (CH$_2$Cl$_2$-MeOH—NH$_4$OH, gradient 100:0:0 to 82:17:1 over 40 min). 1.59 g of intermediate 1q are thus obtained in the form of a yellow oil (yield 64%). TLC silica gel 60 F 254 Merck, CH$_2$Cl$_2$-MeOH—NH$_4$OH: 90:9:1, Rf=0.24.

g) (2-Chloro-5-trifluoromethyl-phenyl)-piperidin-4-ylmethyl-amine hydrochloride (1r)

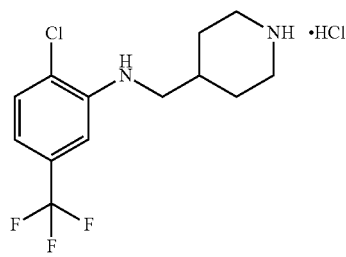 [SMILES: FC(F)(F)c1ccc(Cl)c(NCC2CCNCC2)c1 ; Cl]

6 g (23.12 mmoles) of 2-bromo-1-chloro-4-trifluoromethyl-benzene are placed in the presence of 8.65 mL (41.61 mmoles) of 1-BOC-4-aminomethyl-piperidine, 3.05 g (31.67 mmoles) of sodium tertio-butylate, 1.06 g (2.24 mmoles) of X-Phos and 1.06 g (2.24 mmoles) of Pd$_2$(dba)$_3$ in 75 mL de toluene. The reaction medium is agitated overnight at 80° C. then filtered through celite and concentrated to dryness. The residue obtained is purified by silica gel flash chromatography (petroleum ether-AcOEt, gradient 100:0 to 80:20 over 45 min). 5.96 g of yellow oil are obtained (yield 65%). TLC silica gel 60 F 254 Merck, petroleum ether-AcOEt: 80:20, Rf=0.68. 3.47 g (8.83 mmoles) of this oil are placed in 4 mL of dichloromethane in the presence of 4 mL (52.98 mmoles) TFA, then this solution is agitated overnight at ambient temperature. The medium is concentrated, the residue obtained is solubilized in CH$_2$Cl$_2$ and washed with sodium hydroxide solution (2N). After drying over MgSO$_4$, the organic phases are concentrated to dryness. 1.99 g of beige solid are obtained. This solid is solubilized in minimum EtOH then treated with 1.35 mL of HCl solution (5N in iPrOH). After agitation at ambient temperature for 3 h, the precipitate is filtered, rinsed with ethyl ether and then dried. 2 g of intermediate 1r are thus obtained in the form of a white solid (yield 68%). TLC silica gel 60 F 254 Merck, CH$_2$Cl$_2$-MeOH—NH$_4$OH: 90:9:1, Rf=0.18.

h) (2-trifluoromethyl-phenyl)-piperidin-4-ylmethyl-amine hydrochloride (1s)

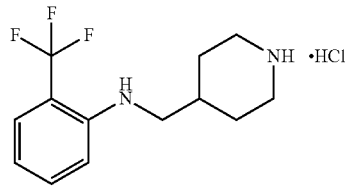 [SMILES: FC(F)(F)c1ccccc1NCC1CCNCC1 ; Cl]

The synthesis of intermediate 1s is conducted starting with 1-bromo-2-trifluoromethyl-benzene following the operating mode for the synthesis of 1r (white solid, total yield 47%). TLC silica gel 60 F 254 Merck, CH$_2$Cl$_2$-MeOH—NH$_4$OH: 90:9:1, Rf=0.23.

i) (2-trifluoromethyl-phenyl)-piperazin-1-yl-methanone hydrochloride (1t)

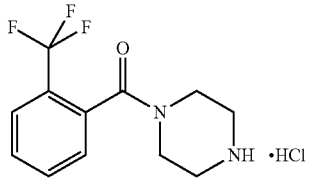 [SMILES: O=C(c1ccccc1C(F)(F)F)N1CCNCC1 ; Cl]

16.20 g (86.90 mmoles) of BOC-piperazine are placed in 120 mL of CH$_2$Cl$_2$ and 23 mL (165 mmoles) of Et$_3$N under nitrogen. At 0° C., 17.27 g (82.80 mmoles) of (2-trifluoromethyl)-benzoyl chloride are added dropwise and the reaction medium is agitated for 30 min at 0° C. then for 2 h at ambient temperature. After concentrating to dryness, the residue obtained is solubilized in water and extracted with AcOEt. After drying over Na$_2$SO$_4$, the organic phases are concentrated to dryness and the residue obtained is triturated in petroleum ether then filtered, rinsed and vacuum dried. 28.5 g of beige solid are obtained (yield 96%). TLC silica gel 60 F 254 Merck, hexane-AcOEt: 50:50, Rf=0.24. This solid is placed in the presence of 100 mL of HCl solution (5N in iPrOH) in 60 mL EtOH and the reaction medium is agitated for 2 h at 65° C. After concentrating to dryness, the residue obtained is triturated in 200 mL diethyl ether then filtered, rinsed and vacuum dried. 22.6 g of intermediate 1t are thus obtained in the form of a white solid (yield 96%). TLC silica gel 60 F 254 Merck, CH$_2$Cl$_2$-MeOH—NH$_4$OH: 90:9:1, Rf=0.34.

j) (5-Fluoro-2-trifluoromethyl-phenyl)-piperazin-1-yl-methanone hydrochloride (1u)

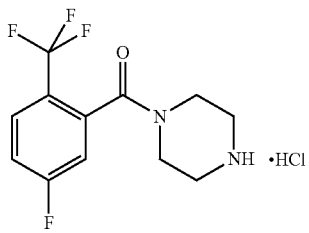 [SMILES: O=C(c1cc(F)ccc1C(F)(F)F)N1CCNCC1 ; Cl]

The synthesis of intermediate 1u is conducted starting with (5-fluoro-2-trifluoromethyl)-benzoyl chloride following the operating mode described for the synthesis of it (white solid, total yield 96%). TLC silica gel 60 F 254 Merck, CH$_2$Cl$_2$-MeOH—NH$_4$OH: 90:9:1, Rf=0.28.

Intermediates 2 a) 2-Amino-1-[4-(2-trifluoromethyl-phenoxy)-piperidin-1-yl]-ethanone (2a)

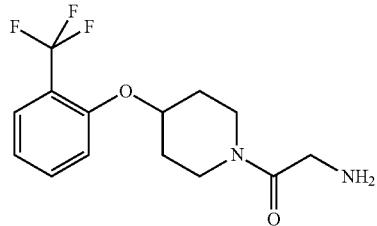 [SMILES: NCC(=O)N1CCC(Oc2ccccc2C(F)(F)F)CC1]

Method A: 2.26 g (12.92 mmoles) of BOC-glycine are placed in the presence of 4.56 g (14.21 mmoles) TBTU in mL DMF. The reaction medium is agitated for 15 minutes at ambient temperature then 5.4 mL triethylamine (38.76 mmoles) are added. After 45 minutes' agitation at ambient temperature, 3.17 g (12.92 mmoles) of intermediate 1a in base form (previously dissolved in 17 mL DMF) are added dropwise. The reaction medium is agitated for 48 h at ambient temperature then concentrated to dryness. The residue obtained is solubilized in AcOEt, washed with water then with a saturated NaCl solution. After drying over Na$_2$SO$_4$, the organic phases are evaporated and the residue obtained is purified by silica gel flash chromatography (CH$_2$Cl$_2$-MeOH—NH$_4$OH, gradient 100:0:0 to 98:1.8:0.2 over 35 min). 3.9 g of colourless oil are obtained (yield 75%). TLC silica gel 60 F 254 Merck, CH$_2$Cl$_2$-MeOH—NH$_4$OH: 95:4.5:0.5, Rf=0.72. This oil is placed in 4 mL dichloromethane in the presence of 4.26 mL (57.36 mmoles) TFA, then this solution is agitated overnight at ambient temperature. The medium is concentrated, the residue obtained is solubilized in CH$_2$Cl$_2$, washed with an aqueous sodium hydroxide solution (2N), then with NaCl-saturated water. After drying over Na$_2$SO$_4$, the organic phases are concentrated to dryness. 2.41 g of intermediate 2a are thus obtained in the form of a yellow oil (yield 83%). TLC silica gel 60 F 254 Merck, CH$_2$Cl$_2$-MeOH—NH$_4$OH: 95:4.5:0.5, Rf=0.10.

b) (S)-2-Amino-1-[4-(2-chloro-5-trifluoromethyl-phenoxy)-piperidin-1-yl]-propan-1-one (2b)

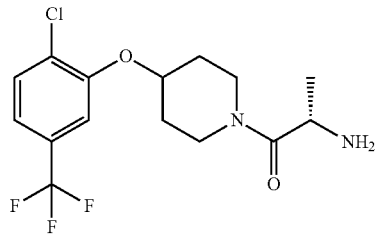 [SMILES: C[C@H](N)C(=O)N1CCC(Oc2cc(C(F)(F)F)ccc2Cl)CC1]

Method B: 2.43 g (12.86 mmoles) of BOC-L-alanine are placed in the presence of 6 mL (42.88 mmoles) Et$_3$N, 1.73 g (12.86 mmoles) HOBt, 3 g (10.72 mmoles) of intermediate 1c in base form, 2.46 g (12.86 mmoles) EDCI in 150 mL CH$_2$Cl$_2$. The reaction medium is agitated for 24 h at ambient temperature then diluted in water and extracted with CH₂Cl₂. After drying over Na₂SO₄, the organic phases are evaporated and the residue obtained is purified by silica gel flash chromatography (CH₂Cl₂-MeOH, gradient 100:0 to 94:6 over 40 min). 4.12 g of colourless oil are obtained (yield 85%). TLC silica gel 60 F 254 Merck, CH₂Cl₂-MeOH: 97:3, Rf=0.54. This oil is placed in 5 mL dichloromethane in the presence of 3.9 mL (52.56 mmoles) TFA, then this solution is agitated overnight at ambient temperature. The medium is concentrated, the residue obtained is solubilized in CH₂Cl₂, washed with an aqueous sodium hydroxide solution (2N), then with NaCl-saturated water. After drying over Na₂SO₄, the organic phases are evaporated and the residue obtained is purified by silica gel flash chromatography (CH₂Cl₂-MeOH—NH₄OH, gradient 100:0:0 to 85:13.5:1.5 over 45 min). 2.68 g of intermediate 2b are thus obtained in the form of a colourless oil (yield 87%). TLC silica gel 60 F 254 Merck, CH₂Cl₂-MeOH—NH₄OH: 95:4.5:0.5, Rf=0.39.

c) Intermediates 2c, 2d

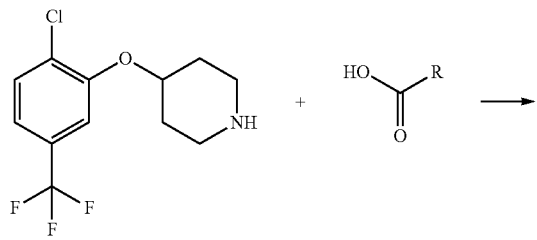

The synthesis of intermediates 2c and 2d is conducted following the operating mode described for the synthesis of 2a or 2b using various R—COOH acids.

Intermediates 3 a) 4,5-Dichloro-2-methyl-2H-pyridazin-3-one (3a)

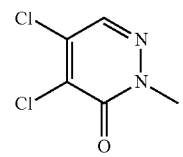

25 g (151 mmoles) of 4,5-dichloropyridazinone are placed in a stainless steel reactor in the presence of 25.13 g (181 mmoles) K₂CO₃, 1 g (3.03 mmoles) of tetrabutylammonium bromide and 14.2 mL (227 mmoles) of iodomethane in 150 mL acetonitrile. The reaction medium is agitated for 4 h at 115° C. then filtered. The filtrate is concentrated to dryness then solubilized in AcOEt and washed in acid water (pH 1), then with NaCl-saturated water. After drying over Na₂SO₄, the organic phases are evaporated and the residue obtained is purified by silica gel flash chromatography (CH₂Cl₂). 19.1 g of intermediate 3a are thus obtained in the form of a yellow solid (yield 70%). TLC silica gel 60 F 254 Merck, petroleum ether-AcOEt: 70:30, Rf=0.48.

b) 4,5-Dibromo-2-methyl-2H-pyridazin-3 (3b)

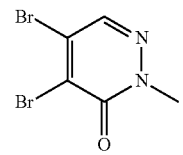

The synthesis of intermediate 3b is performed starting with 4,5-dibromopyridazinone following the operating mode

| R—COOH | Method | Tot. yld. | TLC | State | Intermediates 2c-2d |
|---|---|---|---|---|---|
| HO-CH₂-NH-C(O)-O-C(CH₃)₃ (structure) | A | 91% | CH₂Cl₂—MeOH—NH₄OH: 90:9:1 Rf = 0.32 | oil | 2c: 2-Amino-1-[4-(2-chloro-5-trifluoromethyl-phenoxy)-piperidin-1-yl]-ethanone |
| HO-CH(CH₃)-NH-C(O)-O-C(CH₃)₃ (structure) | B | 65% | CH₂Cl₂—MeOH—NH₄OH: 90:9:1 Rf = 0.06 | oil | 2d: (R)-2-Amino-1-[4-(2-chloro-5-trifluoromethyl-phenoxy)-piperidin-1-yl]-propan-1-one |

TLC: silica gel 60 F 254 Merck.

described for the synthesis of 3a (solid, yield 67%). TLC silica gel 60 F 254 Merck, petroleum ether-AcOEt: 90:10, Rf=0.50.

Intermediates 4 a) Tertio-butylic ester of (2-Methyl-3-oxo-2,3-dihydro-pyridazin-4-ylamino)-acetic acid (4a)

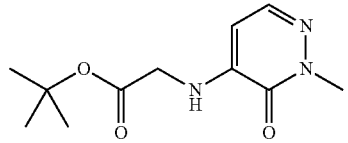 [SMILES: Cn1nccc(NCC(=O)OC(C)(C)C)c1=O]

1.44 g (8.08 mmoles) of intermediate 3a are placed in the presence of 1.06 g (8.08 mmoles) tertio-butylic ester of glycine, 0.09 g (0.4 mmoles) palladium acetate, 0.367 g (0.58 mmoles) of BINAP and 2.63 g (8.08 mmoles) of $Cs_2CO_3$ in 20 mL toluene. The reaction medium is agitated overnight at ambient temperature then for 5 h at 70° C. After concentrating to dryness, the residue is solubilized in AcOEt and washed with water. After drying over $Na_2SO_4$, the organic phases are evaporated and the residue obtained is purified by silica gel flash chromatography ($CH_2Cl_2$). 0.69 g of yellow solid are obtained (yield 30%). TLC silica gel F 254 Merck, $CH_2Cl_2$-MeOH—$NH_4OH$: 97.5:2.25:0.25, Rf=0.56. This solid is placed in the presence of 0.07 g palladium (10% on carbon) and 0.35 mL (2.52 mmoles) of $Et_3N$ in 70 mL of THF. The reaction medium is agitated in a hydrogen atmosphere (6 bars) for 48 h at ambient temperature then filtered through celite. The filtrate is concentrated to dryness and the residue is solubilized in $CH_2Cl_2$ and washed with water. After drying over $MgSO_4$, the organic phases are evaporated and the residue obtained is purified by silica gel flash chromatography ($CH_2Cl_2$-MeOH—$NH_4OH$, 99:0.9:0.1). 0.35 g of intermediate 4a are thus obtained in the form of a yellow solid (yield 58%). TLC silica gel 60 F 254 Merck, $CH_2Cl_2$-MeOH—$NH_4OH$: 97.5:2.25:0.25, Rf=0.24.

b) 4-Chloro-5-methoxy-2-methyl-2H-pyridazin-3-one (4b)

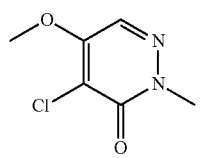

10 g (55.8 mmoles) of intermediate 3a are placed in the presence of 115 g (837 mmoles) $K_2CO_3$ in 725 mL MeOH. The reaction medium is agitated for 1 h under reflux then filtered through celite. The filtrate is concentrated to dryness and the residue solubilized in $CH_2Cl_2$ and washed with water. After drying over $Na_2SO_4$, the organic phases are evaporated and the residue obtained is purified by silica gel flash chromatography ($CH_2Cl_2$—AcOEt, gradient 100:0 to 60:40 over 45 min). 9.14 g of intermediate 4b are thus obtained in the form of a white solid (yield 94%). TLC silica gel 60 F 254 Merck, $CH_2Cl_2$—AcOEt: 50:50, Rf=0.36.

c) 4-Amino-2-methyl-2H-pyridazin-3-one (4c)

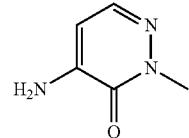

9.14 g (52 mmoles) of intermediate 4b are placed in mL hydrazine monohydrate. The reaction medium is agitated for 3 h at 80° C. then diluted in 100 mL water and extracted with $CH_2Cl_2$ then with AcOEt. After drying over $Na_2SO_4$, the organic phases are evaporated and the residue obtained is purified by silica gel flash chromatography ($CH_2Cl_2$—AcOEt, gradient 100:0 to 0:100 over 50 min). 4.17 g of intermediate 4c are thus obtained in the form of an orange-like solid (yield 63%). TLC silica 60 F 254 Merck, $CH_2Cl_2$—AcOEt: 50:50, Rf=0.16.

d) Ethyl ester of (2-Methyl-3-oxo-2,3-dihydro-pyridazin-4-ylamino)-acetic acid (4d)

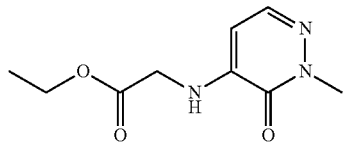

4.17 g (33.3 mmoles) of intermediate 4c are placed in the presence of 10 mL (50 mmoles) ethyl glyoxalate (50% in toluene) and 1.06 g (25% by weight) of palladium (10% on carbon) in 200 mL ethanol and 8.3 mL concentrated HCl. The reaction medium is agitated under a hydrogen atmosphere (6 bar) for 20 h at ambient temperature then filtered through celite. The filtrate is concentrated to dryness and the residue is solubilized in water and extracted with $CH_2Cl_2$. After drying over $Na_2SO_4$, the organic phases are evaporated and the residue obtained is triturated in petroleum ether (operation repeated 3 times). 7.3 g of intermediate 4d are thus obtained in the form of a yellow solid (quantitative yield). TLC silica gel 60 F 254 Merck, $CH_2Cl_2$—AcOEt: 50:50, Rf=0.35.

e) (2-Methyl-3-oxo-2,3-dihydro-pyridazin-4-ylamino)-acetic acid (4e)

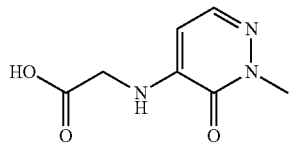

Method A: 0.34 g (1.41 mmoles) of intermediate 4d are placed in 6 mL of dichloromethane in the presence of 0.84 mL (11.28 mmoles) TFA, then this solution is agitated overnight at ambient temperature. The medium is concentrated to dryness and the residue obtained is purified by silica gel flash chromatography ($CH_2Cl_2$-MeOH, 90:10). 0.15 g of intermediate 4e are thus obtained in the form of a solid (yield 58%). TLC silica 60 F 254 Merck, $CH_2Cl_2$-MeOH—AcOH: 90:9:1, Rf=0.11.

Method B: 7.3 g (34.5 mmoles) of intermediate 4d are placed in 160 mL of methanol. At 0° C., 41.5 mL (41.5 mmoles) of aqueous sodium hydroxide solution (1N) are added dropwise and the reaction medium is agitated for 1 h at 0° C. then for 2 h30 at ambient temperature. After concentrating to dryness, the residue is solubilized in 50 mL water and the resulting solution is acidified (pH 3) with an aqueous HCl solution (6N). The precipitate formed is filtered then rinsed in water at pH 3 and vacuum dried in the presence of phosphoric acid. A first batch (4.95 g) of intermediate 4e is obtained. The filtrate is concentrated to dryness then triturated in 60 mL water (at pH 3), filtered and rinsed with water at pH 3. After vacuum drying in the presence of phosphoric acid, a second batch (0.3 g) of intermediate 4e is obtained. The two batches are combined and 5.25 g of intermediate 4e are thus obtained in the form of a grey solid (yield 83%). TLC silica gel 60 F 254 Merck, $CH_2Cl_2$-MeOH—AcOH: 70:29:1, Rf=0.33.

f) (5-Methoxy-2-methyl-3-oxo-2,3-dihydro-pyridazin-4-ylamino)-acetic acid (4f)

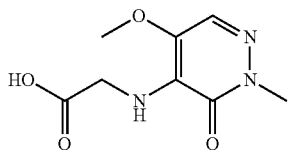

1 g (5.75 mmoles) of intermediate 4b are placed in the presence of 1 mL (7.47 mmoles) of tertio-butylic ester of glycine, 0.064 g (0.29 mmoles) palladium acetate, 0.270 g (0.43 mmoles) BINAP and 3.73 g (11.5 mmoles) $Cs_2CO_3$ in 58 mL toluene. The reaction medium is agitated for 24 h at 80° C. then 0.064 g (0.29 mmoles) of palladium acetate and 0.270 g of BINAP are added. After agitation for 24 h at 80° C., 0.064 g (0.29 mmoles) of palladium acetate and 0.270 g BINAP are added and the medium is agitated for 24 h at 80° C. The reaction medium is diluted in AcOEt and washed with water. After drying over $Na_2SO_4$, the organic phases are evaporated and the residue obtained is purified twice with silica gel flash chromatography ($CH_2Cl_2$—AcOEt, gradient 100:0 to 50:50 over 40 min). 0.289 g of orange oil are obtained (yield 19%). TLC silica gel 60 F 254 Merck, $CH_2Cl_2$—AcOEt: 50:50, Rf=0.32. This oil is placed in 5 mL of dichloromethane in the presence of 0.48 mL (6.44 mmoles) TFA then this solution is agitated for 48 h at ambient temperature. The medium is concentrated to dryness and the residue obtained is co-evaporated with EtOH (2×20 mL). 0.278 g of intermediate 4f are thus obtained in the form of an orange solid (quantitative yield). TLC silica gel 60 F 254 Merck, $CH_2Cl_2$-MeOH—AcOH: 90:9:1, Rf=0.04.

g) [Methyl-(2-methyl-3-oxo-2,3-dihydro-pyridazin-4-yl)-amino]-acetic acid (4g)

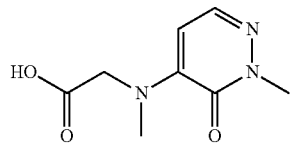

5.19 g (29.03 mmoles) of intermediate 4b are placed in the presence of 6.33 g (34.84 mmoles) of the hydrochloride of the tertio-butylic ester of sarcosine, 0.325 g (1.45 mmoles) palladium acetate, 1.31 g (2.11 mmoles) BINAP and 20.80 g (63.86 mmoles) $Cs_2CO_3$ in 50 mL toluene. The reaction medium is agitated overnight at 80° C. then 0.325 g (1.45 mmoles) palladium acetate and 40 mL toluene are added. After agitation for 24 h at 80° C., the reaction medium is concentrated to dryness and the residue is solubilized in AcOEt and washed in water then with a NaCL-saturated solution. After drying over $Na_2SO_4$, the organic phases are evaporated and the residue obtained is purified by silica gel flash chromatography ($CH_2Cl_2$-MeOH, gradient 100:0 to 99:1 over 40 min). 1.88 g of yellow solid are obtained (yield 18%). TLC silica gel 60 F 254 Merck, $CH_2Cl_2$-MeOH—$NH_4OH$: 97.5:2.25:0.25, Rf=0.61. This solid is placed in the presence of 0.188 g of palladium (10% on carbon) and 0.915 mL (6.53 mmoles) of $Et_3N$ in 40 mL THF. The reaction medium is agitated in a hydrogen atmosphere (6 bar) for 24 h at ambient temperature then filtered through celite. The filtrate is concentrated to dryness and the residue is solubilized in $CH_2Cl_2$ and washed with water. After drying over $MgSO_4$, the organic phases are evaporated and the residue obtained is purified by silica gel flash chromatography ($CH_2Cl_2$-MeOH—$NH_4OH$, gradient 100:0:0 to 97:2.7:0.3 over 40 min). 1.14 g of yellow solid are obtained (yield 68%). TLC silica gel 60 F 254 Merck, $CH_2Cl_2$-MeOH—$NH_4OH$: 90:9:1, Rf=0.80. This oil is placed in 11 mL of dichloromethane in the presence of 2.6 mL (35.37 mmoles) of TFA, and then this solution is agitated for 24 h at ambient temperature. The medium is concentrated to dryness and the residue obtained is co-evaporated with ethanol, triturated in $CH_2Cl_2$, filtered and dried. 0.419 g of intermediate 4g are obtained in the form of a beige solid (yield 48%). TLC silica gel 60 F 254 Merck, $CH_2Cl_2$-MeOH—AcOH: 80:18:2, Rf=0.09.

h) (1-Methyl-6-oxo-1,6-dihydro-pyridazin-4-ylamino)-acetic acid (4h)

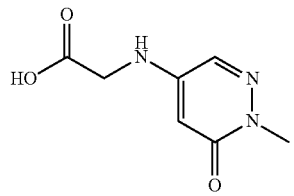

3.14 g (11.72 mmoles) of intermediate 3b are placed in a stainless steel reactor in the presence of 3.2 (23.44 mmoles) of tertio-butylic ester of glycine in 30 mL EtOH. The reaction medium is agitated for 15 h at 110° C. then concentrated to dryness. The residue obtained is purified by silica gel flash chromatography (CH$_2$Cl$_2$-MeOH, gradient 100:0 to 99:1 over 40 min). 0.825 g of yellow oil are obtained (yield 22%). TLC silica gel 60 F 254 Merck, CH$_2$Cl$_2$-MeOH—NH$_4$OH: 97.5:2.25:0.25, Rf=0.23. This oil is placed in the presence of 0.08 g palladium (10% on carbon) and 0.36 mL (2.58 mmoles) of Et$_3$N in 20 mL THF. The reaction medium is agitated in a hydrogen atmosphere (6 bar) overnight at ambient temperature then filtered through celite. The filtrate is concentrated to dryness and the residue obtained is purified by silica gel flash chromatography (CH$_2$Cl$_2$-MeOH—NH$_4$OH, 96:3.6:0.4). 0.55 g of colourless oil are obtained (yield 89%). TLC silica gel 60 F 254 Merck, CH$_2$Cl$_2$-MeOH—NH$_4$OH: 90:9:1, Rf=0.68. This oil is placed in 5 mL of CH$_2$Cl$_2$ in the presence of 1.33 mL (17.97 mmoles) of TFA, and this solution is then agitated for 26 h at ambient temperature. The medium is concentrated to dryness and the residue obtained is triturated in CH$_2$Cl$_2$, filtered then dried. 0.37 g of intermediate 4h are thus obtained in the form of a beige solid (yield 89%). TLC silica gel 60 F 254 Merck, CH$_2$Cl$_2$-MeOH: 80:20, Rf=0.14.

i) (2-Methyl-3-oxo-2,3-dihydro-pyridazin-4-yloxy)-acetic acid (4i)

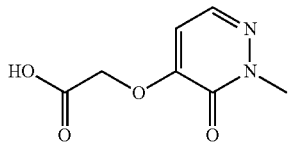

5 g (123 mmoles) of NaH (60% in paraffin) are placed in 250 mL THF under nitrogen. At 0° C., a solution of 10.26 g (113 mmoles) methyl glycolate in 20 mL THF are added dropwise and the reaction medium is agitated for 2 h30 at ambient temperature. At 0° C., a solution of 17 g (94.9 mmoles) of intermediate 3a in 220 mL THF is added dropwise. After agitation for 20 h at ambient temperature, the medium is concentrated to dryness and the residue obtained is solubilized in water then extracted with CH$_2$Cl$_2$. Next, the organic phases are washed with water then with NaCl-saturated water. After drying over Na$_2$SO$_4$, the organic phases are evaporated and the residue obtained is triturated in 100 mL diisopropylic ether. The precipitate obtained is filtered, rinsed with diisopropylic ether and dried at 40° C. 14.2 g of white solid are obtained (yield 65%). TLC silica gel 60 F 254 Merck, petroleum ether-AcOEt: 70:30, Rf=0.41. This solid is placed in the presence of 1.1 g palladium (10% on carbon) in 200 mL MeOH and 25 mL of CH$_2$Cl$_2$. The reaction medium is agitated in a hydrogen atmosphere (6 bar) for 21 h at ambient temperature then filtered through celite. The filtrate is concentrated to dryness, and the residue obtained is triturated in 150 mL diisopropylic ether. The precipitate obtained is filtered, rinsed in diisopropylic ether and dried at 40° C. 12 g of white solid are obtained (quantitative yield). TLC silica gel 60 F 254 Merck, CH$_2$Cl$_2$-MeOH: 95:5, Rf=0.18. This solid is placed in 250 mL of MeOH. At 0° C., 75 mL (72.6 mmoles) of aqueous sodium hydroxide solution are added dropwise and the reaction medium is agitated for 30 minutes at 0° C. After concentrating to dryness, the residue is solubilized in 100 mL water and the resulting solution is acidified (pH 2) with aqueous HCl solution (6N). The precipitate formed is filtered then rinsed with water at pH 2 and vacuum dried in the presence of phosphoric acid. A first batch (5.44 g) of intermediate 4i is obtained. The filtrate is concentrated to dryness then triturated in 15 mL water (at pH 2), filtered and rinsed with water at pH 2. After vacuum drying in the presence of phosphoric acid, a second batch (2.3 g) of intermediate 4i is obtained. The filtrate is concentrated to dryness, then triturated in 20 mL of MeOH. The solid obtained is removed by filtering and, after concentrating the filtrate to dryness, a third batch (3.9 g) of intermediate 4i is obtained. The three batches are grouped together and 11.64 g of intermediate 4i are thus obtained in orange solid form (quantitative yield). TLC silica gel 60 F 254 Merck, CH$_2$Cl$_2$-MeOH: 60:40, Rf=0.16.

j) (1-Methyl-6-oxo-1,6-dihydro-pyridazin-4-yloxy)-acetic acid (4j)

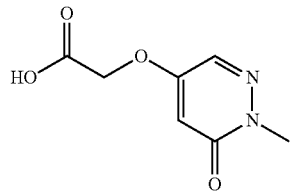

8 g (44.6 mmoles) of intermediate 3a are placed in the presence of 32 mL of KOH solution (8N) in 110 mL hexamethylphosphoramide. The reaction medium is agitated for 4 h at 125° C. then diluted in 100 mL of water. After washing with CH$_2$Cl$_2$, the aqueous phase is acidified with aqueous HCl solution (6N) then washed with CH$_2$Cl$_2$. The aqueous phase is concentrated to dryness and the residue obtained is triturated in MeOH then filtered. The filtrate is concentrated to dryness and the residue obtained is purified by silica gel flash chromatography (CH$_2$Cl$_2$-MeOH, 95:5). 4 g of white solid are obtained (yield 56%). TLC silica gel 60 F 254 Merck, CH$_2$Cl$_2$-MeOH: 80:20, Rf=0.43. This solid is placed in the presence of 2.6 mL (27.4 mmoles) of methyl bromoacetate and 8.6 g (62.2 mmoles) of K$_2$CO$_3$ in 100 mL of DMF. The reaction medium is agitated for 24 h at ambient temperature then concentrated to dryness. The residue obtained is solubilized in CH$_2$Cl$_2$ and washed with water then with NaCl-saturated solution. After drying over Na$_2$SO$_4$, the organic phases are evaporated and 5.7 g of yellow oil are obtained (yield 98%). TLC silica gel 60 F 254 Merck, CH$_2$Cl$_2$-MeOH: 95:5, Rf=0.57. This oil is placed in the presence of 1 g of palladium (10% on carbon) in 120 mL MeOH and 10 mL CH$_2$Cl$_2$. The reaction medium is agitated in a hydrogen atmosphere (7 bar) for 20 h at ambient temperature then filtered through celite. The filtrate is concentrated to dryness and the residue obtained is purified by silica gel flash chromatography (CH$_2$Cl$_2$-MeOH, gradient 100:0 to 95:5 over 40 min). 3.9 g of beige solid are obtained (yield 73%). TLC silica gel 60 F 254 Merck, CH$_2$Cl$_2$-MeOH: 95:5, Rf=0.36. This solid is placed in 90 mL MeOH. At 0° C., 25 mL (23.6 mmoles) of aqueous sodium hydroxide solution (1N) are added dropwise and the reaction medium is agitated for 45 minutes at ambient temperature. After concentrating to dryness, the residue is solubilized in 50 mL water and the resulting solution is acidified (pH 2) using aqueous HCl solution (6N). The precipitate formed is filtered then rinsed with water to pH 2 and vacuum dried in the presence of phosphoric acid. A first batch (3.16 g) of intermediate 4j is obtained. The filtrate is concentrated to dryness then triturated in 15 mL water (at pH 2), filtered and rinsed with water at pH 2. After vacuum drying in the presence of phosphoric acid, a second batch (0.2 g) of intermediate 4j is obtained. The two batches are combined and 3.31 g of intermediate 4j are thus obtained in solid orange form (yield 91%). TLC silica 60 F 254 Merck, CH$_2$Cl$_2$-MeOH: 70:30, Rf=0.17.

k) N-(2-Methyl-3-oxo-2,3-dihydro-pyridazin-4-yl)-oxalamic acid (4k)

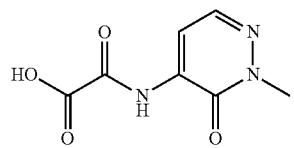

0.69 g (5.52 mmoles) of intermediate 4c are placed in 7.2 mL pyridine and 5 mL of CH$_2$Cl$_2$. At 0° C., 1.23 mL (11 mmoles) of ethyloxalyl chloride are added dropwise and the reaction medium is agitated for 2 h30 at ambient temperature then concentrated to dryness. The residue obtained is purified by silica gel flash chromatography (CH$_2$Cl$_2$-MeOH, gradient 100:0 to 95:5 in 20 min). 1.11 g of yellow solid are obtained yield 89%). TLC silica gel 60 F 254 Merck, CH$_2$Cl$_2$-MeOH: 95:5, Rf=0.70. This oil is placed in 22.5 mL MeOH. At 0° C., 5.8 mL (5.8 mmoles) of aqueous sodium hydroxide solution (1N) are added dropwise and the reaction medium is agitated for 18 h at ambient temperature then concentrated to dryness. The residue is solubilized in water and washed with AcOEt. The aqueous phase is concentrated to dryness and solubilized in 15 mL water then acidified to pH 4 with aqueous HCl solution (6N). The precipitate formed is filtered then rinsed with water at pH 4 and vacuum dried in the presence of phosphoric acid. A first batch (0.57 g) of intermediate 4k is obtained. The filtrate is concentrated to dryness then triturated in MeOH. The solid obtained is removed by filtering and, after concentrating the filtrate to dryness, a second batch (0.40 g) of intermediate 4k is obtained. The two batches are combined and 0.97 g of intermediate 4k are thus obtained in the form of an orange solid (yield 64%). TLC silica gel 60 F 254 Merck, CH$_2$Cl$_2$-MeOH—AcOH: 80:20:1, Rf=0.09.

l) 2-methyl-3-oxo-2,3-dihydro-pyridazin-4-ylic ester of trifluoro-methanesulfonic acid (4l)

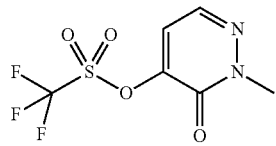 [SMILES: Cn1nccc(OS(=O)(=O)C(F)(F)F)c1=O]

3.13 g (27.9 mmoles) of potassium tertio-butylate are placed in 75 mL of THF under nitrogen. At 0° C., 1.16 mL (27.9 mmoles) of MeOH are added dropwise and the reaction medium is agitated for 10 minutes at 0° C. This suspension is added dropwise to 5 g (27.9 mmoles) of intermediate 3a previously dissolved in 40 mL of THF under nitrogen. The reaction medium is agitated for 1 h at 0° C. then for 3 h at ambient temperature. 60 mL of water are added and the medium is extracted with CH$_2$Cl$_2$. After drying over Na$_2$SO$_4$, the organic phases are concentrated to dryness and the residue obtained is purified by silica gel flash chromatography (CH$_2$Cl$_2$—AcOEt, 95:5). 4.45 g of white solid are obtained (yield 91%). TLC silica gel 60 F 254 Merck, CH$_2$Cl$_2$—AcOEt: 90:10, Rf=0.53. 6.75 g (38.6 mmoles) of this solid are placed in the presence of 0.67 g palladium (10% on carbon) and 5.4 mL Et$_3$N in 300 mL THF. The reaction medium is agitated in a hydrogen atmosphere (7 bar) for 48 h at ambient temperature then filtered through celite. The filtrate is concentrated to dryness and the residue obtained in purified by silica gel flash chromatography (CH$_2$Cl$_2$—AcOEt, gradient 90:10 to 10:90 in 40 min). 4.7 g of white solid are obtained (yield 86%). TLC silica gel 60 F 254 Merck, CH$_2$Cl$_2$—AcOEt: 50:50, Rf=0.15. This solid is placed in the presence of 19.2 g (335 mmoles) of KOH in 500 mL water. The reaction medium is agitated for 24 h at 100° C. then brought to pH 1 with aqueous HCl solution (35%). After concentrating to dryness the residue is triturated in a mixture of CH$_2$Cl$_2$-MeOH (90:10) then filtered. The filtrate is concentrated to dryness and the residue obtained is purified by silica gel flash chromatography (CH$_2$Cl$_2$-MeOH, 95:5). 3.9 g of pink solid are obtained (yield 92%). TLC silica gel 60 F 254 Merck, CH$_2$Cl$_2$-MeOH—NH$_4$OH: 80:18:2, Rf=0.20. 1 g (7.92 mmoles) of this solid are placed in 15 mL of CH$_2$Cl$_2$ under nitrogen. At −9° C., 1.4 5 mL (10.3 mmoles) of Et$_3$N then 1.8 mL (10.7 mmoles) of trifluoromethanesulfonic anhydride are added dropwise (maximum temperature −1° C.). The reaction medium is agitated for 20 minutes at −7° C. then treated with 5 mL of aqueous HCl solution (1N). After decanting, the organic phase is washed with water, then with aqueous NaHCO$_3$ solution (1%) and with NaCl-saturated water. After drying over Na$_2$SO$_4$, the organic phases are concentrated to dryness. 1.9 g of intermediate 4l are thus obtained in the form of a beige solid (yield 93%). TLC silica gel 60 F 254 Merck, CH$_2$Cl$_2$-MeOH: 95:5, Rf=0.78.

m) Tertio-butylic ester of (E)-3-(2-Methyl-3-oxo-2,3-dihydro-pyridazin-4-yl)-acrylic acid (4m)

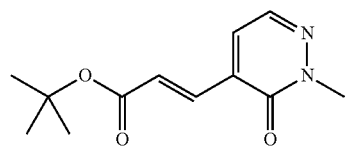 [SMILES: Cn1nccc(/C=C/C(=O)OC(C)(C)C)c1=O]

1.51 g (5.85 mmoles) of intermediate 4l are placed in the presence of 1.18 g (14 mmoles) of NaHCO$_3$, 3.42 g (11.7 mmoles) of tetrabutylammonium chloride, 1.71 mL (11.7 mmoles) of tertio-butyl acrylate and 0.026 g (0.12 mmoles) of palladium acetate in 35 mL DMF. The reaction medium is agitated for 3 h at 80° C. then concentrated to dryness. The residue is solubilized in 150 mL AcOEt and 50 mL of water then filtered through celite. The filtrate is decanted and washed with water then with NaCl-saturated water. After drying over Na$_2$SO$_4$, the organic phases are concentrated to dryness and the residue obtained is purified by silica gel flash chromatography (CH$_2$Cl$_2$). 0.9 g of intermediate 4m are n) (E)-3-(2-Methyl-3-oxo-2,3-dihydro-pyridazin-4-yl)-acrylic acid (4n)

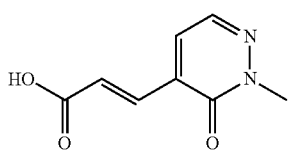

0.9 g (3.81 mmoles) of intermediate 4m are placed in 30 mL of dichloromethane in the presence of 1.7 mL (22.8 mmoles) of TFA, then this solution is agitated for 3 h at ambient temperature. The medium is concentrated, the residue obtained is triturated in 15 mL of CH₂Cl₂, filtered, then vacuum dried. 0.39 g of intermediate 4n are thus obtained in the form of a beige solid (yield 57%). TLC silica gel 60 F 254 Merck, CH₂Cl₂-MeOH: 90:10, Rf=0.14.

o) 3-(2-Methyl-3-oxo-2,3-dihydro-pyridazin-4-yl)-propionic acid (4o)

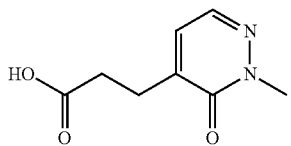

0.7 g (2.96 mmoles) of intermediate 4n are placed in the presence of 0.11 g palladium (10% on carbon) in 30 mL MeOH and 5 mL CH₂Cl₂. The reaction medium is agitated in a hydrogen atmosphere (7 bar) for 17 h at ambient temperature then filtered through celite. The filtrate is concentrated to dryness and the residue is purified by silica gel flash chromatography (CH₂Cl₂—AcOEt, gradient 100:0 to 90:10 in 40 min). 0.29 g of colourless oil are obtained (yield 41%). TLC silica gel 60 F 254 Merck, CH₂Cl₂—AcOEt: 90:10, Rf=0.27. This oil is placed in 30 mL of dichloromethane in the presence of 1.1 mL (14.56 mmoles) of TFA, and this solution is then agitated for 8 h at ambient temperature. The medium is concentrated and the residue obtained is co-evaporated with AcOEt. 0.2 g of intermediate 4o are thus obtained in the form of a beige solid (yield 91%). TLC silica gel 60 F 254 Merck, CH₂Cl₂-MeOH: 90:10, Rf=0.21.

Intermediates 5 a) 4-(tert-Butyl-dimethyl-silyloxy)-piperidine (5a)

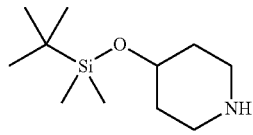

7.94 g (78.57 mmoles) of 4-hydroxypiperidine are placed in 175 mL of CH₂Cl₂ and 35 mL Et₃N under nitrogen. At 0° C., a solution of 25 g (165 mmoles) of tert-butyldimethylsilane chloride in 350 mL of CH₂Cl₂ is added dropwise. The reaction medium is agitated overnight at ambient temperature then 2.36 g (15.7 mmoles) of tert-butyldimethylsilane chloride are added. After agitation for 4 h at ambient temperature, 0.69 g (0.55 mmoles) 4-dimethylaminopyridine and 2.36 g (15.7 mmoles) tert-butyldimethylsilane chloride are added. The reaction medium is agitated overnight at ambient temperature then diluted in water and extracted with CH₂Cl₂. After drying over MgSO₄, the organic phases are evaporated and the residue obtained is purified by silica gel flash chromatography (CH₂Cl₂-MeOH—NH₄OH, gradient 100:0:0 to 90:9:1 in 50 min). 12.71 g of intermediate 5a are thus obtained in the form of yellow oil (yield 75%). TLC silica gel 60 F 254 Merck, CH₂Cl₂-MeOH—NH₄OH: 90:9:1, Rf=0.47.

b) 4-[2-(4-Hydroxy-piperidin-1-yl)-2-oxo-ethylamino]-2-methyl-2H-pyridazin-3-one (5b)

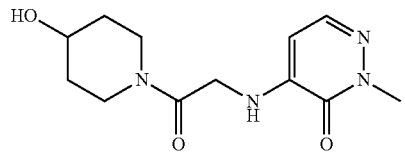 [SMILES: Cn1nccc(NCC(=O)N2CCC(O)CC2)c1=O]

6.32 g (34.50 mmoles) of intermediate 4e are placed in the presence of 19.3 mL (138 mmoles) of Et₃N, 5.59 g (41.4 mmoles) of HOBt and 7.93 g (41.4 mmoles) of EDCI in 630 mL of CH₂Cl₂. 9.66 g (44.85 mmoles) of intermediate 5a are added and the reaction medium is agitated for 20 h at ambient temperature then diluted in water and extracted with CH₂Cl₂. After drying over MgSO₄, the organic phases are evaporated and the residue obtained is purified by silica gel flash chromatography (CH₂Cl₂-MeOH, gradient 100:0 to 94:6 in 50 min). 5.75 g of colourless oil are obtained (yield 43%). TLC silica gel 60 F 254 Merck, CH₂Cl₂-MeOH: 90:10, Rf=0.64. This oil is placed in the presence of 11.19 g (302 mmoles) of ammonium fluoride in 220 mL of MeOH. The reaction medium is agitated for 48 h under reflux then concentrated to dryness. The residue obtained is purified by flash chromatography on silica (CH₂Cl₂-MeOH, gradient 100:0 to 90:10 in 50 min). 2.98 g of intermediate 5b are thus obtained in the form of a yellow solid (yield 74%). TLC silica gel 60 F 254 Merck, CH₂Cl₂-MeOH: 90:10, Rf=0.34.

c) 4-[2-(4-Hydroxy-piperidin-1-yl)-2-oxo-ethoxy]-2-methyl-2H-pyridazin-3-one (5c)

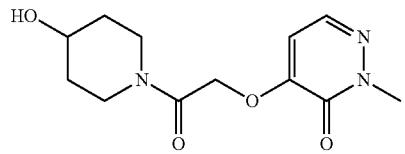 [SMILES: Cn1nccc(OCC(=O)N2CCC(O)CC2)c1=O]

11.1 g (60.2 mmoles) of intermediate 4i are placed in 250 mL of DMF under nitrogen. At 0° C., 21.3 g (66.3 mmoles) of TBTU then 16.8 mL (120 mmoles) of Et₃N then 6.1 g (60.2 mmoles) of 4-hydroxypiperidine are added. The reaction medium is agitated for 20 h at ambient temperature then concentrated to dryness. The residue obtained is purified by silica gel flash chromatography (CH₂Cl₂-MeOH, gradient 100:0 to 90:10 in 40 min). 10.14 g of intermediate 5c are thus obtained in the form of a yellow solid (yield 63%). TLC silica gel 60 F 254 Merck, CH$_2$Cl$_2$-MeOH: 80:20, Rf=0.59.

Intermediates 6 a) 6-Amino-2-methyl-2H-pyridazin-3-one (6a)

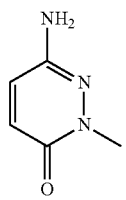

22.47 g (150 mmoles) of 3,6-dichloropyridazine are placed in 50 mL of acetic acid and agitated for 9 h under reflux. The reaction medium is diluted in 50 mL of water and concentrated to dryness. The residue obtained is purified by silica gel flash chromatography (CH$_2$Cl$_2$—AcOEt, gradient 100:0 to 50:50 in 45 min). 16.35 g of white solid are obtained (yield 82%). TLC silica gel 60 F 254 Merck, CH$_2$Cl$_2$—AcOEt: 50:50, Rf=0.31. 8 g (61.3 mmoles) of this solid are placed in a stainless steel reactor in the presence of 10.15 g (73 mmoles) of K$_2$CO$_3$, 0.39 g (1.2 mmoles) of tetrabutylammonium bromide and 5.8 mL (91.9 mmoles) of iodomethane in 100 mL acetonitrile. The reaction medium is agitated for 5 h at 115° C. then filtered through celite. The filtrate is concentrated to dryness then solubilized in water and extracted with CH$_2$Cl$_2$. After drying over Na$_2$SO$_4$, the organic phases are evaporated and the residue obtained is purified by silica gel flash chromatography (petroleum ether-AcOEt, gradient 100:0 to 55:45 in 40 min). 7.68 g of yellow solid are obtained (yield 87%). TLC silica gel 60 F 254 Merck, CH$_2$Cl$_2$—AcOEt: 95:5, Rf=0.28. 3 g (20.7 mmoles) of this solid are placed in a stainless steel reactor in 60 mL of 32% ammonia. The reaction medium is agitated for 60 h at 150° C. then concentrated to dryness. The residue obtained is purified twice by silica gel flash chromatography (CH$_2$Cl$_2$-MeOH, gradient 100:0 to 90:10 in 40 min). 1.35 g of intermediate 6a are thus obtained in the form of a yellow solid (yield 52%). TLC silica gel 60 F 254 Merck, CH$_2$Cl$_2$-MeOH: 90:10, Rf=0.31.

b) 5-Amino-2-methyl-2H-pyridazin-3-one (6b)

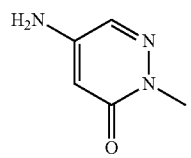

5 g (27.9 mmoles) of 4,5-dichloropyridazinone are placed in 162 mL of iodhydric acid (57%) and the reaction medium is agitated for 6 h at 137° C. The reaction medium is poured onto a solution of sodium thiosulfate (64 g) in 500 mL water then extracted with CH$_2$Cl$_2$. The organic phases are washed with water then with a NaCL-saturated solution and dried over Na$_2$SO$_4$. After evaporation, the residue obtained is purified twice by silica gel flash chromatography (CH$_2$Cl$_2$). 4.3 g of white solid are obtained consisting of 53% 5-iodo derivative and 47% 5-chloro derivative (yield 84%). TLC silica gel 60 F 254 Merck, CH$_2$Cl$_2$—AcOEt: 70:30, Rf=0.45. 2 g (9.68 mmoles) of this solid are placed in a stainless steel reactor in the presence of 70 mL ammonia (32%) and the reaction medium is agitated for 17 h at 110° C. then concentrated to dryness. The residue obtained is purified twice by silica gel flash chromatography (CH$_2$Cl$_2$-MeOH, gradient 100:0 to 90:10 in 50 min). 0.45 g of intermediate 6b are thus obtained in the form of a white solid (yield 37%). TLC silica gel 60 F 254 Merck, CH$_2$Cl$_2$-MeOH: 90-10, Rf=0.42.

Intermediates 7 a) (3-Oxo-2,3-dihydro-pyridazin-4-ylamino)-acetic acid (7a)

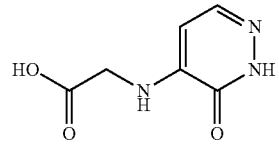 [SMILES: O=C(O)CNc1ccn[nH]c1=O]

2 g (12.20 mmoles) of 4,5-dichloropyridazin-3-one are placed in the presence of 2.4 g (14.29 mmoles) of (2,4-dimethoxyphenyl)methanol, 4 g (15.27 mmoles) of triphenylphosphine in 100 mL of THF. At 0° C., 2.24 mL (14.29 mmoles) of DEAD are added dropwise and the reaction medium is agitated for 7 hours at ambient temperature then diluted in 200 mL water and extracted with AcOEt. The organic phases are washed with a NaCl-saturated solution then dried over Na$_2$SO$_4$ and concentrated to dryness. The residue obtained is purified by silica gel flash chromatography (petroleum ether-AcOEt, gradient 90:10 to 75:15 in 50 min). 1.5 g of colourless oil are obtained (yield 37%). TLC silica gel 60 F 254 Merck, petroleum ether-AcOEt: 80:20, Rf=0.44. 0.54 g (4.77 mmoles) of potassium tertio-butylate are placed in 20 mL of THF under nitrogen. At 0° C., 0.19 mL (4.77 mmoles) of MeOH are added dropwise and the reaction medium is agitated for 10 minutes at 0° C. This suspension is added dropwise to a solution of the oil previously obtained, previously dissolved in 30 mL of THF under nitrogen. The reaction medium is agitated for 1 h at 0° C. then for 3 h at ambient temperature. 12 mL of water are added and the medium is extracted with CH$_2$Cl$_2$. After drying over Na$_2$SO$_4$, the organic phases are concentrated to dryness and the residue obtained is purified by silica gel flash chromatography (petroleum ether-AcOEt, gradient 100:0 to 80:20 in 40 min). 1.18 g of beige solid are obtained (yield 80%). TLC silica gel 60 F 254 Merck, petroleum ether-AcOEt: 90:10, Rf=0.37. 5.5 g of this solid are placed in the presence of 1 g palladium (10% on carbon) and 2 g of Et$_3$N in 200 mL of THF. The reaction medium is agitated in a hydrogen atmosphere (1 bar) for 2 h at ambient temperature. After filtering through celite, the filtrate is concentrated to dryness. 4.5 g of white solid are obtained (yield 87%). TLC silica gel 60 F 254 Merck, CH$_2$Cl$_2$-MeOH: 90:10, Rf=0.22. This solid is placed in the presence of 39 g (696 mmoles) of KOH in 600 mL water. The reaction medium is agitated overnight at 100° C. then cooled to 0° C. and brought to pH 4-5 using an aqueous HCl solution (1N). The precipitate obtained is filtered then vacuum dried. 4 g of white solid are obtained (yield 89%). TLC silica gel 60 F 254 Merck, CH$_2$Cl$_2$-MeOH: 90:10, Rf=0.15. This solid is placed in 150 mL of CH$_2$Cl$_2$ under nitrogen. At −5° C., 2.8 mL (20 mmoles) of Et$_3$N then 3.5 mL (20 mmoles) of trifluoromethanesulfonic anhydride are added dropwise (maximum temperature −1° C.). The reaction medium is agitated for 10 minutes at −5° C. then diluted in 200 mL iced water. After decanting, the organic phase is washed with NaCl-saturated water. After drying over $Na_2SO_4$, the organic phases are concentrated to dryness. 6 g of yellow oil are obtained (yield 90%). TLC silica gel 60 F 254 Merck, petroleum ether-AcOEt: 80:20, Rf=0.37. This oil is placed in the presence of 3.3 g (19.76 mmoles) tertio-butylic ester of glycine in 63 mL $Et_3N$ and 200 mL $CH_3CN$. The reaction medium is agitated for 24 h at 85° C. then concentrated to dryness. The residue is solubilized in 200 mL of $CH_2Cl_2$ then washed with water and then $NaHCO_3$-saturated solution. After drying over $Na_2SO_4$, the organic phases are concentrated to dryness and the residue obtained is purified by silica gel flash chromatography (petroleum ether-AcOEt, gradient 90:10 to 75:15 in 40 min). 1.5 g of colourless oil are obtained (yield 26%). TLC silica gel 60 F 254 Merck, $CH_2Cl_2$-MeOH: 90:10, Rf=0.33. This oil is placed in 50 mL of $CH_2Cl_2$ in the presence of 50 mL of TFA. The reaction medium is agitated for 4 hours at 40° C. then concentrated to dryness. The residue obtained is recrystallized in diethyl ether then filtered and vacuum dried. 0.8 g of intermediate 7a are thus obtained in the form of a white solid (yield 67%). TLC silica gel 60 F 254 Merck, $CH_2Cl_2$-MeOH: 70:30, Rf=0.40.

b) 4-{2-[4-(2-Chloro-5-trifluoromethyl-phenoxy)-piperidin-1-yl]-2-oxo-ethylamino}-2H-pyridazin-3-one (7b)

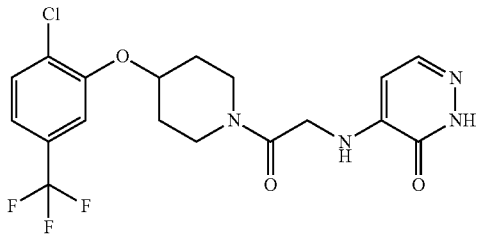 [SMILES: O=C(CNc1ccn[nH]c1=O)N1CCC(Oc2cc(C(F)(F)F)ccc2Cl)CC1]

4 g (100 mmoles) of NaH (60% in paraffin) are placed in 290 mL of DMF under nitrogen. At 0° C., 15 g (90.9 mmoles) of 4,5-dichloropyridazin-3-one are added in portions. After agitation for 45 minutes at ambient temperature, 17 g (109 mmoles) of benzyloxymethyl chloride are added dropwise and the reaction medium is agitated overnight at ambient temperature. 3 mL of water are added and the reaction medium is concentrated to dryness. The residue is solubilized in water and extracted with $CH_2Cl_2$. After drying over $Na_2SO_4$, the organic phases are concentrated to dryness. 22.8 g of white solid are obtained (yield 88%). TLC silica gel 60 F 254 Merck, $CH_2Cl_2$—AcOEt: 50:50, Rf=0.70. 5.74 g (51.2 mmoles) of potassium tertio-butylate are placed in 70 mL of THF under nitrogen. At 0° C., 2.1 mL (51.2 mmoles) of MeOH are added dropwise and the reaction medium is agitated for 20 minutes at 0° C. This suspension is added dropwise to 14.6 g (51.2 mmoles) of white solid previously obtained, previously dissolved in 70 mL of THF under nitrogen. The reaction medium is agitated for 1 h at 0° C. then for 2 h30 at ambient temperature. 100 mL of water are added and the medium is extracted with $CH_2Cl_2$. After drying over $Na_2SO_4$, the organic phases are concentrated to dryness and the residue obtained is purified by silica gel flash chromatography (petroleum ether-AcOEt, gradient 95:5 to 90:10 in 50 min). 10.3 g of white solid are obtained (yield 72%). TLC silica gel 60 F 254 Merck, $CH_2Cl_2$—AcOEt: 95:5, Rf=0.63. This solid is placed in the presence of 21 g (366 mmoles) of KOH in 900 mL water. The reaction medium is agitated for 3 h at 100° C. then brought to pH 1 with aqueous HCl solution (35%). The precipitate obtained is filtered then rinsed with water and dried in a ventilated oven for 24 h at 40° C. 8.5 g of light pink solid are obtained (yield 87%). TLC silica gel 60 F 254 Merck, $CH_2Cl_2$-MeOH: 90:10, Rf=0.51. 8 g of this solid are placed in 100 mL of $CH_2Cl_2$ under nitrogen. At −10° C., 5.45 mL (39 mmoles) of $Et_3N$ then 6.8 mL (40.5 mmoles) of trifluoromethanesulfonic anhydride are added dropwise (maximum temperature −2° C.). The reaction medium is agitated for 15 minutes at −5° C. then treated with 10 mL of aqueous HCl solution (1N). After decanting, the organic phase is washed with water, then with aqueous $NaHCO_3$ solution (1%) and with NaCl-saturated water. After drying over $Na_2SO_4$, the organic phases are concentrated to dryness. 12 g of orange solid are obtained (quantitative yield). TLC silica gel 60 F 254 Merck, $CH_2Cl_2$-MeOH: 95:5, Rf=0.85. 9.6 g (24 mmoles) of this solid are placed in the presence of 8.9 g (26.4 mmoles) of intermediate 1c in 33.5 mL (240 mmoles) of $Et_3N$ and 600 mL acetonitrile. The reaction medium is agitated for 3 h at 85° C. then concentrated to dryness. The residue is solubilized in 150 mL of $CH_2Cl_2$, washed with water and then with $NaHCO_3$-saturated solution, then with NaCl-saturated solution. After drying over $Na_2SO_4$, the organic phases are concentrated to dryness and the residue obtained is purified by silica gel flash chromatography (petroleum ether-AcOEt, 60:40). 8.9 g of pale yellow oil are obtained (yield 63%). TLC silica gel 60 F 254 Merck, petroleum ether-AcOEt: 60:40, Rf=0.49. This oil is placed in the presence of 1.75 g palladium (10% on carbon) in 300 mL EtOH. The reaction medium is agitated in a hydrogen atmosphere (3 bar) for 5 h at ambient temperature then filtered through celite. After evaporation, the residue obtained is purified twice by silica gel flash chromatography ($CH_2Cl_2$-MeOH, 97:3). 3.8 g of intermediate 7b are thus obtained in the form of a white solid (yield 58%). TLC silica gel 60 F 254 Merck, $CH_2Cl_2$-MeOH: 95:5, Rf=0.22.

An analytically pure sample is obtained by purifying 0.4 g of intermediate 7b using reverse phase flash chromatography ($C_{18}$, Water-Acetonitrile, gradient 70:30 to 0:100 in 50 min). mp=222° C.

$^1$H NMR (DMSO) ppm: 1.56-1.79 (m, 2H), 1.84-2.05 (m, 2H), 3.39-3.57 (m, 2H), 3.61-3.79 (m, 2H), 4.03 (d, 2H, J=4.40 Hz), 4.94-5.01 (m, 1H), 6.12 (d, 1H, J=4.8 Hz), 6.53-6.59 (m, 1H), 7.34 (d, 1H, J=8.40 Hz), 7.59 (d, 1H, J=4.40 Hz), 7.62 (s, 1H), 7.69 (d, 1H, J=8.00 Hz), 10.62 (s, 1H).

MS (+ESI) m/z 431 (MH+)

EXAMPLES

Example 1

2-Methyl-4-{2-oxo-2-[4-(2-trifluoromethyl-phenoxy)-piperidin-1-yl]-ethylamino}-2H-pyridazin-3-one (1)

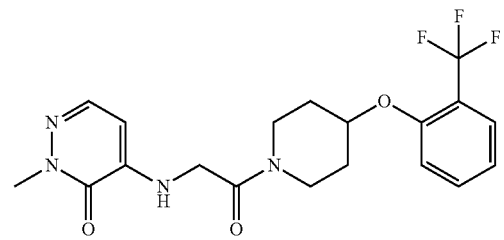 [SMILES: Cn1nccc(NCC(=O)N2CCC(Oc3ccccc3C(F)(F)F)CC2)c1=O]

Compound 1 is prepared following synthesis method 1: 0.87 g (2.88 mmoles) of derivative 2a and 0.51 g (2.88 mmoles) of 3a are placed in 10 mL of toluene in the presence of Pd(OAc)$_2$ (32 mg, 0.14 mmol), BINAP (130 mg, 0.21 mmol) and caesium carbonate (0.94 g, 2.88 mmol). This mixture is agitated under reflux for 5 h30. After concentrating the reaction medium to dryness, the residue obtained is solubilized in AcOEt and washed with water. After drying over MgSO$_4$, the organic phase is concentrated. The residue obtained is purified by flash chromatography on silica (CH$_2$Cl$_2$-MeOH—NH$_4$OH: 97.5:2.25:0.25). 0.46 g of clear oil is isolated which crystallizes (yield: 36%). TLC silica gel 60 F 254 Merck, CH$_2$Cl$_2$-MeOH—NH$_4$OH: 95:4.5:0.5, Rf=0.61. This oil is then placed in a stainless steel reactor in the presence of 46 mg Pd/C and 25 ml MeOH. The mixture is placed under 6 bar of H$_2$ at ambient temperature for 17 h. After filtering and concentrating to dryness, an oil is collected and purified by silica gel flash chromatography on (CH$_2$Cl$_2$-MeOH: 97:3). 0.29 g of yellow solid is isolated (yield: 71%)

TLC silica gel 60 F 254 Merck, CH$_2$Cl$_2$-MeOH—NH$_4$OH: 95:4.5:0.5, Rf=0.37.

mp=50° C.

$^1$H NMR (CDCl$_3$) ppm: 1.82-1.96 (m, 2H), 1.97-2.10 (m, 2H), 3.41-3.52 (m, 2H), 3.59-3.69 (m, 1H), 3.78 (s, 3H), 3.90 (d, 2H, J=4.55 Hz), 4.11-4.19 (m, 1H), 4.77-4.84 (m, 1H), 5.89 (d, 1H, J=5.05 Hz), 6.66-6.74 (m, 1H), 6.98 (d, 1H, J=8.59 Hz), 7.03 (t, 1H, J=7.58 Hz), 7.49 (td, 1H, J=7.83 Hz, J=1.26 Hz), 7.54 (d, 1H, J=4.08 Hz), 7.60 (dd, 1H, J=7.83 Hz, J=1.26 Hz).

MS (+ESI) m/z 411 (MH+)

Example 2

4-{2-[4-(5-Fluoro-2-trifluoromethyl-phenoxy)-piperidin-1-yl]-2-oxo-ethylamino}-2-methyl-2H-pyridazin-3-one (2)

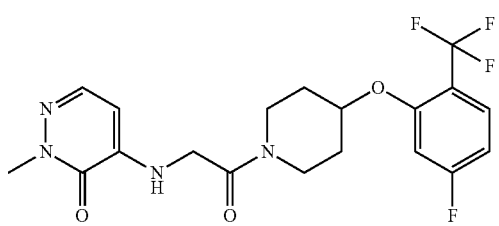 [SMILES: Cn1nccc(NCC(=O)N2CCC(Oc3cc(F)ccc3C(F)(F)F)CC2)c1=O]

Compound 2 is prepared following synthesis method 2: 0.50 g (2.72 mmol) of intermediate 4e and of intermediate 1b in base form (0.857 g, 3.26 mmol) are placed in 30 mL of CH$_2$Cl$_2$ in the presence of EDCI (0.625 g, 3.26 mmol), HOBt (0.441 g, 3.26 mmol) and Et$_3$N (1.51 mL, 10.88 mmol). The reaction medium is agitated at ambient temperature overnight, then solubilized in water and extracted with CH$_2$Cl$_2$. After drying the organic phases over MgSO$_4$, then concentrating to dryness, the residue obtained is purified by flash chromatography on silica (gradient CH$_2$Cl$_2$-MeOH: 100:0 to 93:7 in 40 nm). A white solid is isolated (0.807 g, yield: 69%).

TLC silica gel 60 F 254 Merck, CH$_2$Cl$_2$-MeOH—AcOH: 90:9:1, Rf=0.49.

mp=140° C.

$^1$H NMR (DMSO-d$_6$) ppm: 1.57-1.80 (m, 2H), 1.84-2.05 (m, 2H), 3.41-3.51 (m, 1H), 3.52-3.68 (m, 6H), 4.04 (d, 2H, J=4.54 Hz), 4.88-4.96 (m, 1H), 6.15 (d, 1H, J=4.92 Hz), 6.61-6.68 (m, 1H), 6.93 (t, 1H, J=8.08 Hz), 7.36 (d, 1H, J=11.37 Hz), 7.59 (d, 1H, J=4.67 Hz), 7.69 (t, 1H, J=7.45 Hz).

MS (+ESI) m/z 429 (MH+)

Example 3

4-{2-[4-(3-Fluoro-5-trifluoromethyl-phenoxy)-piperidin-1-yl]-2-oxo-ethylamino}-2-methyl-2H-pyridazin-3-one (3)

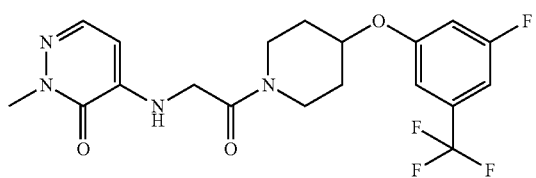 [SMILES: Cn1nccc(NCC(=O)N2CCC(Oc3cc(F)cc(C(F)(F)F)c3)CC2)c1=O]

Compound 3 is prepared following synthesis method 3: 0.7 g (2.62 mmol) of intermediate 5b are placed in 30 ml THF at 0° C. in the presence of 1.64 g (6.28 mmol) PPh$_3$ and 0.943 g (5.24 mmol) of 3-fluoro, 5-trifluoromethylphenol. 1.23 ml (6.28 mmol) of DIAD are then added, the reaction medium is agitated 5 nm at 0° C. then at ambient temperature overnight. After concentrating to dryness, the residue obtained is purified by silica gel flash chromatography (gradient CH$_2$Cl$_2$—AcOEt: 100:0 to 40:60 for 45 nm) then on C18 reverse phase silica (gradient CH$_3$CN—H$_2$O: 30:70 to 70:30 for 40 nm). 0.352 g of white solid is isolated (yield: 15%).

TLC silica gel 60 F 254 Merck, CH$_2$Cl$_2$-MeOH: 95:5, Rf=0.25.

mp=175° C.

$^1$H NMR (DMSO-d$_6$) ppm: 1.49-1.72 (m, 2H), 1.89-2.06 (m, 2H), 2.31-2.42 (m, 2H), 3.63 (s, 3H), 3.67-3.76 (m, 1H), 3.85-3.94 (m, 1H), 4.03 (d, 2H, J=4.67 Hz), 4.78-4.86 (m, 1H), 6.16 (d, 1H, J=4.92 Hz), 6.66 (t, 1H, J=4.42 Hz), 7.18-7.24 (m, 2H), 7.31 (d, 1H, J=10.73 Hz), 7.60 (d, 1H, J=4.92 Hz).

MS (+ESI) m/z 429 (MH+)

Example 4

4-{2-[4-(2-Chloro-5-trifluoromethyl-phenoxy)-piperidin-1-yl]-2-oxo-ethylamino}-2-methyl-2H-pyridazin-3-one (4)

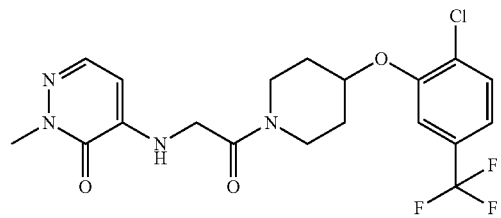 [SMILES: Cn1nccc(NCC(=O)N2CCC(Oc3cc(C(F)(F)F)ccc3Cl)CC2)c1=O]

Compound 4 is prepared from intermediate 1c in base form and intermediate 4e following synthesis method 2 (yield: 62%).

TLC silica gel 60 F 254 Merck, CH$_2$Cl$_2$—AcOEt: 80:20, Rf=0.13.

mp=158° C.

$^1$H NMR (DMSO-d$_6$) ppm: 1.57-1.80 (m. 2H), 1.85-2.05 (m, 2H), 3.40-3.56 (m, 2H), 3.59-3.79 (m, 5H), 4.04 (d, 2H, J=4.9 Hz), 4.93-5.02 (m, 1H), 6.15 (d, 1H, J=5.05 Hz), 6.62-6.68 (m, 1H), 7.34 (d, 1H, J=8.33 Hz), 7.60 (d, 1H, J=4.92 Hz), 7.62 (s, 1H), 7.69 (d, 1H, J=8.46 Hz).

MS (+ESI) m/z 445 (MH+)

Example 5

4-{2-[4-(2-Bromo-4,5-difluoro-phenoxy)-piperidin-1-yl]-2-oxo-ethylamino}-2-methyl-2H-pyridazin-3-one (5)

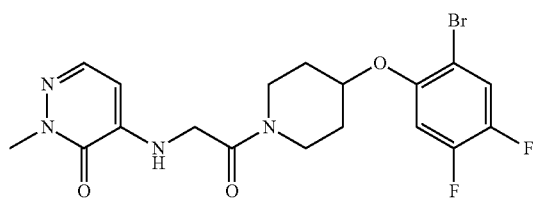 [SMILES: Cn1nccc(NCC(=O)N2CCC(Oc3cc(F)c(F)cc3Br)CC2)c1=O]

Compound 5 is prepared from intermediate 1e in base form and intermediate 4e following synthesis method 2 (yield: 71%).

TLC silica gel 60 F 254 Merck, CH$_2$Cl$_2$-MeOH: 97.5:2.5, Rf=0.40.

mp=137° C.

$^1$H NMR (DMSO-d$_6$) ppm: 1.57-1.77 (m, 2H), 1.81-2.01 (m, 2H), 3.39-3.58 (m, 2H), 3.59-3.73 (m, 5H), 4.03 (d, 2H, J=4.40 Hz), 4.73-4.80 (m, 1H), 6.15 (d, 1H, J=4.80 Hz), 6.62-6.67 (m, 1H), 7.52 (dd, 1H, J=12.80 Hz and J=7.60 Hz), 7.59 (d, 1H, J=4.80 Hz), 7.84 (t, 1H, J=9.6 Hz).

MS (+ESI) m/z 457 (MH+)

Example 6

4-{2-[4-(5-Bromo-2-chloro-phenoxy)-piperidin-1-yl]-2-oxo-ethylamino}-2-methyl-2H-pyridazin-3-one (6)

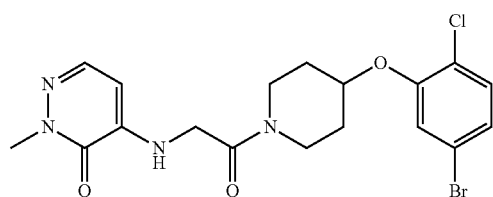 [SMILES: Cn1nccc(NCC(=O)N2CCC(Oc3cc(Br)ccc3Cl)CC2)c1=O]

Compound 6 is prepared from intermediate 1f in base form and intermediate 4e following synthesis method 2 (yield: 63%).

TLC silica gel 60 F 254 Merck, CH$_2$Cl$_2$-MeOH—AcOH: 90:9:1, Rf=0.50.

mp=160° C.

$^1$H NMR (DMSO-d$_6$) ppm: 1.55-1.77 (m, 2H), 1.84-2.03 (m, 2H), 3.28-3.52 (m, 2H), 3.60-3.79 (m, 5H), 4.04 (d, 2H, J=4.67 Hz), 4.82-4.89 (m, 1H), 6.15 (d, 1H, J=5.05 Hz), 6.63-6.68 (m, 1H), 7.17 (dd, 1H, J=8.58 Hz, and J=1.89 Hz), 7.40 (d, 1H, J=8.58 Hz), 7.53 (d, 1H, J=1.89 Hz), 7.59 (d, 1H, J=4.92 Hz).

MS (+ESI) m/z 457 (MH+)

Example 7

4-{2-[4-(2-Chloro-phenoxy)-piperidin-1-yl]-2-oxo-ethylamino}-2-methyl-2H-pyridazin-3-one (7)

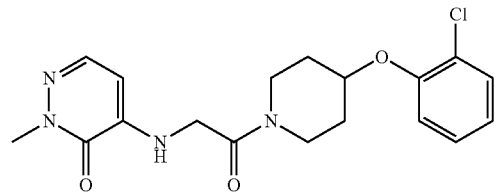 [SMILES: Cn1nccc(NCC(=O)N2CCC(Oc3ccccc3Cl)CC2)c1=O]

Compound 7 is prepared from intermediate 1g in base form and from intermediate 4e following synthesis method 2 (yield: 22%).

TLC silica gel 60 F 254 Merck, CH$_2$Cl$_2$-MeOH—NH$_4$OH: 90:9:1, Rf=0.59.

mp=142° C.

$^1$H NMR (CDCl$_3$) ppm: 1.83-2.06 (m, 4H), 3.38-3.49 (m, 1H), 3.59-3.81 (m, 5H), 3.90 (d, 2H, J=4.04 Hz), 3.97-4.05 (m, 1H), 7.64-4.71 (m, 1H), 5.89 (d, 1H, J=4.80 Hz), 6.67-6.73 (m, 1H), 6.91-6.99 (m, 2H), 7.22 (t, 1H, J=7.83 Hz), 7.39 (d, 1H, J=7.83 Hz), 7.53 (d, 1H, J=4.80 Hz).

MS (+ESI) m/z 377 (MH+)

Example 8

4-{2-[4-(2-Chloro-5-fluoro-phenoxy)-piperidin-1-yl]-2-oxo-ethylamino}-2-methyl-2H-pyridazin-3-one (8)

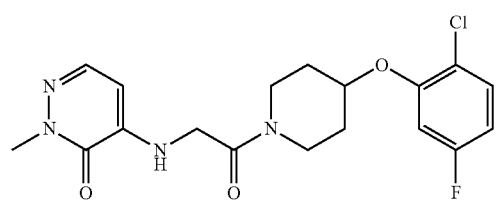 [SMILES: Cn1nccc(NCC(=O)N2CCC(Oc3cc(F)ccc3Cl)CC2)c1=O]

Compound 8 is prepared from intermediate 1d in base form and intermediate 4e following synthesis method 2 (yield: 33%).

TLC silica gel 60 F 254 Merck, CH$_2$Cl$_2$-MeOH—NH$_4$OH: 90:9:1, Rf=0.69.

mp=159° C.

$^1$H NMR (CDCl$_3$) ppm: 1.85-2.05 (m, 4H), 3.41-3.50 (m, 1H), 3.56-3.66 (m, 1H), 3.66-3.75 (m, 1H), 3.78 (s, 3H), 3.90 (d, 2H, J=4.8 Hz), 4.04-4.08 (m, 1H), 4.62-4.67 (m, 1H), 5.89 (d, 1H, J=5.2 Hz), 6.64-6.72 (m, 3H), 7.33 (dd, 1H, J=8.8 Hz and J=6.4 Hz), 7.54 (d, 1H, J=5.2 Hz).

MS (+ESI) m/z 395 (MH+)

Example 9

4-{2-[4-(2-Chloro-5-nitro-phenoxy)-piperidin-1-yl]-2-oxo-ethylamino}-2-methyl-2H-pyridazin-3-one (9)

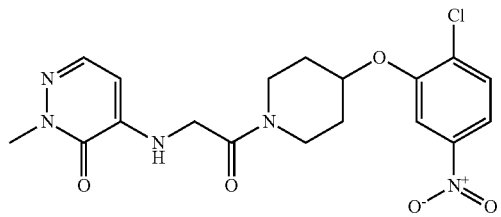 [SMILES: Cn1nccc(NCC(=O)N2CCC(Oc3cc([N+](=O)[O-])ccc3Cl)CC2)c1=O]

Compound 9 is prepared from intermediate 5b and from 2-chloro-5-nitro-phenol following synthesis method 3 (yield: 7%).

TLC silica gel 60 F 254 Merck, CH$_2$Cl$_2$-MeOH: 95:5, Rf=0.19.

mp=162° C.

$^1$H NMR (DMSO-d$_6$) ppm: 1.60-1.82 (m, 2H), 1.89-2.08 (m, 2H), 3.43-3.57 (m, 2H), 3.60-3.78 (m, 5H), 4.05 (d, 2H, J=4.80 Hz), 5.01-5.08 (m, 1H), 6.16 (d, 1H, J=5.05 Hz), 6.65 (t, 1H, J=4.80 Hz), 7.60 (d, 1H, J=4.80 Hz), 7.77 (d, 1H, J=8.71 Hz), 7.85 (dd, 1H, J=8.58 Hz and J=2.14 Hz), 8.04 (d, 1H, J=1.89 Hz).

MS (+ESI) m/z 422 (MH+)

Example 10

4-{2-[4-(3,4-Dichloro-phenoxy)-piperidin-1-yl]-2-oxo-ethylamino}-2-methyl-2H-pyridazin-3-one (10)

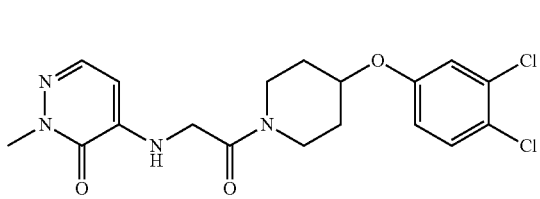 [SMILES: Cn1nccc(NCC(=O)N2CCC(Oc3ccc(Cl)c(Cl)c3)CC2)c1=O]

Compound 10 is prepared from intermediate 1h in base form and intermediate 4e following synthesis method 2 (yield: 56%).

TLC silica gel 60 F 254 Merck, CH$_2$Cl$_2$-MeOH—AcOH: 90:9:1, Rf=0.58.

mp=169° C.

$^1$H NMR (DMSO-d$_6$) ppm: 1.46-1.69 (m, 2H), 1.86-2.03 (m, 2H), 3.27-3.40 (m, 2H), 3.63 (s, 3H), 3.65-3.75 (m, 1H), 3.83-3.92 (m, 1H), 4.02 (d, 2H, J=4.42 Hz), 4.67-4.75 (m, 1H), 6.15 (d, 1H, J=4.92 Hz), 6.65 (t, 1H, J=4.42 Hz), 7.03 (dd, 1H, J=8.84 Hz and J=2.52 Hz), 7.33 (d, 1H, J=2.40 Hz), 7.52 (d, 1H, J=8.84 Hz), 7.59 d, 1H, J=4.80 Hz).

MS (+ESI) m/z 411 (MH+)

Example 11

4-{2-[4-(2,4-Dichloro-phenoxy)-piperidin-1-yl]-2-oxo-ethylamino}-2-methyl-2H-pyridazin-3-one (11)

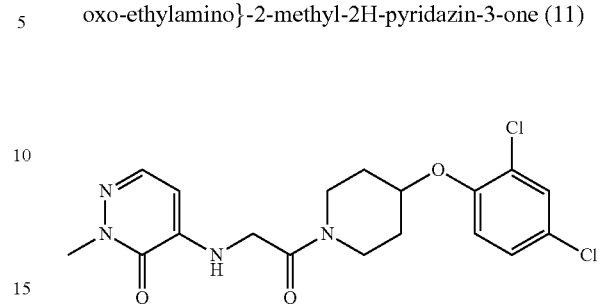

Compound 11 is prepared from intermediate 1i in base form and from intermediate 4e following synthesis method 2 (yield: 82%).

TLC silica gel 60 F 254 Merck, CH$_2$Cl$_2$-MeOH—AcOH: 90:9:1, Rf=0.55.

mp=152° C.

$^1$H NMR (DMSO-d$_6$) ppm: 1.55-1.78 (m, 2H), 1.83-2.04 (m, 2H), 3.38-3.54 (m, 2H), 3.59-3.78 (m, 5H), 4.00-4.07 (m, 2H), 4.73-4.81 (m, 1H), 6.14-6.18 (m, 1H), 6.62-6.68 (m, 1H), 7.29-7.41 (m, 2H), 7.57-7.63 (m, 2H).

MS (+ESI) m/z 411 (MH+)

Example 12

4-{2-[4-(2,5-Dichloro-phenoxy)-piperidin-1-yl]-2-oxo-ethylamino}-2-methyl-2H-pyridazin-3-one (12)

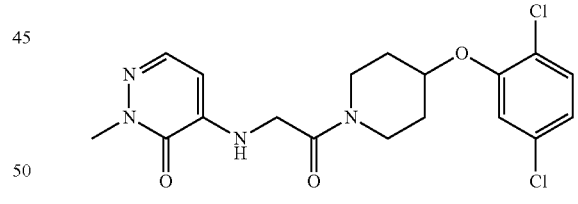

Compound 12 is prepared from intermediate 1j in base form and from intermediate 4e following synthesis method 2 (yield: 61%).

TLC silica gel 60 F 254 Merck, CH$_2$Cl$_2$-MeOH—AcOH: 90:9:1, Rf=0.66.

mp=162° C.

$^1$H NMR (DMSO-d$_6$) ppm: 1.55-1.77 (m, 2H), 1.84-2.04 (m, 2H), 3.38-3.53 (m, 2H), 3.59-3.79 (m, 5H), 4.04 (d, 2H, J=4.54 Hz), 4.81-4.89 (m, 1H), 6.16 (d, 1H, J=5.05 Hz), 6.62-6.68 (m, 1H), 7.04 (dd, 1H, J=8.46 Hz and J=1.76 Hz), 7.43 (d, 1H, J=1.76 Hz), 7.47 (d, 1H, J=8.46 Hz), 7.59 (d, 1H, J=5.05 Hz).

MS (+ESI) m/z 411 (MH+)

Example 13

4-{2-[4-(2,5-Difluoro-phenoxy)-piperidin-1-yl]-2-oxo-ethylamino}-2-methyl-2H-pyridazin-3-one (13)

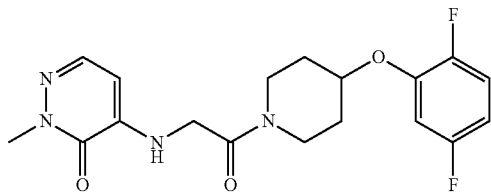 [SMILES: Cn1nccc(NCC(=O)N2CCC(Oc3cc(F)ccc3F)CC2)c1=O]

Compound 13 is prepared from intermediate 1k in base form and intermediate 4e following synthesis method 2 (yield: 84%).

TLC silica gel 60 F 254 Merck, CH$_2$Cl$_2$-MeOH—AcOH: 90:9:1, Rf=0.58.

mp=160° C.

$^1$H NMR (DMSO-d$_6$) ppm: 1.50-1.62 (m, 1H), 1.63-1.74 (m, 1H), 1.89-2.06 (m, 2H), 3.27-3.41 (m, 2H), 3.63 (s, 3H), 3.66-3.75 (m, 1H), 3.84-3.93 (m, 1H), 4.03 (d, 2H, J=4.67 Hz), 4.66-4.74 (m, 1H), 6.16 (d, 1H, J=5.05 Hz), 6.65 (t, 1H, J=4.29 Hz), 6.74-6.82 (m, 1H), 7.23-7.31 (m, 2H), 7.59 (d, 1H, J=4.92 Hz).

MS (+ESI) m/z 379 (MH+)

Example 14

4-{2-[4-(5-Fluoro-2-methyl-phenoxy)-piperidin-1-yl]-2-oxo-ethylamino}-2-methyl-2H-pyridazin-3-one (14)

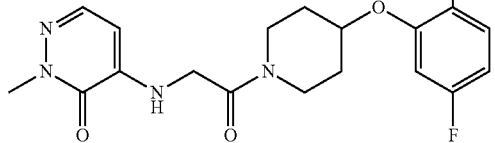

Compound 14 is prepared from intermediate 5b and from 5-fluoro-2-methyl-phenol following synthesis method 3 (yield: 15%).

TLC silica gel 60 F 254 Merck, CH$_2$Cl$_2$—AcOEt: 50:50, Rf=0.16.

mp=176° C.

$^1$H NMR (DMSO-d$_6$) ppm: 1.53-1.75 (m, 2H), 1.83-2.03 (m, 2H), 2.12 (s, 3H), 3.38-3.52 (m, 2H), 3.60-3.70 (m, 4H), 3.71-3.81 (m, 1H), 4.00-4.07 (m, 2H), 4.65-4.74 (m, 1H), 6.16 (d, 1H, J=4.67 Hz), 6.62-6.70 (m, 2H), 6.96 (d, 1H, J=11.49 Hz), 7.12-7.19 (m, 1H), 7.60 (d, 1H, J=4.80 Hz).

MS (+ESI) m/z 375 (MH+)

Example 15

2-Methyl-4-{2-[4-(2-nitro-phenoxy)-piperidin-1-yl]-2-oxo-ethylamino}-2H-pyridazin-3-one (15)

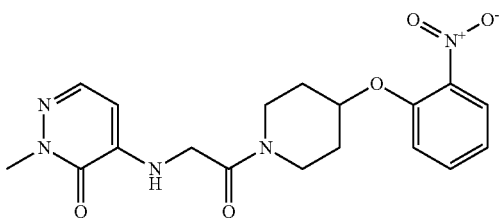 [SMILES: Cn1nccc(NCC(=O)N2CCC(Oc3ccccc3[N+](=O)[O-])CC2)c1=O]

Compound 15 is prepared from intermediate 5b and from 2-nitro-phenol following synthesis method 3 (yield: 24%).

TLC silica gel 60 F 254 Merck, CH$_2$Cl$_2$-MeOH: 80:20, Rf=0.22.

mp=160° C.

$^1$H NMR (DMSO-d$_6$) ppm: 1.59-1.80 (m, 2H), 1.83-2.03 (m, 2H), 3.42-3.51 (m, 1H), 3.53-3.66 (m, 6H), 4.04 (d, 2H, J=4.4 Hz), 4.90-4.98 (m, 1H), 6.15 (d, 1H, J=5.2 Hz), 6.65 (t, 1H, J=4.8 Hz), 7.12 (t, 1H, J=8.0 Hz), 7.47 (d, 1H, J=8.4 Hz), 7.59 (d, 1H, J=5.2 Hz), 7.64 (t, 1H, J=8.0 Hz), 7.86 (d, 1H, J=8.0 Hz).

MS (+ESI) m/z 388 (MH+)

Example 16

4-{2-[4-(5-Isopropyl-2-methyl-phenoxy)-piperidin-1-yl]-2-oxo-ethylamino}-2-methyl-2H-pyridazin-3-one (16)

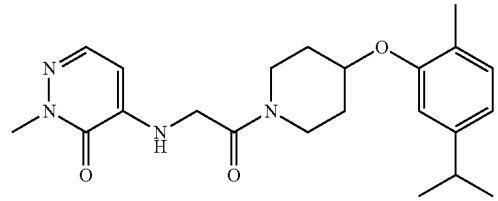 [SMILES: Cc1ccc(C(C)C)cc1OC1CCN(C(=O)CNc2ccnn(C)c2=O)CC1]

Compound 16 is prepared from 4-(5-isopropyl-2-methyl-phenoxy)-piperidine (obtained following the method described for 1a) and from intermediate 4e following synthesis method 2 (yield: 18%).

TLC silica gel 60 F 254 Merck, AcOEt: 100, Rf=0.52.

mp=159° C.

$^1$H NMR (DMSO-d$_6$) ppm: 1.18 (d, 6H, J=6.8 Hz), 1.55-1.75 (m, 2H), 1.83-2.01 (m, 2H), 2.11 (s, 3H), 2.82 (spt, 1H, J=7.2 Hz), 3.39-3.54 (m, 2H), 3.60-3.76 (m, 5H), 4.03 (d, 2H, J=5.2 Hz), 4.63-4.70 (m, 1H), 6.15 (d, 1H, J=5.2 Hz), 6.66 (t, 1H, J=4.4 Hz), 6.71 (dd, 1H, J=7.6 Hz and J=1, 2 Hz), 6.85 (d, 1H, J=1.2 Hz), 7.04 (d, 1H, J=8.0 Hz), 7.60 (d, 1H, J=4.80 Hz).

MS (+APCI) m/z 399 (MH+)

Example 17

4-({2-[4-(2-Chloro-5-trifluoromethyl-phenoxy)-piperidin-1-yl]-2-oxo-ethyl}-methyl-amino)-2-methyl-2H-pyridazin-3-one (17)

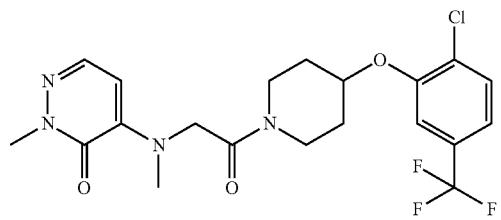 [SMILES: CN(CC(=O)N1CCC(Oc2cc(C(F)(F)F)ccc2Cl)CC1)c1ccnn(C)c1=O]

Compound 17 is prepared from intermediate 1c in base form and intermediate 4g following synthesis method 2 (yield: 63%).

TLC silica gel 60 F 254 Merck, CH$_2$Cl$_2$-MeOH: 97:3, Rf=0.16.

$^1$H NMR (DMSO-d$_6$) ppm: 1.50-1.63 (m, 1H), 1.66-1.78 (m, 1H), 1.80-1.91 (m, 1H), 1.94-2.04 (m, 1H), 2.91 (s, 3H), 3.33-3.42 (m, 2H), 3.51-3.71 (m, 5H), 4.86-5.05 (m, 3H), 6.20 (d, 1H, J=5.2 Hz), 7.33 (d, 1H, J=8.4 Hz), 7.57 (d, 1H, J=5.2 Hz), 7.59-7.61 (m, 1H), 7.69 (d, 1H, J=8.4 Hz).

MS (+ESI) m/z 459 (MH+)

Example 18

4-({2-[4-(2-Chloro-phenoxy)-piperidin-1-yl]-2-oxo-ethyl}-methyl-amino)-2-methyl-2H-pyridazin-3-one (18)

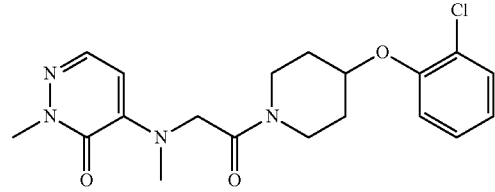 [SMILES: CN(CC(=O)N1CCC(Oc2ccccc2Cl)CC1)c1ccnn(C)c1=O]

Compound 18 is prepared from intermediate 1g in base form and intermediate 4g following synthesis method 2 (yield: 47%).

TLC silica gel 60 F 254 Merck, CH$_2$Cl$_2$-MeOH: 97:3, Rf=0.15.

$^1$H NMR (DMSO-d$_6$) ppm: 1.50-1.62 (m, 1H), 1.64-1.76 (m, 1H), 1.78-1.80 (m, 1H), 1.91-2.02 (m, 1H), 2.91 (s, 3H), 3.32-3.40 (m, 2H), 3.52-3.69 (m, 5H), 4.71-4.77 (m, 1H), 4.90 (d, 1H, J=16.80 Hz), 5.02 (d, 1H, J=16.80 Hz), 6.21 (d, 1H, J=5.30 Hz), 6.94-6.98 (m, 1H), 7.23-7.32 (m, 2H), 7.43 (dd, 1H, J=8.08 Hz and J=1.14 Hz), 7.57 (d, 1H, J=5.17 Hz).

MS (+ESI) m/z 391 (MH+)

Example 19

2-Methyl-5-{2-oxo-2-[4-(2-trifluoromethyl-phenoxy)-piperidin-1-yl]-ethylamino}-2H-pyridazin-3-one (19)

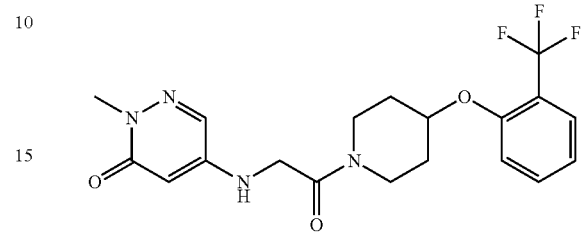

Compound 19 is prepared from intermediate 1a in base form and intermediate 4h following synthesis method 2 (yield: 40%).

TLC silica gel 60 F 254 Merck, CH$_2$Cl$_2$-MeOH—NH$_4$OH: 90:9:1, Rf=0.55.

mp=245-260° C.

$^1$H NMR (DMSO-d$_6$) ppm: 1.58-1.79 (m, 2H), 1.83-2.04 (m, 2H), 3.39-3.50 (m, 5H), 3.51-3.65 (m, 2H), 3.97 (d, 2H, J=4.8 Hz), 4.86-4.93 (m, 1H), 5.60 (d, 1H, J=2.4 Hz), 6.91 (t, 1H, J=4.8 Hz), 7.09 (t, 1H, J=7.6 Hz), 7.36 (d, 1H, J=8.8 Hz), 7.59-7.65 (m, 2H), 7.73 (d, 1H, J=2.8 Hz).

MS (+ESI) m/z 411 (MH+)

Example 20

5-{2-[4-(2-Chloro-5-fluoro-phenoxy)-piperidin-1-yl]-2-oxo-ethylamino}-2-methyl-2H-pyridazin-3-one (20)

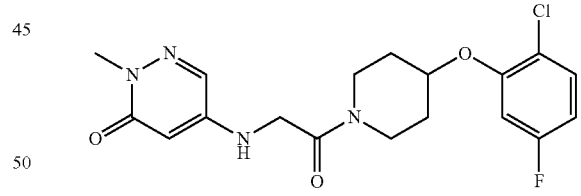

Compound 20 is prepared from intermediate 1d in base form and intermediate 4h following synthesis method 2 (yield: 27%).

TLC silica gel 60 F 254 Merck, CH$_2$Cl$_2$-MeOH—NH$_4$OH: 90:9:1, Rf=0.70.

mp=224° C.

RMN $^1$H NMR (DMSO-d$_6$) ppm: 1.54-1.77 (m, 2H), 1.84-2.03 (m, 2H), 3.37-3.52 (m, 5H), 3.60-3.78 (m, 2H), 3.97 (d, 2H, J=4.80 Hz), 4.76-4.84 (m, 1H), 5.60 (d, 1H, J=2.40 Hz), 6.83 (td, 1H, J=8.46 Hz and J=2.77 Hz), 6.91 (t, 1H, J=4.67 Hz), 7.27 (dd, 1H, J=10.99 Hz and J=2.77 Hz), 7.47 (dd, 1H, J=8.71 Hz and J=6.18 Hz), 7.73 (d, 1H, J=2.52 Hz).

MS (+APCI) m/z 395 (MH+)

Example 21

2-Methyl-4-{2-oxo-2-[4-(2-trifluoromethoxy-phenoxy)-piperidin-1-yl]-ethoxy}-2H-pyridazin-3-one (21)

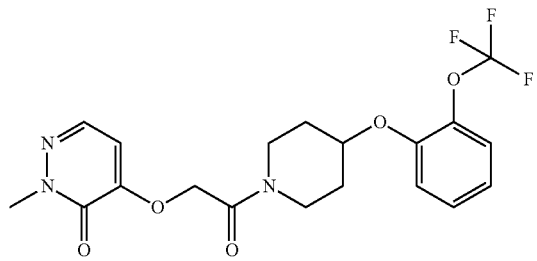 [SMILES: Cn1nccc(OCC(=O)N2CCC(Oc3ccccc3OC(F)(F)F)CC2)c1=O]

Compound 21 is prepared from intermediate 5c and 2-trifluoromethoxy-phenol following synthesis method 3 (yield: 20%).

TLC silica gel 60 F 254 Merck, $CH_2Cl_2$-MeOH: 95:5, Rf=0.35.

mp=126° C.

$^1$H NMR (DMSO-$d_6$) ppm: 1.52-1.63 (m, 1H), 1.66-1.78 (m, 1H), 1.86-2.05 (m, 2H), 3.33-3.44 (m, 2H), 3.53-3.75 (m, 5H), 4.71-4.80 (m, 1H), 5.01 (s, 2H), 6.68 (d, 1H, J=4.80 Hz), 6.99-7.06 (m, 1H), 7.32-7.38 (m, 3H), 7.74 (d, 1H, J=4.80 Hz).

MS (+ESI) m/z 428 (MH+)

Example 22

4-{2-[4-(2-Chloro-4-fluoro-phenoxy)-piperidin-1-yl]-2-oxo-ethoxy}-2-methyl-2H-pyridazin-3-one (22)

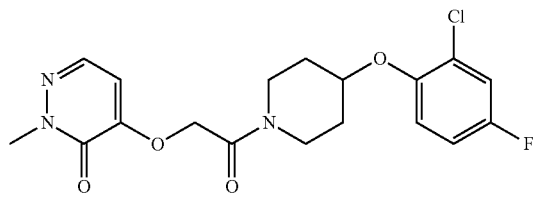 [SMILES: Cn1nccc(OCC(=O)N2CCC(Oc3ccc(F)cc3Cl)CC2)c1=O]

Compound 22 is prepared from intermediate 5c and from 2-chloro-4-fluoro-phenol following synthesis method 3 (yield: 18%).

TLC silica gel 60 F 254 Merck, $CH_2Cl_2$-MeOH: 95:5, Rf=0.35.

mp=135° C.

$^1$H NMR (DMSO-$d_6$) ppm: 1.54-1.66 (m, 1H), 1.68-1.79 (m, 1H), 1.81-1.91 (m, 1H), 1.93-2.03 (m, 1H), 3.32-3.46 (m, 2H), 3.55-3.74 (m, 5H), 4.65-4.73 (m, 1H), 5.01 (s, 2H), 6.68 (d, 1H, J=5.20 Hz), 7.17 (td, 1H, J=8.40 Hz and J=2.80 Hz), 7.30 (dd, 1H, J=9.20 Hz and J=5.20 Hz), 7.45 (dd, 1H, J=8.40 Hz and J=3.20 Hz), 7.74 (d, 1H, J=5.20 Hz).

MS (+APCI) m/z 396 (MH+)

Example 23

4-{2-[4-(2-Acetyl-5-fluoro-phenoxy)-piperidin-1-yl]-2-oxo-ethoxy}-2-methyl-2H-pyridazin-3-one (23)

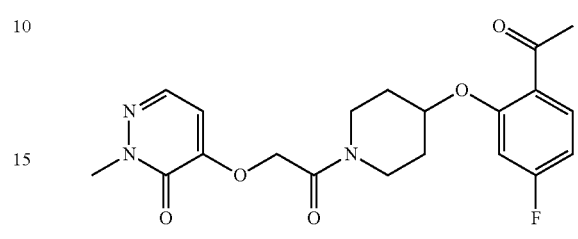

Compound 23 is prepared from intermediate 5c and from 1-(4-fluoro-2-hydroxy-phenyl)-ethanone following synthesis method 3 (yield: 17%).

TLC silica gel 60 F 254 Merck, $CH_2Cl_2$-MeOH: 95:5, Rf=0.25.

mp=192° C. $^1$H NMR (DMSO-$d_6$) ppm: 1.58-1.70 (m, 1H), 1.73-1.85 (m, 1H), 1.93-2.12 (m, 2H), 2.54 (s, 3H), 3.32-3.41 (m, 2H), 3.59-3.69 (m, 4H), 3.77-3.86 (m, 1H), 4.82-4.90 (m, 1H), 5.02 (s, 2H), 6.68 (d, 1H, J=4.80 Hz), 6.85 (td, 1H, J=8.00 Hz and J=2.00 Hz), 7.22 (dd, 1H, J=11.60 Hz and J=1.60 Hz), 7.66-7.72 (m, 1H), 7.74 (d, 1H, J=4.80 Hz).

MS (+ESI) m/z 404 (MH+)

Example 24

5-{2-[4-(2-Chloro-5-trifluoromethyl-phenoxy)-piperidin-1-yl]-2-oxo-ethoxy}-2-methyl-2H-pyridazin-3-one (24)

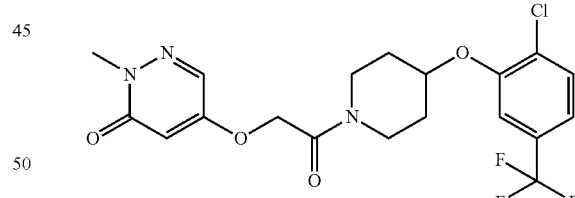

Compound 24 is prepared from intermediate 1c in base form and from intermediate 4j following synthesis method 2 (yield: 53%).

TLC silica gel 60 F 254 Merck, $CH_2Cl_2$-MeOH: 95:5, Rf=0.40.

mp=176° C.

$^1$H NMR (DMSO-$d_6$) ppm: 1.55-1.68 (m, 1H), 1.70-1.82 (s, 1H), 1.85-1.94 (m, 1H), 1.95-2.06 (m, 1H), 3.32-3.51 (m, 2H), 3.52-3.63 (m, 4H), 3.64-3.75 (m, 1H) 4.92-5.05 (m, 3H), 6.32 (d, 1H, J=2.90 Hz), 7.34 (d, 1H, J=8.21 Hz), 7.61 (s, 1H), 7.69 (d, 1H, J=8.33 Hz), 7.80 (d, 1H, J=2.78 Hz).

MS (+APCI) m/z 446 (MH+)

Example 25

5-{2-[4-(2,5-Dichloro-phenoxy)-piperidin-1-yl]-2-oxo-ethoxy}-2-methyl-2H-pyridazin-3-one (25)

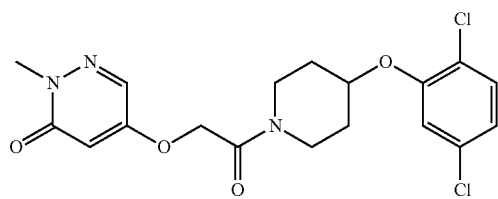 [SMILES: Cn1ncc(OCC(=O)N2CCC(Oc3cc(Cl)ccc3Cl)CC2)cc1=O]

Compound 25 is prepared from intermediate 1j in base form and intermediate 4j following synthesis method 2 (yield: 86%).

TLC silica gel 60 F 254 Merck, $CH_2Cl_2$-MeOH: 95:5, Rf=0.30.

mp=163° C.

$^1$H NMR (DMSO-$d_6$) ppm: 1.54-1.65 (m, 1H), 1.68-1.79 (m, 1H), 1.84-1.93 (m, 1H), 1.94-2.04 (m, 1H), 3.33-3.46 (m, 2H), 3.52-3.62 (m, 4H), 3.65-3.75 (m, 1H), 4.80-4.87 (m, 1H), 5.00 (s, 2H), 6.31 (d, 1H, J=2.8 Hz), 7.04 (dd, 1H, J=8.8 Hz and J=2.4 Hz), 7.42 (d, 1H, J=2.4 Hz), 7.47 (d, 1H, J=8.4 Hz), 7.80 (d, 1H, J=2.8 Hz).

MS (+APCI) m/z 412 (MH+)

Example 26

5-{2-[4-(2,4-Dichloro-phenoxy)-piperidin-1-yl]-2-oxo-ethoxy}-2-methyl-2H-pyridazin-3-one (26)

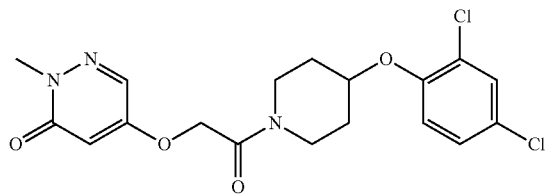 [SMILES: Cn1ncc(OCC(=O)N2CCC(Oc3ccc(Cl)cc3Cl)CC2)cc1=O]

Compound 26 is prepared from intermediate 1i in base form and intermediate 4j following synthesis method 2 (yield: 83%).

TLC silica gel 60 F 254 Merck, $CH_2Cl_2$-MeOH: 95:5, Rf=0.30.

mp=140° C.

$^1$H NMR (DMSO-$d_6$) ppm: 1.52-1.66 (m, 1H), 1.67-1.79 (m, 1H), 1.82-2.04 (m, 2H), 3.31-3.47 (m, 2H), 3.52-3.61 (m, 4H), 3.62-3.72 (m, 1H), 4.72-4.80 (m, 1H), 5.00 (s, 2H), 6.31 (d, 1H, J=2.8 Hz), 7.30 (d, 1H, J=8.8 Hz), 7.37 (dd, 1H, J=9.2 Hz and J=2.4 Hz), 7.59 (d, 1H, J=2.4 Hz), 7.79 (d, 1H, J=2.8 Hz).

MS (+APCI) m/z 412 (MH+)

Example 27

2-Methyl-4-{2-oxo-2-[3-(2-trifluoromethyl-phenoxy)-azetidin-1-yl]-ethylamino}-2H-pyridazin-3-one (27)

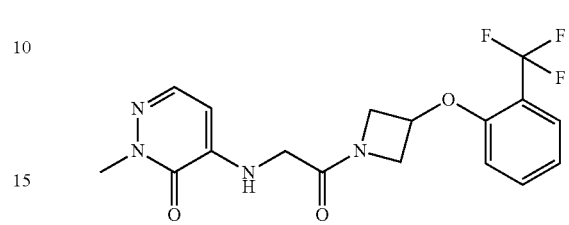

Compound 27 is prepared from intermediate 1o in base form and intermediate 4e following synthesis method 2 (yield: 35%).

TLC silica gel 60 F 254 Merck, $CH_2Cl_2$-MeOH: 90:10, Rf=0.52.

mp=122° C.

$^1$H NMR (DMSO-$d_6$) ppm: 1.72-1.85 (m, 2H), 1.93-2.04 (m, 2H), 3.45-3.56 (m, 2H), 3.63-3.75 (m, 5H), 4.97-5.04 (m, 1H), 7.33 (d, 1H, J=8.21 Hz), 7.60-7.63 (m, 1H), 7.70 (d, 1H, J=8.33 Hz), 7.89 (d, 1H, J=4.67 Hz), 8.02 (d, 1H, J=4.80 Hz).

MS (+ESI) m/z 383 (MH+)

Example 28

4-(2-{4-[(3,4-Dichloro-benzyl)-methyl-amino]-piperidin-1-yl}-2-oxo-ethylamino)-2-methyl-2H-pyridazin-3-one (28)

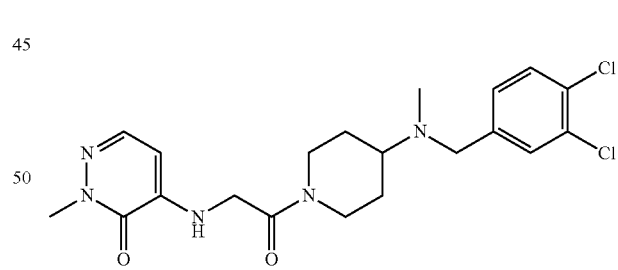

Compound 28 is prepared from intermediate 1q and intermediate 4e following synthesis method 2 (yield: 49%).

TLC silica gel 60 F 254 Merck, $CH_2Cl_2$-MeOH: 95:5, Rf=0.24.

mp=155° C.

$^1$H NMR (DMSO-$d_6$) ppm: 1.27-1.42 (m, 1H), 1.43-1.58 (m, 1H), 1.72-1.84 (m, 2H), 2.10 (s, 3H), 2.57-2.74 (m, 2H), 2.93-3.05 (m, 1H), 3.55 (s, 2H), 3.62 (s, 3H), 3.86-4.08 (m, 3H), 4.37-4.48 (m, 1H), 6.13-6.19 (m, 1H), 6.61-6.68 (m, 1H), 7.28-7.34 (m, 1H), 7.53-7.63 (m, 3H).

MS (+ESI) m/z 438 (MH+)

Example 29

4-{2-[4-(5-Fluoro-2-trifluoromethyl-benzoyl)-piperazin-1-yl]-2-oxo-ethylamino}-2-methyl-2H-pyridazin-3-one (29)

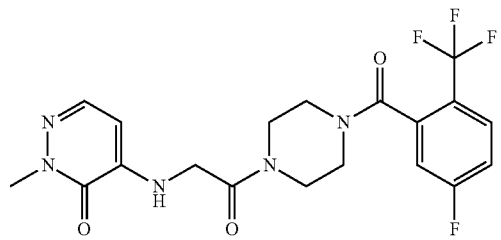 [SMILES: Cn1nccc(NCC(=O)N2CCN(C(=O)c3cc(F)ccc3C(F)(F)F)CC2)c1=O]

Compound 29 is prepared from intermediate 1u in base form and intermediate 4e following synthesis method 2 (yield: 68%).

TLC silica gel 60 F 254 Merck, CH$_2$Cl$_2$-MeOH—AcOH: 90:9:1, Rf=0.65.

mp=210° C.

$^1$H NMR (DMSO-d$_6$) ppm: 3.03-3.26 (m, 2H), 3.34-3.80 (m, 9H), 3.98-4.03 and 4.05-4.10 (two peaks, 2H), 6.06 and 6.15 (two doublets, 1H, J=4.2 Hz), 6.62-6.67 (m, 1H), 7.49-7.62 (m, 3H), 7.90-7.96 (m, 1H).

MS (+ESI) m/z 442 (MH+)

Example 30

2-Methyl-4-{2-oxo-2-[4-(2-trifluoromethyl-benzoyl)-piperazin-1-yl]-ethylamino}-2H-pyridazin-3-one (30)

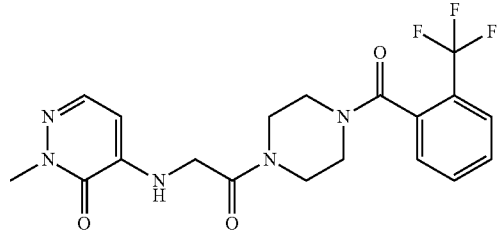 [SMILES: Cn1nccc(NCC(=O)N2CCN(C(=O)c3ccccc3C(F)(F)F)CC2)c1=O]

Compound 30 is prepared from intermediate 1t in base form and from intermediate 4e following synthesis method 2 (yield: 69%).

TLC silica gel 60 F 254 Merck, CH$_2$Cl$_2$-MeOH—AcOH: 90:9:1, Rf=0.57.

mp=170° C.

$^1$H NMR (DMSO-d$_6$) ppm: 3.01-3.22 (m, 2H), 3.34-3.48 (m, 3H), 3.51-3.81 (m, 6H), 3.96-4.01 and 4.05-4.10 (two peaks, 2H), 6.05 and 6.16 (two doublets, 1H, J=4.2 Hz), 6.62-6.67 (m, 1H), 7.50-7.62 (m, 2H), 7.64-7.70 (m, 1H), 7.73-7.80 (m, 1H), 7.81-7.86 (m, 1H).

MS (+ESI) m/z 424 (MH+)

Example 31

2-Methyl-4-(2-oxo-2-{4-[(2-trifluoromethyl-phenylamino)-methyl]-piperidin-1-yl}-ethylamino)-2H-pyridazin-3-one (31)

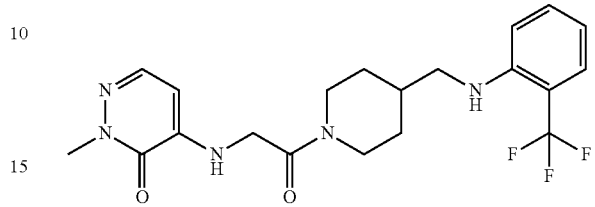

Compound 31 is prepared from intermediate 1s in base form and intermediate 4e following synthesis method 2 (yield: 63%).

TLC silica gel 60 F 254 Merck, CH$_2$Cl$_2$-MeOH—AcOH: 90:9:1, Rf=0.71.

mp=182° C.

$^1$H NMR (DMSO-d$_6$) ppm: 0.95-1.21 (m, 2H), 1.65-1.79 (m, 2H), 1.83-1.97 (m, 1H), 2.56-2.68 (m, 1H), 2.91-3.02 (m, 1H), 3.05-3.14 (m, 2H), 3.62 (s, 3H), 3.82-4.06 (m, 3H), 4.31-4.41 (m, 1H), 5.45-5.53 (m, 1H), 6.15 (d, 1H, J=5.2 Hz), 6.61-6.70 (m, 2H), 6.84 (d, 1H, J=8.4 Hz), 7.35-7.43 (m, 2H), 7.59 (d, 1H, J=4.2 Hz).

MS (+ESI) m/z 424 (MH+)

Example 32

4-(2-{4-[(2-Chloro-5-trifluoromethyl-phenylamino)-methyl]-piperidin-1-yl}-2-oxo-ethylamino)-2-methyl-2H-pyridazin-3-one (32)

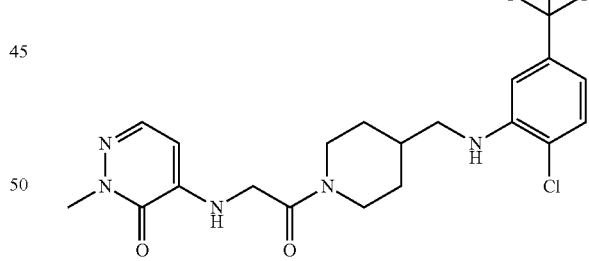

Compound 32 is prepared from intermediate 1r and from intermediate 4e following synthesis method 2 (yield: 46%).

TLC silica gel 60 F 254 Merck, CH$_2$Cl$_2$-MeOH—AcOH: 90:9:1, Rf=0.50.

mp=64° C.

$^1$H NMR (DMSO-d$_6$) ppm: 0.98-1.26 (m, 2H), 1.68-1.81 (m, 2H), 1.82-1.96 (m, 1H), 2.58-2.69 (m, 1H), 2.93-3.04 (m, 1H), 3.06-3.18 (m, 2H), 3.62 (s, 3H), 3.82-4.06 (m, 3H), 4.32-4.42 (m, 1H), 5.87 (t, 1H, J=5.6 Hz), 6.15 (d, 1H, J=4.2 Hz), 6.65 (t, 1H, J=4.4 Hz), 6.85 (d, 1H, J=8.0 Hz), 6.92 (s, 1H), 7.46 (d, 1H, J=8.0 Hz), 7.59 (d, 1H, J=5.2 Hz).

MS (+ESI) m/z 458 (MH+)

Example 33

4-{2-[3-(2-Chloro-5-trifluoromethyl-phenoxymethyl)-azetidin-1-yl]-2-oxo-ethylamino}-2-methyl-2H-pyridazin-3-one (33)

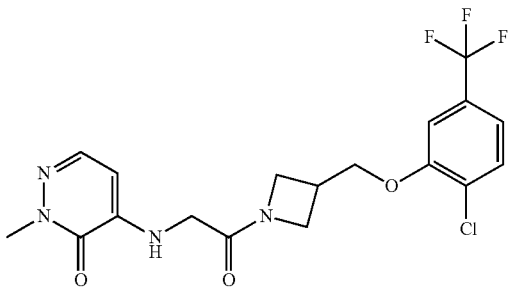 [SMILES: Cn1nccc(NCC(=O)N2CC(COc3cc(C(F)(F)F)ccc3Cl)C2)c1=O]

Compound 33 is prepared from intermediate 1p in base form and from intermediate 4e following synthesis method 2 (yield: 47%).

TLC silica gel 60 F 254 Merck, CH$_2$Cl$_2$-MeOH—AcOH: 90:9:1, Rf=0.70.

mp=174° C.

$^1$H NMR (DMSO-d$_6$) ppm: 3.05-3.15 (m, 1H), 3.62 (s, 3H), 3.75-3.83 (m, 3H), 4.00-4.10 (m, 2H), 4.28-4.38 (m, 3H), 6.04 (d, 1H, J=5.2 Hz), 6.68 (t, 1H, J=4.8 Hz), 7.34 (dd, 1H, J=8.0 Hz and J=1.2 Hz), 7.50 (d, 1H, J=1.6 Hz), 7.57 (d, 1H, J=4.8 Hz), 7.68 (dd, 1H, J=8.4 Hz and J=0.8 Hz).

MS (+ESI) m/z 431 (MH+)

Example 34

4-{2-[3-(2-Chloro-5-trifluoromethyl-phenoxymethyl)-pyrrolidin-1-yl]-2-oxo-ethylamino}-2-methyl-2H-pyridazin-3-one (34)

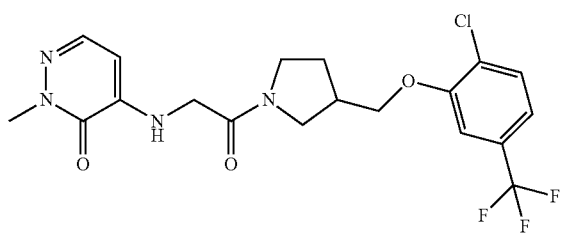 [SMILES: Cn1nccc(NCC(=O)N2CCC(COc3cc(C(F)(F)F)ccc3Cl)C2)c1=O]

Compound 34 is prepared from intermediate 1n in base form and from intermediate 4e following synthesis method 2 (yield: 16%).

TLC silica gel 60 F 254 Merck, CH$_2$Cl$_2$-MeOH—AcOH: 90:9:1, Rf=0.71.

mp=183° C.

$^1$H NMR (DMSO-d$_6$) ppm: 1.72-2.19 (m, 2H), 2.65-2.83 (m, 1H), 3.34-3.42 (m, 2H), 3.47-3.75 (m, 5H), 3.87-3.99 (m, 2H), 4.12-4.23 (m, 2H), 6.10 (d, 1H, J=4.8 Hz), 6.62 (t, 1H, J=5.2 Hz), 7.31-7.36 (m, 1H), 7.45-7.49 (m, 1H), 7.57 (dd, 1H, J=4.8 Hz and J=3.6 Hz), 7.68 (d, 1H, J=8.0 Hz).

MS (+ESI) m/z 445 (MH+)

Example 35

2-[4-(2-Chloro-5-trifluoromethyl-phenoxy)-piperidin-1-yl]-N-(2-methyl-3-oxo-2,3-dihydro-pyridazin-4-yl)-2-oxo-acetamide (35)

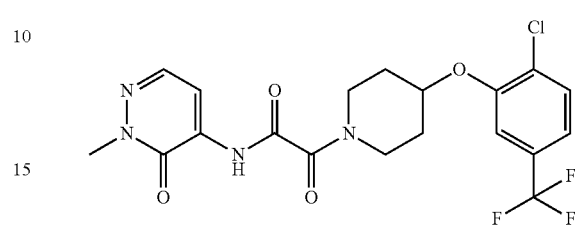

Compound 35 is prepared from intermediate 1c in base form and from intermediate 4k following synthesis method 2 (yield: 27%).

TLC silica gel 60 F 254 Merck, CH$_2$Cl$_2$—AcOEt: 80:20, Rf=0.51.

mp=205° C.

$^1$H NMR (DMSO-d$_6$) ppm: 1.72-1.85 (m, 2H), 1.93-2.04 (m, 2H), 3.45-3.56 (m, 2H), 3.63-3.75 (m, 5H), 4.97-5.04 (m, 1H), 7.33 (d, 1H, J=8.21 Hz), 7.60-7.63 (m, 1H), 7.70 (d, 1H, J=8.33 Hz), 7.89 (d, 1H, J=4.67 Hz), 8.02 (d, 1H, J=4.80 Hz), 10.78 (s, 1H).

MS (+ESI) m/z 459 (MH+)

Example 36

4-{(E)-3-[4-(2-Chloro-5-trifluoromethyl-phenoxy)-piperidin-1-yl]-3-oxo-propenyl}-2-methyl-2H-pyridazin-3-one (36)

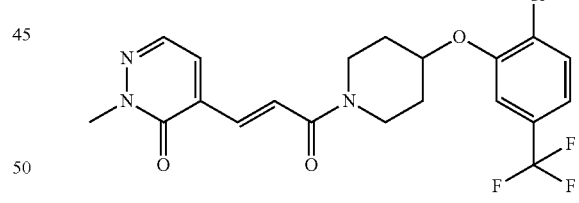

Compound 36 is prepared from intermediate 1c in base form and from intermediate 4n following synthesis method 2 (yield: 82%).

TLC silica gel 60 F 254 Merck, CH$_2$Cl$_2$-MeOH: 97.5:2.5, Rf=0.45.

mp=154° C.

$^1$H NMR (DMSO-d$_6$) ppm: 1.59-1.78 (m, 2H), 1.89-2.05 (m, 2H), 3.52-3.68 (m, 2H), 3.72 (s, 3H), 3.75-3.88 (m, 2H), 4.94-5.03 (m, 1H), 7.34 (d, 1H, J=8.40 Hz), 7.45 (d, 1H, J=15.20 Hz), 7.62 (s, 1H), 7.70 (d, 1H, J=8.40 Hz), 7.78 (d, 1H, J=4.40 Hz), 7.89 (d, 1H, J=15.20 Hz), 7.97 (d, 1H, J=4.40 Hz).

MS (+ESI) m/z 442 (MH+)

Example 37

4-{3-[4-(2-Chloro-5-trifluoromethyl-phenoxy)-piperidin-1-yl]-3-oxo-propyl}-2-methyl-2H-pyridazin-3-one (37)

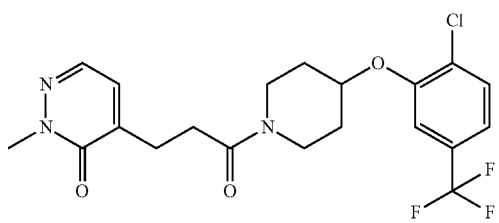 [SMILES: Cn1nccc(CCC(=O)N2CCC(Oc3cc(C(F)(F)F)ccc3Cl)CC2)c1=O]

Compound 37 is prepared from intermediate 1c in base form and from intermediate 4o following synthesis method 2 (yield: 88%).

TLC silica gel 60 F 254 Merck, CH$_2$Cl$_2$-MeOH: 95:5, Rf=0.45.

$^1$H NMR (DMSO-d$_6$) ppm: 1.51-1.71 (m, 2H), 1.81-1.98 (m, 2H), 2.60-2.72 (m, 4H), 3.38-3.48 (m, 2H), 3.61-3.75 (m, 5H), 4.90-4.98 (m, 1H), 7.28 (d, 1H, J=4.40 Hz), 7.33 (dd, 1H, J=8.00 Hz and J=0.80 Hz), 7.60 (d, 1H, J=1.20 Hz), 7.69 (d, 1H, J=8.40 Hz), 7.80 (d, 1H, J=4.00 Hz).

MS (+ESI) m/z 444 (MH+)

Example 38

4-{(R)-2-[4-(2-Chloro-5-trifluoromethyl-phenoxy)-piperidin-1-yl]-1-methyl-2-oxo-ethylamino}-2-methyl-2H-pyridazin-3-one (38)

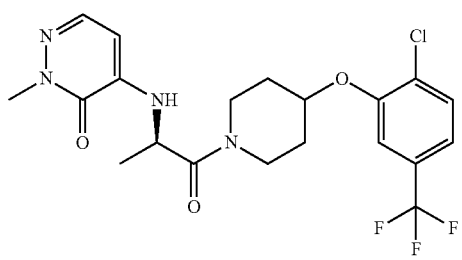 [SMILES: C[C@@H](Nc1ccnn(C)c1=O)C(=O)N1CCC(Oc2cc(C(F)(F)F)ccc2Cl)CC1]

Compound 38 is prepared following synthesis method 4: 0.5 g (1.93 mmol) of intermediate 4l is placed in the presence of 0.742 g (2.12 mmol) of intermediate 2d in the presence of 2.69 ml (19.3 mmol) Et$_3$N in 30 mL acetonitrile. The reaction medium is heated to 85° C. for 3 h. After concentrating to dryness, the residue is solubilized in dichloromethane, washed with water, then with a sodium bicarbonate saturated solution and then with brine. The organic phases are dried over MgSO$_4$ then concentrated to dryness. The residue obtained is purified by silica gel flash chromatography (petroleum ether-AcOEt, 100:0 to 10:90 for 45 nm). 0.201 g of white solid are isolated (yield: 23%).

TLC silica gel 60 F 254 Merck, CH$_2$Cl$_2$-MeOH: 95:5, Rf=0.43.

mp=70° C.

$^1$H NMR (DMSO-d$_6$) ppm: 1.26 (d, 3H, J=6.4 Hz), 1.54-1.77 (m, 2H), 1.84-2.05 (m, 2H), 3.36-3.55 (m, 2H), 3.56-3.89 (m, 5H), 4.58-4.69 (m, 1H), 4.91-5.03 (m, 1H), 6.23 (t, 1H, J=4.4 Hz), 6.66 (d, 1H, J=7.6 Hz), 7.34 (d, 1H, J=8.4 Hz), 7.58-7.63 (m, 2H), 7.69 (d, 1H, J=8.0 Hz).

MS (+ESI) m/z 459 (MH+)

Example 39

4-{(S)-2-[4-(2-Chloro-5-trifluoromethyl-phenoxy)-piperidin-1-yl]-1-methyl-2-oxo-ethylamino}-2-methyl-2H-pyridazin-3-one (39)

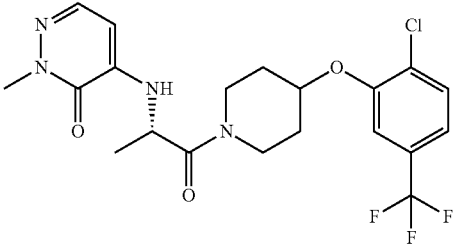 [SMILES: C[C@H](Nc1ccnn(C)c1=O)C(=O)N1CCC(Oc2cc(C(F)(F)F)ccc2Cl)CC1]

Compound 39 is prepared from intermediate 4l and intermediate 2b following synthesis method 4 (yield: 22%).

TLC silica gel 60 F 254 Merck, CH$_2$Cl$_2$-MeOH: 95:5, Rf=0.43.

mp=70° C.

$^1$H NMR (DMSO-d$_6$) ppm: 1.26 (d, 3H, J=6.4 Hz), 1.54-1.77 (m, 2H), 1.84-2.05 (m, 2H), 3.36-3.55 (m, 2H), 3.56-3.89 (m, 5H), 4.58-4.69 (m, 1H), 4.91-5.03 (m, 1H), 6.23 (t, 1H, J=4.4 Hz), 6.66 (d, 1H, J=7.6 Hz), 7.34 (d, 1H, J=8.4 Hz), 7.58-7.63 (m, 2H), 7.69 (d, 1H, J=8.4 Hz).

MS (+ESI) m/z 459 (MH+)

Example 40

4-{2-[4-(2-Chloro-5-trifluoromethyl-phenoxy)-piperidin-1-yl]-2-oxo-ethylamino}-2H-pyridazin-3-one (40)

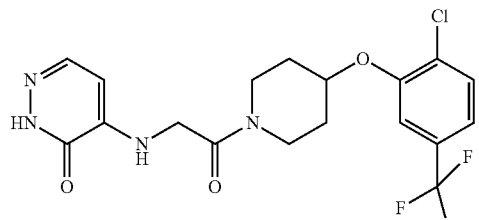

Compound 40 is prepared following synthesis method 5 described for intermediate 7b (yield: 59%).

TLC silica gel 60 F 254 Merck, CH$_2$Cl$_2$-MeOH: 95:5, Rf=0.40.

mp=222° C.

$^1$H NMR (DMSO-d$_6$) ppm: 1.58-1.68 (m, 1H), 1.69-1.79 (m, 1H), 1.86-1.95 (m, 1H), 1.96-2.05 (m, 1H), 3.41-3.56 (m, 2H), 3.62-3.78 (m, 2H), 4.03 (d, 2H, J=4.40 Hz), 4.94-5.01 (m, 1H), 6.12 (d, 1H, J=4.80 Hz), 6.56 (t, 1H, J=3.60 Hz), 7.34 (d, 1H, J=8.40 Hz), 7.59 (d, 1H, J=4.40 Hz), 7.62 (s, 1H), 7.70 (d, 1H, J=8.00 Hz), 12.62 (s, 1H).

MS (+ESI) m/z 431 (MH+).

Example 41

4-{2-[4-(2,5-dichloro-phenoxy)-piperidin-1-yl]-2-oxo-ethylamino}-2H-pyridazin-3-one (41)

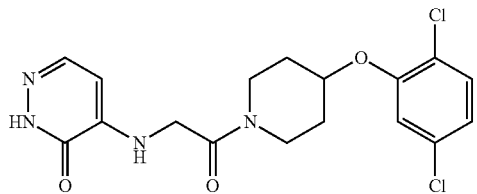

Compound 41 is prepared from intermediate 7a and intermediate 1j following synthesis method 2 (yield: 50%).

¹H NMR (DMSO-d₆) ppm: 1.55-1.77 (m, 2H), 1.84-2.04 (m, 2H), 3.53-3.37 (m, 2H), 3.61-3.80 (m, 2H), 3.98-4.07 (m, 2H), 4.80-4.89 (m, 1H), 6.10-6.15 (m, 1H), 6.52-6.59 (m, 1H), 7.04 (d, 1H, J=8.80 Hz), 7.43 (s, 1H), 7.37 (d, 1H, J=8.40 Hz), 7.56-7.62 (m, 1H), 12.62 (s, 1H).

MS (+ESI) m/z 398 (MH+).

Example 42

4-{2-[4-(5-Bromo-2-Chloro-phenoxy)-piperidin-1-yl]-2-oxo-ethylamino}-2H-pyridazin-3-one (42)

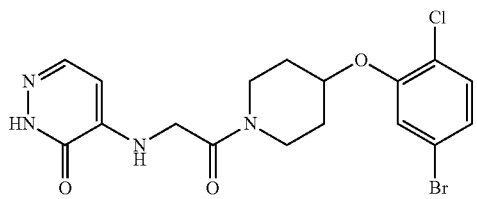 [SMILES: O=C(CNc1ccn[nH]c1=O)N1CCC(Oc2cc(Cl)ccc2Cl)CC1]

Compound 42 is prepared from intermediate 7a and intermediate 1f following synthesis method 2 (yield: 41%).

¹H NMR (DMSO-d₆) ppm: 1.54-1.77 (m, 2H), 1.84-2.02 (m, 2H), 3.37-3.52 (m, 2H), 3.60-3.79 (m, 2H), 3.98-4.06 (m, 2H), 4.81-4.90 (m, 1H), 6.10-6.15 (m 1H), 6.52-6.59 (m, 1H), 7.17 (d, 1H, J=8.40 Hz), 7.40 (d, 1H, J=8.80 Hz), 7.53 (s, 1H), 7.57-7.61 (m, 1H), 12.63 (s, 1H).

MS (+ESI) m/z 441 (MH+).

Example 43

4-{2-[4-(2-Bromo-4,5-difluoro-phenoxy)-piperidin-1-yl]-2-oxo-ethylamino}-2H-pyridazin-3-one (43)

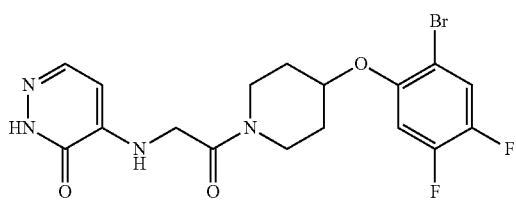 [SMILES: O=C(CNc1ccn[nH]c1=O)N1CCC(Oc2cc(F)c(F)cc2Br)CC1]

Compound 43 is prepared from intermediate 7a and from intermediate 1e following synthesis method 2 (yield: 36%)

¹H NMR (DMSO-d₆) ppm: 1.56-1.76 (m, 2H), 1.81-2.01 (m, 2H), 3.45-3.74 (m, 4H), 3.99-4.06 (m, 2H), 4.72-4.79 (m, 1H), 6.09-6.15 (m 1H), 6.51-6.58 (m, 1H), 7.48-7.56 (m, 1H), 7.62-7.56 (m, 1H), 7.80-7.87 (m, 1H), 12.62 (s, 1H).

MS (+ESI) m/z 444 (MH+).

Example 44

4-{2-[4-(3-trifluoromethyl-phenoxy)-piperidin-1-yl]-2-oxo-ethylamino}-2H-pyridazin-3-one (44)

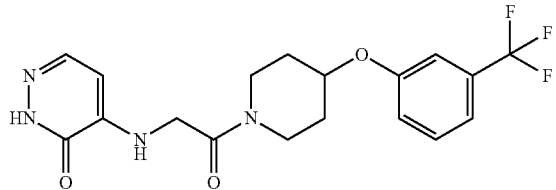 [SMILES: O=C(CNc1ccn[nH]c1=O)N1CCC(Oc2cccc(C(F)(F)F)c2)CC1]

Compound 44 is prepared from intermediate 7a and from 4-(3-trifluoromethyl-phenoxy)-piperidine (obtained following the method described for 1a) applying synthesis method 2 (yield: 36%).

RMN ¹H (DMSO-d₆) ppm: 1.50-1.73 (m, 2H), 1.88-2.05 (m, 2H), 3.33-3.44 (m, 2H), 3.66-3.77 (m, 1H), 3.83-3.92 (m, 1H), 3.99-4.05 (m, 2H), 4.74-4.84 (m, 1H), 6.13 (d 1H, J=4.4 Hz), 6.63-6.60 (m, 1H), 7.26-7.36 (m, 3H), 7.52 (t, 1H, J=7.20 Hz), 7.59 (d, 1H, J=4.4 Hz), 12.63 (s, 1H).

MS (+ESI) m/z 396 (MH+).

Example 45

4-{2-[4-(2-Chloro-5-trifluoromethyl-phenoxy)-piperidin-1-yl]-2-oxo-ethylamino}-2-(4,4,4-trifluoro-butyl)-2H-pyridazin-3-one (45)

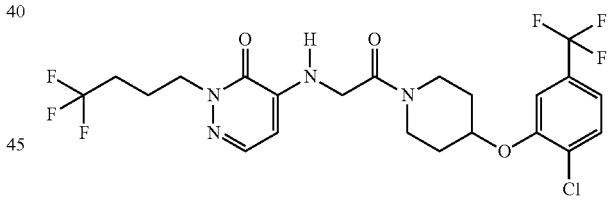

Compound 45 is prepared following synthesis method 6: 0.3 g (0.7 mmol) of intermediate 7b are placed in 10 mL DMF in the presence of 0.13 g (0.94 mmol) K₂CO₃ then 0.222 g (0.90 mmol) of 1,1,1-trifluoro-4-iodo-butane and agitated at 80° C. for 32 h. After concentrating to dryness, the residue is solubilized in water and extracted with AcOEt. The organic phases are washed in brine, dried over Na₂SO₄ then concentrated to dryness. The residue is purified by silica gel flash chromatography (gradient CH₂Cl₂-MeOH: 100:0 to 99:1 for 30 nm). 0.250 g of compound 45 are collected (yield: 67%).

TLC silica gel 60 F 254 Merck, CH₂Cl₂-MeOH: 97.5:2.5, Rf=0.70.

¹H NMR (DMSO-d₆) ppm: 1.56-1.80 (m, 2H), 1.87-2.06 (m, 4H), 2.22-2.38 (m, 2H), 3.40-3.57 (m, 2H), 3.62-3.80 (m, 2H), 4.02-4.08 (m, 2H), 4.12 (t, 2H, J=7.07 Hz), 4.94-5.05 (m, 1H), 6.16 (d, 1H, J=5.05 Hz), 6.65-6.71 (m, 1H), 7.34 (d, 1H, J=8.34 Hz), 7.62 (s, 1H), 7.65 (d, 1H, J=4.80 Hz), 7.70 (d, 1H, J=8.33 Hz)

MS (+ESI) m/z 541 (MH+).

Example 46

2-But-2-ynyl-4-{2-[4-(2-chloro-5-trifluoromethyl-phenoxy)-piperidin-1-yl]-2-oxo-ethylamino}-2H-pyridazin-3-one (46)

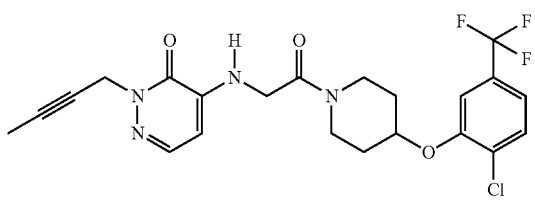 [SMILES: CC#CCn1nccc(NCC(=O)N2CCC(Oc3cc(C(F)(F)F)ccc3Cl)CC2)c1=O]

Compound 46 is prepared from intermediate 7b and from 1-bromo-but-2-yne following synthesis method 6 (yield: 9%).

TLC silica gel 60 F 254 Merck, CH$_2$Cl$_2$-MeOH: 95:5, Rf=0.65.

$^1$H NMR (DMSO-d$_6$) ppm: 1.57-1.69 (m, 1H), 1.69-1.80 (m, 4H), 1.85-2.05 (m, 2H), 3.40-3.55 (m, 2H), 3.62-3.79 (m, 2H), 4.05 (d, 2H, J=4.40 Hz), 4.77 (s, 2H), 4.94-5.02 (m, 1H), 6.15 (d, 1H, J=4.80 Hz), 6.67-6.72 (m, 1H), 7.34 (d, 1H, J=8.40 Hz), 7.60-7.66 (m, 2H), 7.70 (d, 1H, J=8.40 Hz).

MS (+ESI) m/z 483 (MH+)

Example 47

4-{2-[4-(2-Chloro-5-trifluoromethyl-phenoxy)-piperidin-1-yl]-2-oxo-ethylamino}-2-(4-methyl-pentyl)-2H-pyridazin-3-one (47)

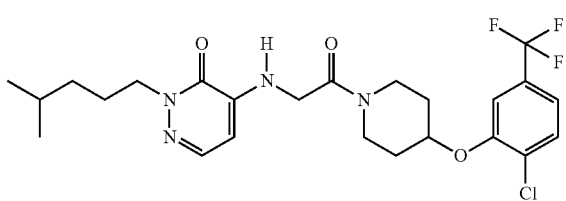 [SMILES: CC(C)CCCn1nccc(NCC(=O)N2CCC(Oc3cc(C(F)(F)F)ccc3Cl)CC2)c1=O]

Compound 47 is prepared from intermediate 7b and from 1-bromo-4-methyl-pentane following synthesis method 6 (yield: 33%).

TLC silica gel 60 F 254 Merck, CH$_2$Cl$_2$-MeOH: 95:5, Rf=0.70.

$^1$H NMR (DMSO-d$_6$) ppm: 0.84 (d, 6H, J=6.80 Hz), 1.11-1.19 (m, 2H), 1.47-1.79 (m, 5H), 1.86-2.04 (m, 2H), 3.41-3.55 (m, 2H), 3.62-3.79 (m, 2H), 3.96-4.07 (m, 4H), 4.93-5.02 (m, 1H), 6.14 (d, 1H, J=4.80 Hz), 6.65 (t, 1H, J=4.40 Hz), 7.34 (d, 1H, J=8.40 Hz), 7.60-7.64 (m, 2H), 7.69 (d, 1H, J=8.40 Hz).

MS (+ESI) m/z 515 (MH+)

Example 48

2-Benzyl-4-{2-oxo-2-[4-(2-trifluoromethyl-phenoxy)-piperidin-1-yl]-ethylamino}-2H-pyridazin-3-one (48)

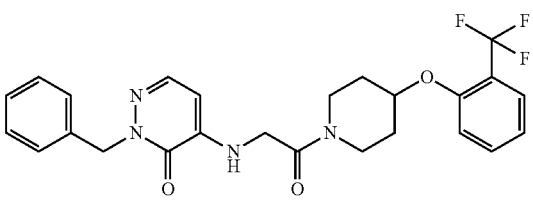 [SMILES: O=C(CNc1ccnn(Cc2ccccc2)c1=O)N1CCC(Oc2ccccc2C(F)(F)F)CC1]

Compound 48 is prepared from (2-benzyl-3-oxo-2,3-dihydro-pyridazin-4-ylamino)-acetic acid (obtained following the operating mode for 4e using benzyl bromide to alkylate nitrogen 2 of pyridazinone) and from intermediate 1a in base form, following synthesis method 2 (yield: 30%).

TLC silica gel 60 F 254 Merck, CH$_2$Cl$_2$—AcOEt: 50:50, Rf=0.41.

mp=80° C.

RMN $^1$H (DMSO-d$_6$) ppm: 1.58-1.80 (m, 2H), 1.83-2.05 (m, 2H), 3.42-3.52 (m, 1H), 3.53-3.67 (m, 3H), 4.05 (d, 2H, J=4.55 Hz), 4.87-4.94 (m, 1H), 5.53 (s, 2H), 6.17 (d, 1H, J=5.05 Hz), 6.66-6.72 (m, 1H), 7.09 (t, 1H, J=7.70 Hz), 7.23-7.39 (m, 6H), 7.58-7.67 (m, 3H).

MS (+ESI) m/z 487 (MH+)

Example 49

2-Isopropyl-4-{2-oxo-2-[4-(2-trifluoromethyl-phenoxy)-piperidin-1-yl]-ethylamino}-2H-pyridazin-3-one (49)

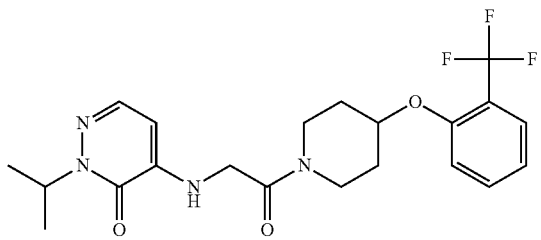 [SMILES: CC(C)n1nccc(NCC(=O)N2CCC(Oc3ccccc3C(F)(F)F)CC2)c1=O]

Compound 49 is prepared from (2-isopropyl-3-oxo-2,3-dihydro-pyridazin-4-ylamino)-acetic acid (obtained following the operating mode for 4e using 2-iodo-propane to alkylate nitrogen 2 of pyridazinone) and from intermediate 1a in base form, following synthesis method 2 (yield: 69%).

TLC silica gel 60 F 254 Merck, CH$_2$Cl$_2$-MeOH—NH$_4$OH: 95:4.5:0.5, Rf=0.40.

mp=180° C.

$^1$H NMR (CDCl$_3$) ppm: 1.30 (d, 6H, J=6.57 Hz), 1.81-1.96 (m, 2H), 1.97-2.12 (m, 2H), 3.37-3.51 (m, 2H), 3.56-3.67 (m, 1H), 3.77-3.82 (m, 2H), 4.12-4.20 (m, 1H), 4.82 (s br., 1H), 5.24 (spt, 1H, J=6.56 Hz), 5.54-5.63 (m, 2H), 6.99 (d, 1H, J=8.33 Hz), 7.04 (t, 1H, J=7.57 Hz), 7.45-7.53 (m, 2H), 7.61 (d, 1H, J=7.57 Hz).

MS (+ESI) m/z 439 (MH+)

Example 50

2-Butyl-4-{2-[4-(2-chloro-phenoxy)-piperidin-1-yl]-2-oxo-ethylamino}-2H-pyridazin-3-one (50)

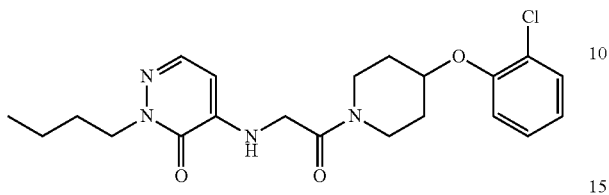

Compound 50 is prepared from (2-butyl-3-oxo-2,3-dihydro-pyridazin-4-ylamino)-acetic acid (obtained following the operating mode for 4e using 1-iodo-butane to alkylate nitrogen 2 of pyridazinone) and from intermediate 1g in base form, following synthesis method 2 (yield: 34%).

TLC silica gel 60 F 254 Merck, $CH_2Cl_2$-MeOH—$NH_4OH$: 90:9:1, Rf=0.75.

mp=82° C.

$^1$H NMR ($CDCl_3$) ppm: 0.95 (t, 3H, J=7.32 Hz), 1.38 (m, 2H), 1.79 (qt, 2H, J=7.58 Hz), 1.83-2.05 (m, 4H), 3.39-3.49 (m, 1H), 3.59-3.78 (m, 2H), 3.89 (d, 2H, J=4.54 Hz), 3.96-4.05 (m, 1H), 4.15 (t, 2H, J=7.32 Hz), 4.64-4.70 (m, 1H), 5.87 (d, 1H, J=4.80 Hz), 6.66-6.73 (m, 1H), 6.91-6.99 (m, 2H), 7.21 (t, 1H, J=7.83 Hz), 7.39 (d, 1H, J=7.58 Hz), 7.55 (d, 1H, J=4.80 Hz).

MS (+ESI) m/z 419 (MH+)

Example 51

4-{2-[4-(2-Chloro-5-trifluoromethyl-phenoxy)-piperidin-1-yl]-2-oxo-ethylamino}-5-methoxy-2-methyl-2H-pyridazin-3-one (51)

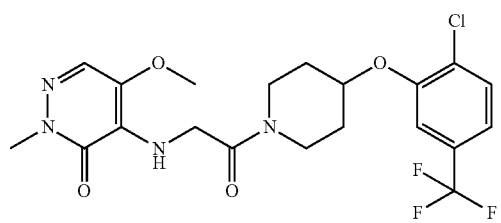 [SMILES: COc1cnn(C)c(=O)c1NCC(=O)N1CCC(Oc2cc(C(F)(F)F)ccc2Cl)CC1]

Compound 51 is prepared from intermediate 1c in base form and from intermediate 4f, following synthesis method 2 (yield: 21%).

TLC silica gel 60 F 254 Merck, AcOEt: 100, Rf=0.26.

mp=60° C.

$^1$H NMR (DMSO-$d_6$) ppm: 1.56-1.77 (m, 2H), 1.84-2.03 (m, 2H), 3.34-3.40 (m, 1H), 3.41-3.50 (m, 1H), 3.53-3.63 (m, 4H), 3.68-3.79 (m, 4H), 4.33 (d, 2H, J=5.68 Hz), 4.94-5.01 (m, 1H), 6.04 (t, 1H, J=5.68 Hz), 7.33 (dd, 1H, J=8.00 Hz and J=0.8 Hz), 7.61 (d, 1H, J=0.8 Hz), 7.69 (d, 1H, J=8.00 Hz), 7.85 (s, 1H).

MS (+ESI) m/z 475 (MH+).

Example 52

4-(2-Chloro-5-trifluoromethyl-phenoxy)-piperidine-1-carboxylic acid (2-methyl-3-oxo-2,3-dihydro-pyridazin-4-yl)-amide (52)

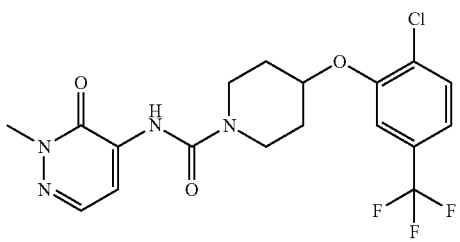 [SMILES: Cn1nccc(NC(=O)N2CCC(Oc3cc(C(F)(F)F)ccc3Cl)CC2)c1=O]

Compound 52 is prepared following synthesis method 7: intermediate 4c (0.5 g, 4 mmol) is placed in 84 ml THF under nitrogen, 1 g (4.8 mmol) of 4-nitrophenylchloroformiate are poured dropwise then the reaction medium is agitated at ambient temperature for 2 h. 1.7 g (6 mmol) of intermediate 1c and 2.23 ml (16 mmol) of triethylamine are added then the reaction medium is heated to 50° C. for 24 h. After concentrating to dryness, the residue obtained is solubilized in water and extracted with dichloromethane. After drying the organic phases and concentrating to dryness, the residue is purified by silica gel flash chromatography (gradient $CH_2Cl_2$—AcOEt: 100:0 to 85:15 in 30 nm). 0.695 g of white solid are isolated (yield: 40%).

TLC silica gel 60 F 254 Merck, $CH_2Cl_2$—AcOEt: 50:50, Rf=0.47.

mp=148° C.

$^1$H NMR (DMSO-$d_6$) ppm: 1.65-1.77 (m, 2H), 1.93-2.03 (m, 2H), 3.42-3.51 (m, 2H), 3.62-3.73 (m, 5H), 4.92-5.00 (m, 1H), 7.34 (d, 1H, J=8.33 Hz), 7.61 (s, 1H), 7.67-7.73 (m, 2H), 7.81 (d, 1H, J=4.80 Hz), 8.49 (s, 1H).

MS (+ESI) m/z 431 (MH+)

Example 53

4-(2-Chloro-5-fluoro-phenoxy)-piperidine-1-carboxylic acid (2-methyl-3-oxo-2,3-dihydro-pyridazin-4-yl)-amide (53)

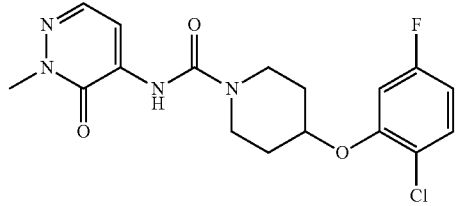 [SMILES: Cn1nccc(NC(=O)N2CCC(Oc3cc(F)ccc3Cl)CC2)c1=O]

Compound 53 is prepared from intermediate 4c and from intermediate 1d in base form, following synthesis method 7 (yield: 25%).

TLC silica gel 60 F 254 Merck, $CH_2Cl_2$-MeOH: 97.5-2.5, Rf=0.35.

mp=116° C.

$^1$H NMR (DMSO-$d_6$) ppm: 1.63-1.75 (m, 2H), 1.92-2.02 (m, 2H), 3.39-3.48 (m, 2H), 3.61-3.72 (m, 5H), 4.74-4.82 (m, 1H), 6.83 (td, 1H, J=8.40 Hz and J=2.80 Hz), 7.26 (dd, 1H, J=10.80 Hz and J=2.80 Hz), 7.47 (dd, 1H, J=8.80 Hz and J=6.00 Hz), 7.70 (d, 1H, J=5.20 Hz), 7.80 (d, 1H, J=4.80 Hz), 8.49 (s, 1H).

MS (+ESI) m/z 381 (MH+)

Example 54

4-(2-fluoro-5-trifluoromethyl-phenoxy)-piperidine-1-carboxylic acid (2-methyl-3-oxo-2,3-dihydro-pyridazin-4-yl)-amide (54)

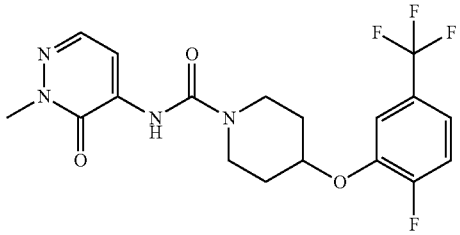 [SMILES: Cn1nccc(NC(=O)N2CCC(Oc3cc(C(F)(F)F)ccc3F)CC2)c1=O]

Compound 54 is prepared from intermediate 4c and from 4-(2-fluoro-5-trifluoromethyl-phenoxy)-piperidine (obtained following the method described for intermediate 1a), applying synthesis method 7 (yield: 41%).

TLC silica gel 60 F 254 Merck, CH$_2$Cl$_2$-MeOH: 97.5:2.5, Rf=0.35.

mp=102° C.

$^1$H NMR (DMSO-d$_6$) ppm: 1.60-1.72 (m, 2H), 1.95-2.04 (m, 2H), 3.32-3.41 (m, 2H), 3.67-3.78 (m, 5H), 4.79-4.88 (m, 1H), 7.34-7.40 (m, 1H), 7.44 (m, 1H), 7.65 (dd, 1H, J=7.60 Hz and J=1.60 Hz), 7.70 (d, 1H, J=4.80 Hz), 7.80 (d, 1H, J=4.80 Hz), 8.49 (s, 1H).

MS (+ESI) m/z 415 (MH+)

Example 55

4-(2,5-dimethyl-phenoxy)-piperidine-1-carboxylic acid (2-methyl-3-oxo-2,3-dihydro-pyridazin-4-yl)-amide (55)

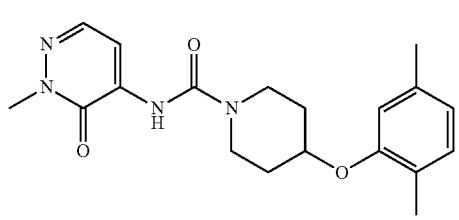 [SMILES: Cc1ccc(C)c(OC2CCN(C(=O)Nc3ccnn(C)c3=O)CC2)c1]

Compound 55 is prepared from intermediate 4c and from 4-(2,5-dimethyl-phenoxy)-piperidine (obtained following the method described for intermediate 1a), applying synthesis method 7 (yield: 43%).

TLC silica gel 60 F 254 Merck, CH$_2$Cl$_2$-MeOH: 97.5:2.5, Rf=0.35.

mp=108° C.

$^1$H NMR (DMSO-d$_6$) ppm: 1.61-1.72 (m, 2H), 1.89-1.99 (m, 2H), 2.10 (s, 3H), 2.25 (s, 3H), 3.37-3.46 (m, 2H), 3.61-3.71 (m, 5H), 4.57-4.64 (m, 1H), 6.64 (d, 1H, J=7.20), 6.83 (s, 1H), 7.00 (d, 1H, J=7.60 Hz), 7.70 (d, 1H, J=4.80 Hz), 7.80 (d, 1H, J=4.80 Hz), 8.47 (s, 1H).

MS (+ESI) m/z 357 (MH+

Example 56

4-(2-chloro-5-methyl-phenoxy)-piperidine-1-carboxylic acid (2-methyl-3-oxo-2,3-dihydro-pyridazin-4-yl)-amide (56)

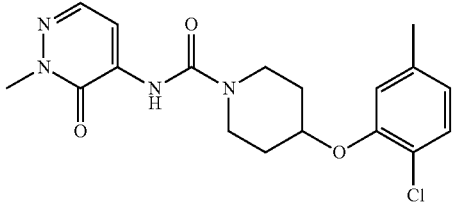 [SMILES: Cc1ccc(Cl)c(OC2CCN(C(=O)Nc3ccnn(C)c3=O)CC2)c1]

Compound 56 is prepared from intermediate 4c and from 4-(2-chloro-5-methyl-phenoxy)-piperidine (obtained following the method described for intermediate 1a) applying synthesis method 7 (yield: 28%).

TLC silica gel 60 F 254 Merck, CH$_2$Cl$_2$-MeOH: 97.5:2.5, Rf=0.35.

mp=133° C.

$^1$H NMR (DMSO-d$_6$) ppm: 1.63-1.74 (m, 2H), 1.91-2.00 (m, 2H), 2.29 (s, 3H), 3.39-3.48 (m, 2H), 3.62-3.72 (m, 5H), 4.67-4.74 (m, 1H), 6.78 (dd, 1H, J=8.00 Hz and J=1.20 Hz), 7.09 (s, 1H), 7.28 (d, 1H, J=8.00 Hz), 7.70 (d, 1H, J=4.80 Hz), 7.80 (d, 1H, J=4.80 Hz), 8.48 (s, 1H).

MS (+ESI) m/z 377 (MH+)

Example 57

4-(2-methyl-5-isopropyl-phenoxy)-pipéridine-1-carboxylic acid (2-methyl-3-oxo-2,3-dihydro-pyridazin-4-yl)-amide (57)

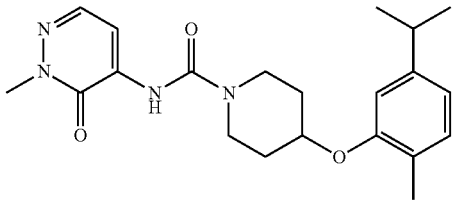 [SMILES: Cc1ccc(C(C)C)cc1OC1CCN(C(=O)Nc2ccnn(C)c2=O)CC1]

Compound 57 is prepared from intermediate 4c and from 4-(5-isopropyl-2-methyl-phenoxy)-piperidine (obtained following the method described for intermediate 1a,) applying synthesis method 7 (yield: 51%).

TLC silica gel 60 F 254 Merck, CH$_2$Cl$_2$-MeOH: 97.5:2.5, Rf=0.25.

mp=104° C.

$^1$H NMR (DMSO-d$_6$) ppm: 1.17 (d, 6H, J=6.80 Hz), 1.63-1.73 (m, 2H), 1.89-1.99 (m, 2H), 2.11 (s, 3H), 2.76-2.88 (m, 1H), 3.40-3.49 (m, 2H), 3.61-3.72 (m, 5H), 4.61-4.68 (m, 1H), 6.70 (dd, 1H, J=7.60 Hz and J=0.80 Hz), 6.85 (s, 1H), 7.03 (d, 1H, J=7.60 Hz), 7.70 (d, 1H, J=4.80 Hz), 7.80 (d, 1H, J=4.80 Hz), 8.46 (s, 1H).

MS (+ESI) m/z 385 (MH+)

Example 58

4-(5-trifluoromethyl-phenoxy)-piperidine-1-carboxylic acid (2-methyl-3-oxo-2,3-dihydro-pyridazin-4-yl)-amide (58)

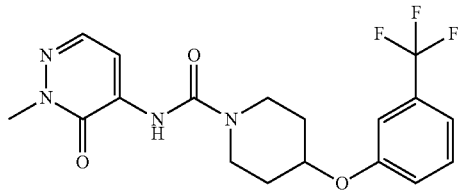 [SMILES: Cn1nccc(NC(=O)N2CCC(Oc3cccc(C(F)(F)F)c3)CC2)c1=O]

Compound 58 is prepared from intermediate 4c and from 4-(3-trifluoromethyl-phenoxy)-piperidine (obtained following the method described for intermediate 1a), applying synthesis method 7 (yield: 36%).

TLC silica gel 60 F 254 Merck, CH$_2$Cl$_2$-MeOH: 97.5:2.5, Rf=0.45.

mp=101° C.

$^1$H NMR (DMSO-d$_6$) ppm: 1.58-1.70 (m, 2H), 1.94-2.04 (m, 2H), 3.33-3.41 (m, 2H), 3.67-3.78 (m, 5H), 4.72-4.80 (m, 1H), 7.25-7.34 (m, 3H), 7.49-7.55 (m, 1H), 7.70 (d, 1H, J=5.20 Hz), 7.80 (d, 1H, J=4.80 Hz), 8.48 (s, 1H).

MS (+ESI) m/z 397 (MH+)

Example 59

4-(2-methyl-phenoxy)-piperidine-1-carboxylic acid (2-methyl-3-oxo-2,3-dihydro-pyridazin-4-yl)-amide (59)

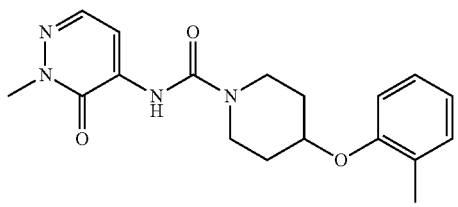 [SMILES: Cc1ccccc1OC1CCN(C(=O)Nc2ccnn(C)c2=O)CC1]

Compound 59 is prepared from intermediate 4c and from 4-o-tolyloxy-piperidine (obtained following the method described for intermediate 1a), applying synthesis method 7 (yield: 50%).

TLC silica gel 60 F 254 Merck, CH$_2$Cl$_2$-MeOH: 97.5:2.5, Rf=0.25.

mp=124° C.

$^1$H NMR (DMSO-d$_6$) ppm: 1.62-1.73 (m, 2H), 1.89-2.00 (m, 2H), 2.16 (s, 3H), 3.38-3.47 (m, 2H), 3.61-3.71 (m, 5H), 4.58-4.67 (m, 1H), 6.83 (t, 1H, J=7.60 Hz), 7.00 (d, 1H, J=8.00 Hz), 7.11-7.16 (m, 2H), 7.70 (d, 1H, J=4.80 Hz), 7.80 (d, 1H, J=4.80 Hz), 8.47 (s, 1H).

MS (+ESI) m/z 343 (MH+)

Example 60

4-(4-fluoro-5-trifluoromethyl-phenoxy)-piperidine-1-carboxylic acid (2-methyl-3-oxo-2,3-dihydro-pyridazin-4-yl)-amide (60)

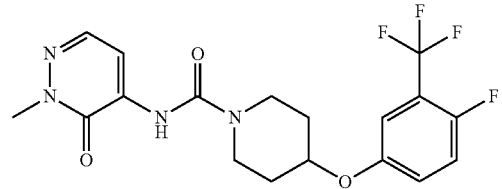 [SMILES: Cn1nccc(NC(=O)N2CCC(Oc3ccc(F)c(C(F)(F)F)c3)CC2)c1=O]

Compound 60 is prepared from intermediate 4c and from 4-(4-fluoro-3-trifluoromethyl-phenoxy)-piperidine (obtained following the method described for intermediate 1a), applying synthesis method 7 (yield: 51%).

TLC silica gel 60 F 254 Merck, CH$_2$Cl$_2$-MeOH: 97.5:2.5, Rf=0.25.

mp=127° C.

$^1$H NMR (DMSO-d$_6$) ppm: 1.56-1.69 (m, 2H), 1.91-2.02 (m, 2H), 3.30-3.40 (m, 2H), 3.66-3.78 (m, 5H), 4.67-4.74 (m, 1H), 7.30-7.48 (m, 3H), 7.70 (d, 1H, J=4.80 Hz), 7.80 (d, 1H, J=4.80 Hz), 8.48 (s, 1H).

MS (+ESI) m/z 415 (MH+)

Example 61

4-(5-fluoro-2-trifluoromethyl-phenoxy)-piperidine-1-carboxylic acid (2-methyl-3-oxo-2,3-dihydro-pyridazin-4-yl)-amide (61)

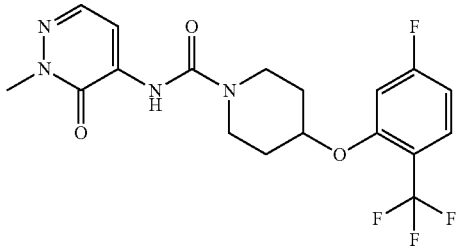 [SMILES: Cn1nccc(NC(=O)N2CCC(Oc3cc(F)ccc3C(F)(F)F)CC2)c1=O]

Compound 61 is prepared from intermediate 4c and from intermediate 1b in base form, following synthesis method 7 (yield: 43%).

TLC silica gel 60 F 254 Merck, CH$_2$Cl$_2$-MeOH: 97.5:2.5, Rf=0.45.

mp=145° C.

$^1$H NMR (DMSO-d$_6$) ppm: 1.65-1.76 (m, 2H), 1.92-2.02 (m, 2H), 3.43-3.52 (m, 2H), 3.53-3.62 (m, 2H), 3.70 (s, 3H), 4.86-4.93 (m, 1H), 6.93 (td, 1H, J=8.40 Hz and J=2.00 Hz), 7.35 (dd, 1H, J=11.20 Hz and J=1.60 Hz), 7.66-7.72 (m, 2H), 7.80 (d, 1H, J=5.20 Hz), 8.50 (s, 1H).

MS (+ESI) m/z 415 (MH+)

Example 62

4-(2,5-dichloro-phenoxy)-piperidine-1-carboxylic acid (2-methyl-3-oxo-2,3-dihydro-pyridazin-4-yl)-amide (62)

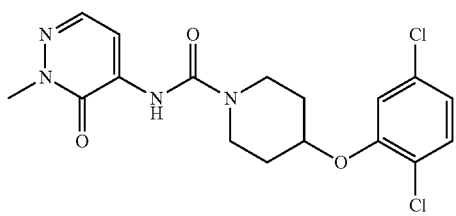 [SMILES: Cn1nccc(NC(=O)N2CCC(Oc3cc(Cl)ccc3Cl)CC2)c1=O]

Compound 62 is prepared from intermediate 4c and from intermediate 1j in base form, following synthesis method 7 (yield: 34%).

TLC silica gel 60 F 254 Merck, CH$_2$Cl$_2$-MeOH: 97.5-2.5, Rf=0.45.

mp=125° C.

$^1$H NMR (DMSO-d$_6$) ppm: 1.62-1.74 (m, 2H), 1.91-2.01 (m, 2H), 3.38-3.48 (m, 2H), 3.61-3.72 (m, 5H), 4.78-4.86 (m, 1H), 7.04 (dd, 1H, J=8.40 Hz and J=2.40 Hz), 7.42 (d, 1H, J=2.00 Hz), 7.47 (d, 1H, J=8.40 Hz), 7.70 (d, 1H, J=4.80 Hz), 7.80 (d, 1H, J=4.80 Hz), 8.50 (s, 1H).

MS (+ESI) m/z 397 (MH+)

Example 63

4-(2-chloro-5-bromo-phenoxy)-piperidine-1-carboxylic acid (2-methyl-3-oxo-2,3-dihydro-pyridazin-4-yl)-amide (63)

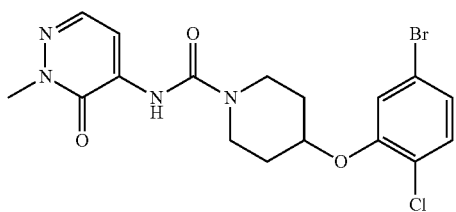 [SMILES: Cn1nccc(NC(=O)N2CCC(Oc3cc(Br)ccc3Cl)CC2)c1=O]

Compound 63 is prepared from intermediate 4c and from intermediate 1f in base form, following synthesis method 7 (yield: 44%).

TLC silica gel 60 F 254 Merck, CH$_2$Cl$_2$-MeOH: 97.5-2.5, Rf=0.45.

mp=124° C.

$^1$H NMR (DMSO-d$_6$) ppm: 1.62-1.73 (m, 2H), 1.90-2.01 (m, 2H), 3.38-3.48 (m, 2H), 3.61-3.72 (m, 5H), 4.79-4.87 (m, 1H), 7.16 (dd, 1H, J=8.40 Hz and J=2.00 Hz), 7.40 (d, 1H, J=8.40 Hz), 7.52 (d, 1H, J=2.00 Hz), 7.70 (d, 1H, J=4.80 Hz), 7.80 (d, 1H, J=4.80 Hz), 8.50 (s, 1H).

MS (+ESI) m/z 441 (MH+)

Example 64

4-(2-chloro-phenoxy)-piperidine-1-carboxylic acid (2-methyl-3-oxo-2,3-dihydro-pyridazin-4-yl)-amide (64)

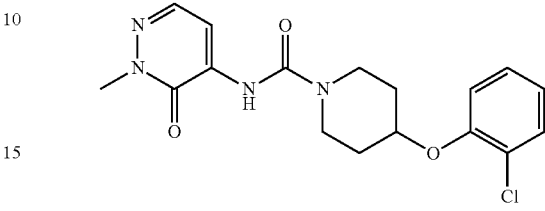

Compound 64 is prepared from intermediate 4c and from intermediate 1g in base form, following synthesis method 7 (yield: 45%).

TLC silica gel 60 F 254 Merck, CH$_2$Cl$_2$-MeOH: 97.5-2.5, Rf=0.40.

mp=124° C.

$^1$H NMR (DMSO-d$_6$) ppm: 1.64-1.74 (m, 2H), 1.91-2.01 (m, 2H), 3.39-3.48 (m, 2H), 3.61-3.73 (m, 5H), 4.70-4.77 (m, 1H), 6.97 (td, 1H, J=8.00 Hz and J=1.60 Hz), 7.24-7.33 (m, 2H), 7.44 (dd, 1H, J=8.00 Hz and J=1.60 Hz), 7.70 (d, 1H, J=4.80 Hz), 7.80 (d, 1H, J=4.80 Hz), 8.49 (s, 1H).

MS (+ESI) m/z 363 (MH+)

Example 65

4-(3,4-dichloro-phenoxy)-piperidine-1-carboxylic acid (2-methyl-3-oxo-2,3-dihydro-pyridazin-4-yl)-amide (65)

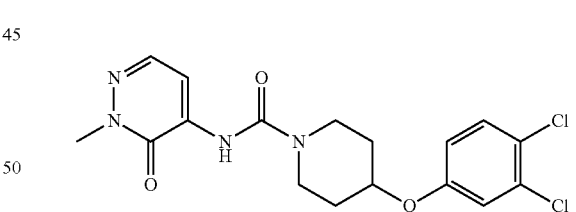

Compound 65 is prepared from intermediate 4c and from intermediate 1h in base form, following synthesis method 7 (yield: 49%).

TLC silica gel 60 F 254 Merck, CH$_2$Cl$_2$-MeOH: 97.5-2.5, Rf=0.40.

mp=154° C.

$^1$H NMR (DMSO-d$_6$) ppm: 1.55-1.67 (m, 2H), 1.91-2.02 (m, 2H), 3.29-3.39 (m, 2H), 3.66-3.78 (m, 5H), 4.64-4.72 (m, 1H), 7.02 (dd, 1H, J=8.80 Hz and J=2.80 Hz), 7.33 (d, 1H, J=2.80 Hz), 7.52 (d, 1H, J=8.80 Hz), 7.70 (d, 1H, J=4.80 Hz), 7.80 (d, 1H, J=4.80 Hz), 8.48 (s, 1H).

MS (+ESI) m/z 397 (MH+)

Example 66

4-(2,4-dichloro-phenoxy)-piperidine-1-carboxylic acid (2-methyl-3-oxo-2,3-dihydro-pyridazin-4-yl)-amide (66)

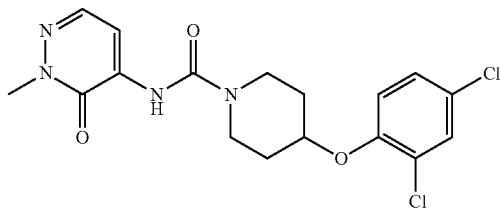 [SMILES: Cn1nccc(NC(=O)N2CCC(Oc3ccc(Cl)cc3Cl)CC2)c1=O]

Compound 66 is prepared from intermediate 4c and from intermediate 1i in base form, following synthesis method 7 (yield: 43%).

TLC silica gel 60 F 254 Merck, CH$_2$Cl$_2$-MeOH: 97.5:2.5, Rf=0.35.

mp=140° C.

$^1$H NMR (DMSO-d$_6$) ppm: 1.63-1.75 (m, 2H), 1.90-2.01 (m, 2H), 3.38-3.48 (m, 2H), 3.60-3.72 (m, 5H), 4.70-4.78 (m, 1H), 7.30 (d, 1H, J=8.80 Hz), 7.37 (dd, 1H, J=8.80 Hz and J=2.40 Hz), 7.59 (d, 1H, J=2.40 Hz), 7.70 (d, 1H, J=4.80 Hz), 7.80 (d, 1H, J=4.80 Hz), 8.49 (s, 1H).

MS (+ESI) m/z 397 (MH+)

Example 67

4-(3-fluoro-5-trifluoromethyl-phenoxy)-piperidine-1-carboxylic acid (2-methyl-3-oxo-2,3-dihydro-pyridazin-4-yl)-amide (67)

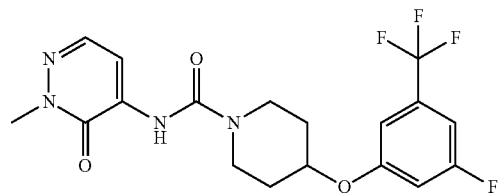 [SMILES: Cn1nccc(NC(=O)N2CCC(Oc3cc(F)cc(C(F)(F)F)c3)CC2)c1=O]

Compound 67 is prepared from intermediate 4c and from 4-(3-fluoro-5-trifluoromethyl-phenoxy)-piperidine (obtained following the method described for intermediate 1a), applying synthesis method 7 (yield: 42%).

TLC silica gel 60 F 254 Merck, CH$_2$Cl$_2$-MeOH: 97.5:2.5, Rf=0.35.

mp=115° C.

$^1$H NMR (DMSO-d$_6$) ppm: 1.58-1.69 (m, 2H), 1.94-2.05 (m, 2H), 3.39-3.31 (m, 2H), 3.66-3.79 (m, 5H), 4.76-4.84 (m, 1H), 7.16-7.24 (m, 2H), 7.30 (d, 1H, J=11.20 Hz), 7.70 (d, 1H, J=4.80 Hz), 7.80 (d, 1H, J=4.80 Hz), 8.49 (s, 1H).

MS (+ESI) m/z 415 (MH+)

Example 68

4-(5-fluoro-2-methyl-phenoxy)-piperidine-1-carboxylic acid (2-methyl-3-oxo-2,3-dihydro-pyridazin-4-yl)-amide (68)

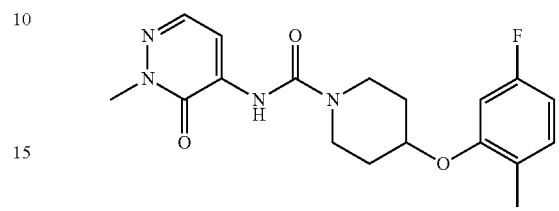

Compound 68 is prepared from intermediate 4c and from 4-(5-fluoro-2-methyl-phenoxy)-piperidine (obtained following the method described for intermediate 1a), applying synthesis method 7 (yield: 46%).

TLC silica gel 60 F 254 Merck, CH$_2$Cl$_2$-MeOH: 97.5:2.5, Rf=0.35.

mp=142° C.

$^1$H NMR (DMSO-d$_6$) ppm: 1.61-1.72 (m, 2H), 1.90-2.00 (m, 2H), 2.11 (s, 3H), 3.38-3.47 (m, 2H), 3.61-3.72 (m, 5H), 4.63-4.71 (m, 1H), 6.65 (td, 1H, J=8.40 Hz and J=2.40 Hz), 6.95 (dd, 1H, J=11.60 Hz and J=2.40 Hz), 7.15 (t, 1H, J=7.60 Hz), 7.70 (d, 1H, J=5.20 Hz), 7.80 (d, 1H, J=4.80 Hz), 8.48 (s, 1H).

MS (+ESI) m/z 361 (MH+)

Example 69

4-(2,5-difluoro-phenoxy)-piperidine-1-carboxylic acid (2-methyl-3-oxo-2,3-dihydro-pyridazin-4-yl)-amide (69)

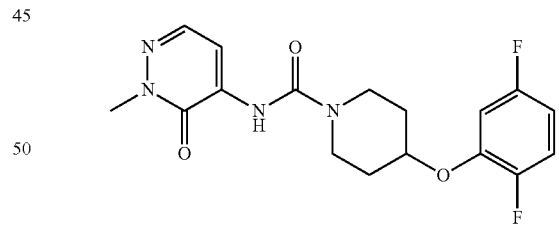

Compound 69 is prepared from intermediate 4c and from intermediate 1k in base form, following synthesis method 7 (yield: 51%).

TLC silica gel 60 F 254 Merck, CH$_2$Cl$_2$-MeOH: 97.5:2.5, Rf=0.30.

mp=138° C.

$^1$H NMR (DMSO-d$_6$) ppm: 1.59-1.70 (m, 2H), 1.94-2.04 (m, 2H), 3.31-3.38 (m, 2H), 3.67-3.78 (m, 5H), 4.64-4.72 (m, 1H), 6.74-6.82 (m, 1H), 7.22-7.30 (m, 2H), 7.70 (d, 1H, J=5.20 Hz), 7.80 (d, 1H, J=4.80 Hz), 8.49 (s, 1H).

MS (+ESI) m/z 365 (MH+)

Example 70

4-(2,4,5-trichloro-phenoxy)-piperidine-1-carboxylic acid (2-methyl-3-oxo-2,3-dihydro-pyridazin-4-yl)-amide (70)

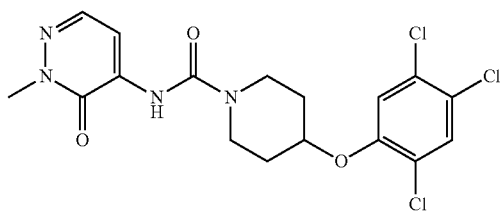 [SMILES: Cn1nccc(NC(=O)N2CCC(Oc3cc(Cl)c(Cl)cc3Cl)CC2)c1=O]

Compound 70 is prepared from intermediate 4c and from 4-(2,4,5-trichloro-phénoxy)-piperidine (obtained following the method described for intermediate 1a) applying synthesis method 7 (yield: 46%).

TLC silica gel 60 F 254 Merck, $CH_2Cl_2$-MeOH: 97.5:2.5, Rf=0.40.

mp=154° C.

$^1$H NMR (DMSO-$d_6$) ppm: 1.62-1.73 (m, 2H), 1.91-2.02 (m, 2H), 3.38-3.48 (m, 2H), 3.60-3.72 (m, 5H), 4.80-4.89 (m, 1H), 6.64 (s, 1H), 7.70 (d, 1H, J=4.80 Hz), 7.80 (d, 1H, J=4.80 Hz), 7.83 (s, 1H), 8.50 (s, 1H).

MS (+ESI) m/z 431 (MH+)

Example 71

4-(2-bromo-4,5-difluoro-phenoxy)-piperidine-1-carboxylic acid (2-methyl-3-oxo-2,3-dihydro-pyridazin-4-yl)-amide (71)

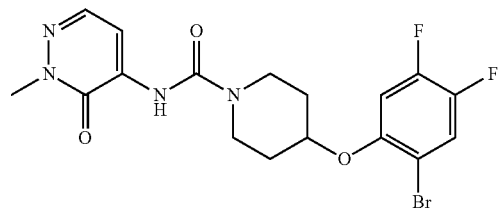 [SMILES: Cn1nccc(NC(=O)N2CCC(Oc3cc(F)c(F)cc3Br)CC2)c1=O]

Compound 71 is prepared from intermediate 4c and from intermediate 1e in base form, following synthesis method 7 (yield: 47%).

TLC silica gel 60 F 254 Merck, $CH_2Cl_2$-MeOH: 97.5:2.5, Rf=0.40.

mp=143° C.

$^1$H NMR (DMSO-$d_6$) ppm: 1.62-1.75 (m, 2H), 1.88-1.99 (m, 2H), 3.41-3.50 (m, 2H), 3.57-3.67 (m, 2H), 3.70 (s, 3H), 4.70-4.78 (m, 1H), 7.52 (dd, 1H, J=11.60 Hz and J=7.20 Hz), 7.70 (d, 1H, J=5.20 Hz), 7.80 (d, 1H, J=4.80 Hz), 7.84 (dd, 1H, J=9.60 Hz and J=8.8 Hz), 8.50 (s, 1H).

MS (+ESI) m/z 445 (MH+)

Example 72

4-(2-Chloro-5-trifluoromethyl-phenoxy)-piperidine-1-carboxylic acid (3-oxo-2,3-dihydro-pyridazin-4-yl)-amide (72)

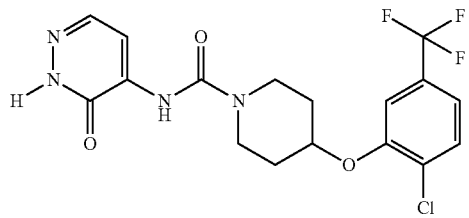 [SMILES: O=C(Nc1ccn[nH]c1=O)N1CCC(Oc2cc(C(F)(F)F)ccc2Cl)CC1]

Compound 72 is prepared from 4-amino-2-benzyloxymethyl-2H-pyridazin-3-one (prepared following the method described for intermediate 4c) and from intermediate 1c, following synthesis method 7 (yield: 49%). The compound obtained is then placed in EtOH in the presence of Pd/C under 3 bar of $H_2$ for 11 h. After filtering and concentrating to dryness, compound 72 is obtained (yield: 61%).

TLC silica gel 60 F 254 Merck, $CH_2Cl_2$-MeOH: 95:5, Rf=0.38.

mp=158° C.

$^1$H NMR (DMSO-$d_6$) ppm: 1.64-1.76 (m, 2H), 1.92-2.02 (m, 2H), 3.39-3.51 (m, 2H), 3.60-3.72 (m, 2H), 4.90-4.99 (m, 1H), 7.33 (dd, 1H, J=8.0 Hz and J=1.2 Hz), 7.60 (d, 1H, J=1.2 Hz), 7.67-7.71 (m, 2H), 7.79 (d, 1H, J=4.8 Hz), 8.42 (s, 1H), 13.20 (s, 1H).

MS (+ESI) m/z 417 (MH+)

Example 73

4-(2-Chloro-5-trifluoromethyl-phenoxy)-piperidine-1-carboxylic acid (1-methyl-6-oxo-1,6-dihydro-pyridazin-4-yl)-amide (73)

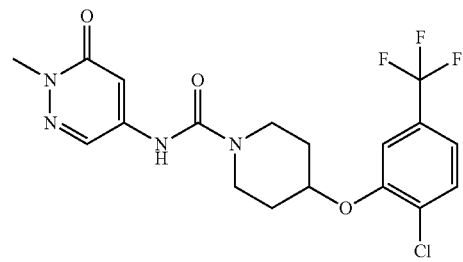 [SMILES: Cn1ncc(NC(=O)N2CCC(Oc3cc(C(F)(F)F)ccc3Cl)CC2)cc1=O]

Compound 73 is prepared from intermediate 6b and from intermediate 1c following synthesis method 7 (yield: 36%).

TLC silica gel 60 F 254 Merck, $CH_2Cl_2$-MeOH: 90:10, Rf=0.45.

mp=136° C.

$^1$H NMR (DMSO-$d_6$) ppm: 1.62-1.73 (m, 2H), 1.91-2.01 (m, 2H), 3.41-3.50 (m, 2H), 3.55 (s, 3H), 3.65-3.75 (m, 2H), 4.90-4.99 (m, 1H), 6.97 (d, 1H, J=2.00 Hz), 7.34 (d, 1H, J=8.40 Hz), 7.61 (s, 1H), 7.70 (d, 1H, J=8.40 Hz), 8.00 (d, 1H, J=2.00 Hz), 9.07 (s, 1H).

MS (+ESI) m/z 431 (MH+)

Example 74

4-(2-Chloro-5-trifluoromethyl-phenoxy)-piperidine-1-carboxylic acid (1-methyl-6-oxo-1,6-dihydro-pyridazin-3-yl)-amide (74)

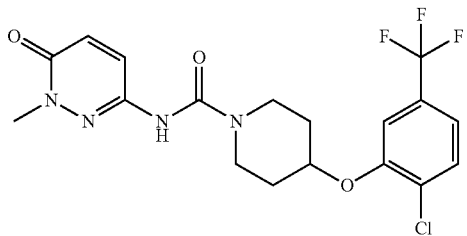 [SMILES: Cn1nc(NC(=O)N2CCC(Oc3cc(C(F)(F)F)ccc3Cl)CC2)ccc1=O]

Compound 74 is prepared from intermediate 6a and intermediate 1c following synthesis method 7 (yield: 49%).

TLC silica gel 60 F 254 Merck, $CH_2Cl_2$-MeOH: 95:5, Rf=0.09.

mp=155° C.

$^1$H NMR (DMSO-$d_6$) ppm: 1.58-1.73 (m, 2H), 1.87-2.00 (m, 2H), 3.36-3.48 (m, 2H), 3.58 (s, 3H), 3.64-3.75 (m, 2H), 4.89-4.97 (m, 1H), 6.87 (d, 1H, J=9.6 Hz), 7.33 (d, 1H, J=7.6 Hz), 7.56-7.74 (m, 3H), 9.33 (s, 1H).

MS (+ESI) m/z 431 (MH+)

Pharmacological Evaluation

In vitro: Human enzymatic activity of SCD-1 from microsomes of HepG2 cells after treatment with the inhibitor compounds (% inhibition).

HepG2 cells of human hepatocarcinoma (ATCC, HB-8065) are cultured at confluence then trypsinated. The cell residue is solubilized in 10 mM Tris buffer (pH 7.4) sucrose (250 mM) DTT (1 mM) then the cells are lysed by sonication. The microsomes are obtained after centrifuging at 10,000 g for 20 minutes at 4° C. followed by centifrugation of the supernatant at 100,000 g for 60 minutes at 4° C. The residue is solubilized in 10 mM Tris buffer (pH 7.4) sucrose (250 mM) at 4° C. and the microsomal proteins are assayed and stored at −196° C. (liquid nitrogen).

The enzymatic reaction measures the conversion of stearic acid (C18:0 fatty acid) into oleic acid (C18:1 fatty acid) by SCD-1. The enzymatic reaction is initiated by the addition of 125 μg of microsomal fraction of HepG2 cells to tubes (total reaction volume of 500 μl) containing 62 μM stearic acid (45 μM stearic acid and 17 μM [$^{14}$C] stearic acid) in 100 mM phosphate buffer (pH 7.16) with 7.2 mM ATP, 0.54 mM CoA, 6 mM $MgCl_2$, 0.8 mM NADH and the inhibitor compound or vehicle (0.1% DMSO). The tubes are incubated for 20 minutes at 37° C. then the enzymatic reaction is halted by the addition of KOH (12%) and saponification for 30 minutes at 80° C. After acidification (3N HCl), the fatty acids are extracted twice with ethyl ether, evaporated under nitrogen before being solubilized in methanol/dichloromethane (3:1). The reaction product (C18:1) is separated from the reaction substrate (C18:0) by HPLC (Perkin Elmer, C18 reverse phase column) coupled with an in-line radioactivity detector (FlowOne). Enzymatic activity is measured in picomoles of stearic acid converted to oleic acid per minute and per mg of protein. For each inhibitor compound, an $IC_{50}$ value is determined, compared with the reference enzymatic activity (vehicle 0.1% DMSO). Sterculic acid is the reference inhibitor compound (Gomez F. E., Bauman D. E., Ntambi J. M., Fox B. G. Effects of sterculic acid on stearoyl-CoA desaturase in differentiating 313-L1 adipocytes. *Biochem Biophys Res Commun.* 300 316-326 (2003).

TABLE 10

Human enzymatic activity of SCD-1.

| Examples | HSCD-1 (HEPG2) $IC_{50}$ μM |
|---|---|
| Sterculic acid | 0.3 |
| 1 | 0.1-1 |
| 2 | 0.03-0.1 |
| 3 | 0.1-1 |
| 4 | 0.01-0.1 |
| 5 | 0.03-0.1 |
| 6 | 0.003 |
| 7 | 0.1-1 |
| 8 | 0.1 |
| 9 | 0.1-1 |
| 10 | 0.3-1 |
| 11 | 0.1-0.3 |
| 12 | 0.03-0.1 |
| 14 | 0.1-1 |
| 16 | 0.03-0.1 |
| 18 | 3-10 |
| 20 | ~10 |
| 24 | 1-3 |
| 25 | 1-10 |
| 27 | 3-10 |
| 31 | ~0.3 |
| 32 | 0.3-1 |
| 34 | 0.03-0.1 |
| 35 | 0.1-1 |
| 36 | 0.3-1 |
| 37 | 0.3 |
| 40 | 0.01-0.1 |
| 41 | 0.01-0.1 |
| 42 | 0.01-0.1 |
| 43 | 0.01-0.1 |
| 44 | 0.1-1 |
| 45 | 0.1-1 |
| 46 | 1 |
| 47 | 0.3-1 |
| 48 | 1-10 |
| 51 | 0.1-1 |
| 52 | 0.03-0.1 |
| 53 | 0.03-0.1 |
| 54 | 0.03-0.1 |
| 55 | 0.1-1 |
| 56 | 0.1-1 |
| 57 | 0.01-0.1 |
| 58 | 0.01-0.1 |
| 59 | ~1 |
| 60 | 0.1-1 |
| 61 | 0.01-0.1 |
| 62 | 0.03 |
| 63 | 0.03 |
| 64 | 0.3-1 |
| 65 | 1 |
| 66 | 0.1-1 |
| 67 | 0.3 |
| 68 | 0.1-1 |
| 69 | 0.1-1 |
| 70 | 0.1-1 |
| 71 | 0.01-0.1 |
| 72 | 0.01 |
| 73 | 0.01-0.1 |
| 74 | 0.01-0.1 |

The results obtained show that the compounds of general formula (I) inhibit the enzymatic activity of the SCD-1 enzyme.

The compounds of general formula (I) can be used as inhibitors of the SCD-1 enzyme.

The invention claimed is:
1. Compounds of general formula (I),

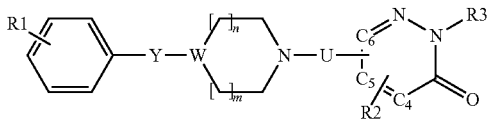

wherein
R₁ represents one or more groups selected from the group consisting of trifluoromethyl, halogen, C₁-C₄ straight and branched alkyl, nitro, trifluoromethoxy, acetyl, when n=m=1,
W represents CH then Y is oxygen or —CH₂N(CH₃)— or —NHCH₂—,
or W represents nitrogen then Y represents C═O,
when n=m=0, W represents CH, then Y is O or —OCH₂—,
when n=1 and m=0, W represents CH, then Y is —OCH₂—,
U represents:
either —(C═O)CH₂O— and can be branched at position (4) or (5) of pyridazinone and R2 represents hydrogen,
or —(C═O)CHR₄NR₅— in which R₄═R₃═H or, independently of each other, can be equal to H or OMe, and if U is branched at position (4) of pyridazinone then R2 is at position (5) and represents H or OMe, and if U is branched at position (5) of pyridazinone then R2 represents H,
or —(C═O)NH— and can be branched at position (4) or (5) or (6) of pyridazinone and R2 represents H,
or —(C═O)(C═O)NH—, —(C═O)CH═CH—, —(C═O)CH₂CH₂—, and can be branched at position (4) of pyridazinone, then R2 represents H,
R₃ represents:
a hydrogen, or
a C₁-C₆ straight or branched alkyl radical, or a C₁-C₃ alkyl radical substituted by groups such as: trifluoromethyl, phenyl, or C₃ alkynyl,
and the addition salts with pharmaceutically acceptable bases and acids, and the different isomers, and their mixtures in any proportion.

2. Compounds of general formula (I) according to claim 1 wherein

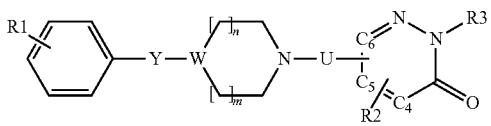

R₁ represents one or more groups selected from the group consisting of trifluoromethyl, halogen, C₁-C₃ straight and branched alkyl, trifluoromethoxy,
when n=m=1,
W represents CH, then Y is oxygen or —CH₂N(CH₃)— or W represents nitrogen, then Y represents C═O,
when n=m=0, W represents CH, then Y is —OCH₂—,
U represents;
either —(C═O)CH₂NH— and if U is branched at position (4) of pyridazinone then R2 is at position (5) and represents H or OMe, and if U is branched at position (5) of pyridazinone then R2 is at position 4 and represents H
or —(C═O)NH— and U can be branched at positions (4), (5) r (6) of pyridazinone, then R2 represents H,
or —(C═O)(C═O)NH—, —(C═O)CH═CH—, —(C═O)CH₂CH₂—, and U is branched at position (4) of pyridazinone, then R2 represents H,
R₃ represents:
a hydrogen, or
a C₁-C₄ straight or branched alkyl radical and more particularly methyl,
and the addition salts with pharmaceutically acceptable bases and acids, and the different isomers, and their mixtures in any proportion.

3. Compounds of general formula (I) according to claim 1, wherein

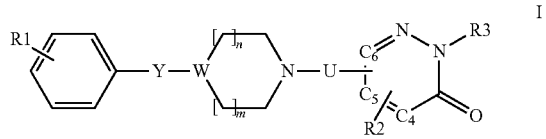

R₁ represents one or more groups selected from the group consisting of trifluoromethyl, and halogen,
when n=m=1, W represents CH, then Y represents oxygen,
U represents:
either —(C═O)CH₂NH— and is branched at position 4 of pyridazinone titer R2 represents H,
or —(C═O)NH— and U can be branched at positions (4), (5) or (6) of pyridazinone, then R2 represents H,
R₃ represents a hydrogen or methyl
and the addition salts with pharmaceutically acceptable bases and acids and the different isomers, and their mixtures in any proportion.

4. Compounds of general formula I according to claim 1, wherein they are chosen from among:
2-Methyl-4-{2-oxo-2-[4-(2-trifluoroethyl-phenoxy)-piperidin-1-yl]-ethylamino}-2H-pyridazin-3-one
4-{2-[4-(5-Fluoro-2-trifluoromethyl-phenoxy)-piperidin-1-yl]-2-oxo-ethylamino}-2-methyl-2H-pyridazin-3-one
4-{2-[4-(3-Fluoro-5-trifluoromethyl-phenoxy)-piperidin-1-yl]-2-oxo-ethylamino}-2-methyl-2H-pyridazin-1-one
4-{2-[4-(2-Chloro-5-trifluoromethyl-phenoxy)-piperidin-1-yl]-2-oxo-ethylamino}-2-methyl-2H-pyridazin-3-one
4-{2-[4-(2-Bromo-4,5-difluoro-phenoxy)-piperidin-1-yl]-2-oxo-ethylamino}-2-methyl-2H-pyridazin-3-one
4-{2-[4-(5-Bromo-2-chloro-phenoxy)-piperidin-1-yl]-2-oxo-ethylamino}-2-methyl-2H-pyridazin-3-one
4-{2-[4-(2-Chloro-phenoxy)-piperidin-1-yl]-2-oxo-ethylamino}-2-methyl-2H-pyridazin-3-one
4-{24-([2-Chloro-fluoro-phenoxy)-piperidin-1-yl]-2-oxo-ethylamino}-2-methyl-2H-pyridazin-3-one
4-{2-[4-(2-Chloro-5-nitro-phenoxy)-piperidin-1-yl]-2-oxo-ethylamino}-2-methyl-2H-pyridazin-3-one
4-{2-[4-(3,4-Dichloro-phenoxy)-piperidin-1-yl]-2-oxo-ethylamino}-2-methyl-2H-pyridazin-3-one
4-{2-[4-(2,4-Dichloro-phenoxy)-piperidin-1-yl]-2-oxo-ethylamino}-2-methyl-2H-pyridazin-3-one
4-{2-[4-(2,5-Dichloro-phenoxy)-piperidin-1-yl]-2-oxo-ethylamino}-2-methyl-2H-pyridazin-3-one 4-{2-[4-(5-Fluoro-2-methyl-phenoxy)-piperidin-1-yl]-2-oxo-ethylamino}-2-methyl-2H-pyridazin-3-one
4-{2-[4-(5-Isopropyl-2-methyl-phenoxy)-piperidin-1-yl]-2-oxo-ethylamino}-2-methyl-2H-pyridazin-3-one
4-({2-[4-(2-Chloro-phenoxy)-piperidin-yl]-2-oxo-ethyl}-methyl-amino)-2-methyl-2H-pyridazin-3-one
5-{2-[4-(2-Chloro-5-fluoro-phenoxy)-piperidin-1-yl]-2-oxo-ethylamino}-2-methyl-2H-pyridazin-3-one
5-{2-[4-(2-Chloro-5-trifluoromethyl-phenoxy)-piperidin-1-yl]-2-oxo-ethoxy}-2-methyl-2H-pyridazin-3-one
5-{2-[4-(2,5-Dichloro-phenoxy)-piperidin-1-yl]-2-oxo-ethoxy}-2-methyl-2H-pyridazin-3-one
2-Methyl-4-{2-oxo-2-[3-(2-trifluoromethyl-phenoxy)-azetidin-1-yl]-ethylamino}-2H-pyridazin-3-one
2-Methyl-4-(2-oxo-2-{4-[(2-trifluoromethyl-phenylamino)-methyl]-piperidin-1-yl}-ethylamino)-2H-pyridazin-3-one
4-(2-{4-[(2-Chloro-5-trifluoromethyl-phenylamino)-methyl]-piperidin-1-yl}-2-oxo-ethylamino)-2-methyl-2H-pyridazin-3-one
4-{2-[3-(2-Chloro-5-trifluoromethyl-phenoxymethyl)-pyrrolidin-1-yl]-2-oxo-ethylamino)-2-methyl-2H-pyridazin-3-one
2-[4-(2-Chloro-5-trifluoromethyl-phenoxy)-piperidin-1-yl]-N-(2-methyl-3-oxo-2,3-dihydro-pyridazin-4-yl)-2-oxo-acetamide
4-{(E)-3-[4-(2-Chloro-5-trifluoromethyl-phenoxy)-piperidin-1-yl]-3-oxo-propenyl}-2-methyl-2H-pyridazin-3-one
4-{3-[4-(2-Chloro-5-trifluoromethyl-phenoxy)-piperidin-1-yl]-3-oxo-propyl}-2-methyl-2H-pyridazin-3-one
5-{2-[4-(2,4-Dichloro-phenoxy)-piperidin-1-yl]-2-oxo-ethoxy}-2-methyl-2H-pyridazin-3-one
2-Methyl-4-{2-oxo-2-[3-(2-trifluoromethyl-phenoxy)-azetidin-1-yl]-ethylamino}-2H-pyridazin-3-one
4-(2-{4-[(3,4-Dichloro-benzyl)-methyl-amino]-piperidin-1-yl}-2-oxo-ethylamino)-2-methyl-2H-pyridazin-3-one
4-{2-[4-(5-Fluoro-2-trifluoromethyl-benzoyl)-piperazin-1-yl]-2-oxo-ethylamino}-2-methyl-2H-pyridazin-3-one
2-Methyl-4-{2-oxo-2-[4-(2-trifluoromethyl-benzoyl)-piperazin-1-yl]-ethylamino}-2H-pyridazin-3-one
2-Methyl-4-(2-oxo-2-{4-[(2-trifluoromethyl-phenylamino)-methyl]-piperidin-1-yl}-ethylamino)-2H-pyridazin-3-one
4-(2-{4-[(2-Chloro-5-trifluoromethyl-phenylamino)-methyl]-piperidin-1-yl}-2-oxo-ethylamino)-2-methyl-2H-pyridazin-3-one
4-{2-[3-(2-Chloro-5-trifluoromethyl-phenoxymethyl)-azetidin-1-yl]-2-oxo-ethylamino}-2-methyl-2H-pyridazin-3-one
4-{2-[3-(2-Chloro-5-trifluoromethyl-phenoxymethyl)-pyrrolidin-1-yl]-2-oxo-ethylamino}-2-methyl-2H-pyridazin-3-one
2-[4-(2-Chloro-5-trifluoromethyl-phenoxy)-piperidin-1-yl]-N-(2-methyl-3-oxo-2,3-dihydro-pyridazin-4-yl)-2-oxo-acetamide
4-{(E)-3-[4-(2-Chloro-5-trifluoromethyl-phenoxy)-piperidin-1-yl]-3-oxo-propenyl}-2-methyl-2H-pyridazin-3-one
4-{3-[4-(2-Chloro-5-trifluoromethyl-phenoxy)-piperidin-1-yl]-3-oxo-propyl}-2-methyl-2H-pyridazin-3-one
4-{(R)-2-[4-(2-Chloro-5-trifluoromethyl-phenoxy)-piperidin-1-yl]-1-methyl-2-oxo-ethylamino}-2-methyl-2H-pyridazin-3-one
4-{(S)-2-[4-(2-Chloro-5-trifluoromethyl-phenoxy)-piperidin-1-yl]-1-methyl-2-oxo-ethylamino}-2-methyl-2H-pyridazin-3-one
4-{2-[4-(2-Chloro-5-trifluoromethyl-phenoxy)-piperidin-1-yl]-2-oxo-ethylamino)-2H-pyridazin-3-one
4-(2-[4-(2,5-dichloro-phenoxy)-piperidin-1-yl]-2-oxo-ethylamino}-2H-pyridazin-3-one
4-{2-[4-(5-Bromo-2-Chloro-phenoxy)-piperidin-1-yl]-2-oxo-ethylamino}-2H-pyridazin-3-one
4-{2-[4-(2-Bromo-4,5-di fluoro-phenoxy)-piperidin-1-yl]-2-oxo-ethylamino}-2H-pyridazin-3-one
4-{2-[4-(3-trifluoromethyl-phenoxy)-piperidin-1-yl]-2-oxo-ethylamino}-2H-pyridazin-3-one
4-{2-[4-(2-Chloro-5-trifluoromethyl-phenoxy)-piperidin-1-yl]-2-oxo-ethylamino}-2-(4,4,4-trifluoro-butyl)-2-1-pyridazin-3-one
2-But-2-ynyl-4-{2-[4-(2-chloro-5-trifluoromethyl-phenoxy)-piperidin-11-yl]-2-oxo-ethylamino}-2H-pyridazin-3-one
4-{2-[4-(2-Chloro-5-trifluoromethyl-phenoxy)-piperidin-1-yl]-2-oxo-ethylamino}-2-(4-methyl-pentyl)-2H-pyridazin-3-one
2-Benzyl-4-{2-oxo-2-[4-(2 trifluoromethyl-phenoxy)-piperidin-1-yl]-ethylamino}-2H-pyridazin-3-one
2-Isopropyl-4-{2-oxo-2-[4-(2-trifluoromethyl-phenoxy)-piperidin-1-yl]-ethylamino}-2H-pyridazin-3-one
2-Butyl-4-{2-[4-(2-chloro-phenoxy)-piperidin-1-yl]-2-oxo-ethylamino}-2H-pyridazin-3-one
4-{2-[4-(2-Chloro-5-trifluoromethyl-phenoxy)-piperidin-1-yl]-2-oxo-ethylamino}-5-methoxy-2-methyl-2H-pyridazin-3-one
4-(2-Chloro-5-trifluoromethyl-phenoxy)-piperidine-1-carboxylic acid (2-methyl-3-oxo-2,3-dihydro-pyridazin-4-yl)-amide
4-(2-Chloro-5-fluoro-phenoxy)-piperidine-1-carboxylic acid (2-methyl-3-oxo-2,3-dihydro-pyridazin-4-yl)-amide
4-(2-fluoro-5-trifluoromethyl-phenoxy)-piperidine-1-carboxylic acid (2-methyl-3-oxo-2,3-dihydro-pyridazin-4-yl)-amide
4-(2,5-dimethyl-phenoxy)-piperidine-1-carboxylic acid (2-methyl-3-oxo-2,3-dihydro-pyridazin-4-yl)-amide
4-(2-chloro-5-methyl-phenoxy)-piperidine-1-carboxylic acid (2-methyl-3-oxo-2,3-dihydro-pyridazin-4-yl)-amide
4-(2-methyl-5-isopropyl-phenoxy)-piperidine-1-carboxylic acid (2-methyl-3-oxo-2,3-dihydro-pyridazin-4-yl)-amide
4-(5-trifluoromethyl-phenoxy)-piperidine-1-carboxylic acid (2-methyl-3-oxo-2,3-dihydro-pyridazin-4-yl)-amide
4-(2-methyl-phenoxy)-piperidine-1-carboxylic acid (2-methyl-3-oxo-2,3-dihydro-pyridazin-4-yl)-amide
4-(4-fluoro-5-trifluoromethyl-phenoxy)-piperidine-1-carboxylic acid (2-methyl-3-oxo-2,3-dihydro-pyridazin-4-yl)-amide
4-(S-fluoro-2-trifluoromethyl-phenoxy)-piperidine-1-carboxylic acid (2-methyl-3-oxo-2,3-dihydro-pyridazin-4-yl)-amide
4-(2,5-dichloro-phenoxy)-piperidine-1-carboxylic acid (2-methyl-3-oxo-2,3-dihydro-pyridazin-4-yl)-amide
4-(2-chloro-5-bromo-phenoxy)-piperidine-1-carboxylic acid (2-methyl-3-oxo-2,3-dihydro-pyridazin-4-yl)-amide
4-(2-chloro-phenoxy)-piperidine-1-carboxylic acid (2-methyl-3-oxo-2,3-dihydro-pyridazin-4-yl)-amide 4-(3,4-dichloro-phenoxy)-piperidine-1-carboxylic acid (2-methyl-3-oxo-2,3-dihydro-pyridazin-4-yl)-amide 4-(2,4-dichloro-phenoxy)-piperidine-1-carboxylic acid (2-methyl-3-oxo-2,3-dihydro-pyridazin-4-yl)-amide 4-(3-fluoro-5-trifluoromethyl-phenoxy)-piperidine-1-carboxylic acid (2-methyl-3-oxo-2,3-dihydro-pyridazin-4-yl)-amide 4-(5-fluoro-2-methyl-phenoxy)-piperidine-1-carboxylic acid (2-methyl-3-oxo-2,3-dihydro-pyridazin-4-yl)-amide 4-(2,5-difluoro-phenoxy)-piperidine-1-carboxylic acid (2-methyl-3-oxo-2,3-dihydro-pyridazin-4-yl)-amide 4-(2,4,5-trichloro-phenoxy)-piperidine-1-carboxylic acid (2-methyl-3-oxo-2,3-dihydro-pyridazin-4-yl)-amide 4-(2-bromo-4,5-difluoro-phenoxy)-piperidine-1-carboxylic acid (2-methyl-3-oxo-2,3-dihydro-pyridazin-4-yl)-amide 4-(2-Chloro-5-trifluoromethyl-phenoxy)-piperidine-1-carboxylic acid (3-oxo-2,3-dihydro-pyridazin-4-yl)-amide 4-(2-Chloro-5-trifluoromethyl-phenoxy)-piperidine-1-carboxylic acid (1-methyl-6-oxo-1,6-dihydro-pyridazin-4-yl)-amide 4-(2-Cloro-5-trifluoromethyl-phenoxy)-piperidine-1-carboxylic acid (1-methyl-6-oxo-1,6-dihydro-pyridazin-3-yl)-amide.

5. Compounds of general formula (I) according to claim 1, wherein halogen is F, Cl, or Br.

6. Pharmaceutical composition wherein, as active ingredient, it contains a compound of general formula I such as defined in claim 1.

7. Pharmaceutical composition wherein it contains a compound of general formula I such as defined in claim 1 combined with any suitable excipient.

8. Pharmaceutical composition according to claim 6, combined with an anti-diabetic selected from the group consisting of biguanides, forms of sulfonylureas, meglitinides, PPAR modulators, inhibitors of alpha-glucosidase, inhibitors of DPP-4, amylin analogues, analogues of glucagon-like peptide-1, inhibitors of SGLT2 and inhibitors of 11β-HSD1.

9. Pharmaceutical composition according to claim 6, combined with an anti-obesity agent selected from the group consisting of orlistat or sibutramine.

10. Pharmaceutical composition according to claim 6, further comprising an anti-cancer agent selected from the group consisting of derivatives of platinum, taxanes, vincas, 5-FU.

11. Method to prepare chemical compounds of general formula I according to claim 1, when U=—(C=O)CHR$_4$NR$_5$—, which is branched at positions (4) or (5) of pyridazinone and R$_2$=H, which comprises condensing a compound of general formula II

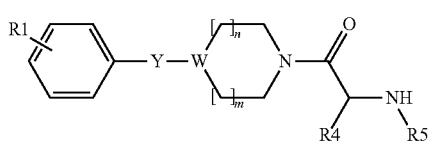

in which R$_1$ represents one or more groups selected from the group consisting of trifluoromethyl, Cl, F, C$_1$-C$_4$ straight or branched alkyl, trifluoromethoxy, and acetyl, and R$_4$, R$_5$, m, n, Y, W are as defined in general formula I of claim 1, with a compound of general formula III

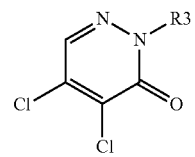

in which R$_3$ is a C$_1$-C$_6$ straight or branched alkyl radical, or C$_1$-C$_3$ alkyl radical substituted with trifluoromethyl or phenyl, in the presence of a catalyst, a phosphine and a base in a solvent, to obtain a compound of general formula (IV);

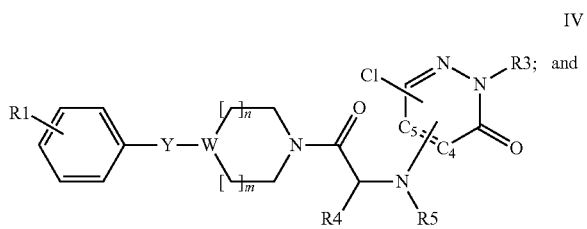

dehalogenating the compound of general formula IV in the presence of palladium on carbon under hydrogen in a solvent.

12. Method to prepare chemical compounds of general formula I according to claim 1 when U=—(C=O)CHR$_4$NR$_5$—, —(C=O)CH$_2$O—, —(C=O)(C=O)NH—, —(C=O)CH=CH—, —(C=O)(CH$_2$)$_2$— in which the substitution positions of pyridazinone are as defined in general formula I of claim 1 which comprises condensing a compound of general VI

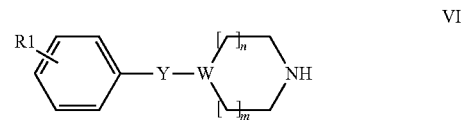

in which R$_1$, m, n, Y, W are as defined in general formula I of claim 1, with a compound of general formulas VII, IX, XIII, or XV in which R$_2$, R$_4$, and R$_5$ are as defined in general formula I of claim 1, and R$_3$ represents a hydrogen, C$_1$-C$_6$ straight or branched alkyl radical, or a C$_1$-C$_3$ alkyl radical substituted by trifluoromethyl, phenyl, or a compound of general formula XI in which R$_3$ is such as defined in general formula I, under conditions suitable for peptide coupling with hydroxybenzotriazole and EDCI in the presence of a base and in a solvent such as comprising dichloromethane, wherein the compounds of general formulas VII, IX, XI, XIII, and XV are

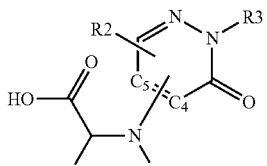

VII

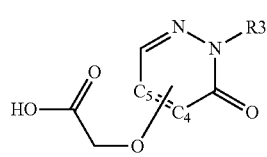

IX

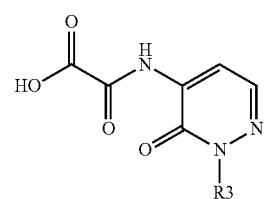

XI

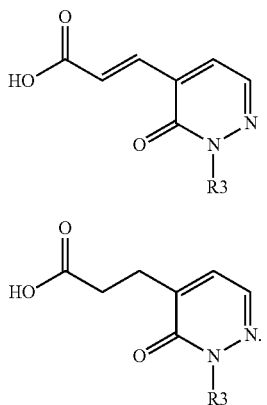

XIII

XV

13. Method to prepare chemical compounds of general formula I according to claim 1 when U=—(C=O)CHR₄NR₅— or —(C=O)CH₂O— (branched at positions (4) or (5) of pyridazinone) and R₂=H, which comprises condensing a compound of general formula XVII or XVIII

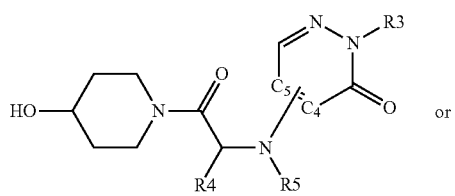

XVII or

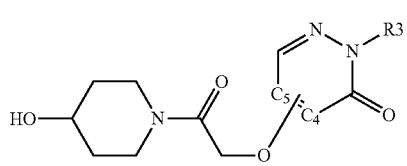

XVIII in which R₃ represents a C₁-C₆ straight or branched alkyl radical, or a C₁-C₃ alkyl radical substituted by trifluoromethyl or phenyl and R₄ and R₅ are such as defined in general formula I of claim 1, with a phenol of general formula XIX:

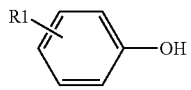

XIX in which R₁ is as defined in general formula I of claim 1, under conditions of a Mitsunobu coupling reaction in the presence of triphenylphosphine and diisopropylazodicarboxylate in THF to arrive at compounds XX and XXI respectively, wherein the compounds XX and XXI are:

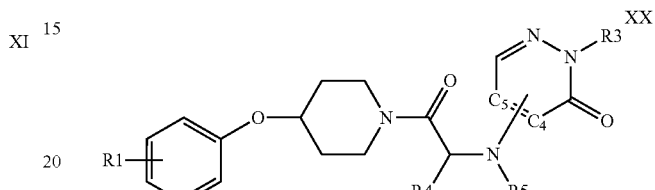

XX

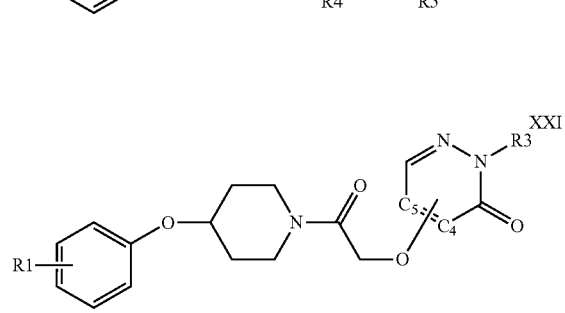

XXI

In which R₁, R₃ and R₄ as are as defined in general formula I of claim 1.

14. Method to prepare chemical compounds of general formula I according to claim 1 when U=—(C=O)CHR₄NR₅— is branched at position (4) of pyridazinone and R₂=H, which comprises condensing a compound of general formula II in which R₁, R₄, R₅, n, m, Y, W are as defined in general formula I of claim 1,

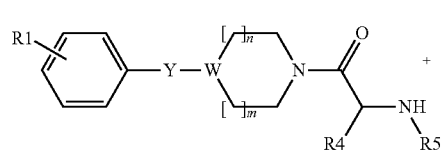

II with a compound of general formula XXII

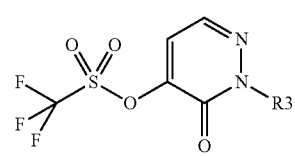

XXII in which R₃ is as defined in general formula I of claim 1, under in the presence of acetonitrile and triethylamine to arrive at compounds XXIII

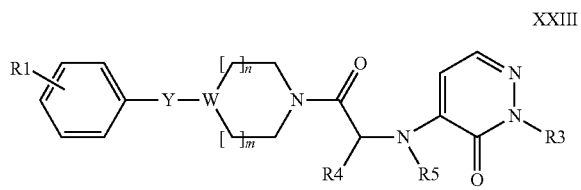

in which $R_1$, $R_3$, $R_4$, and $R_5$, are as defined in general formula I of claim 1.

15. Method to prepare chemical compounds of general formula I according to claim 1 when U=—(C=O)CHR$_4$NR$_5$— is branched at position (4) of pyridazinone and R$_2$=H, which comprises condensing a compound of general formula II, in which R$_1$, R$_4$, R$_5$, n, m, Y, W are as defined in general formula I of claim 1,

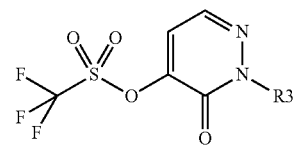

with a compound of general formula XXII

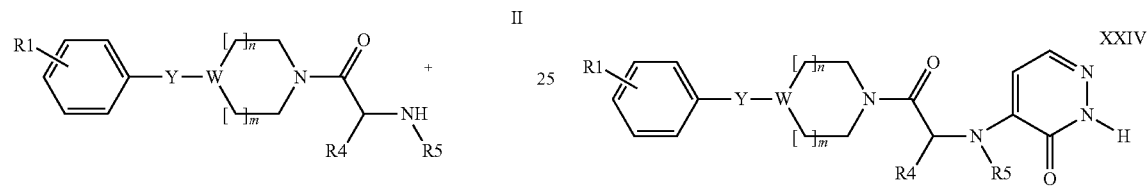

in which R$_3$ is a protecting group in the presence of acetonitrile and triethylamine to arrive at compounds XXIII

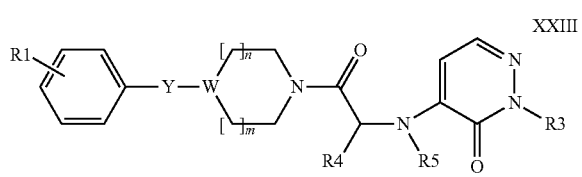

in which $R_1$, $R_3$, $R_4$, $R_5$, are as defined in general formula I of claim 1;

deprotecting the compound of formula XXIII with trifluoroacetic acid in dichloromethane (when R$_3$=3,4 dimethoxybenzyl) or in the presence of palladium on carbon in THF under hydrogen (when R$_3$=benzyloxymethyl) to arrive at compounds XXIV in which Y, W, $R_1$, $R_4$, and $R_5$ are as defined in general formula I of claim 1.

16. Method to prepare chemical compounds of general formula I according to claim 1 when U=—(C=O)CHR$_4$NR$_5$— is branched at position (4) of pyridazinone and R$_2$=H, which comprises reacting a compound of general formula XXIV, in which R$_1$, R$_4$, R$_5$, n, m, Y, W are as defined in general formula I of claim 1, with an alkylating agent R$_3$X in which X represents a halogen and R$_3$ represents a C$_1$-C$_6$ straight or branched alkyl radical, or a C$_1$-C$_3$ alkyl radical substituted by trifluoromethyl, phenyl, or C$_3$ alkynyl, in the presence of DMF and K$_2$CO$_3$ to arrive at compounds XXV in which Y, W, $R_1$, $R_4$ and R are as defined in general formula I of claim 1.

17. Method to prepare chemical compounds of general formula I according to claim 1 when U=—(C=O)NH— (branched at position 4 or 5 or 6 of pyridazinone) and R$_2$ represents which comprises condensing a compound of general formula VI, in which R$_1$, m, n, W are as defined in general formula I of claim 1,

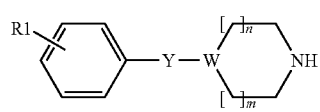

with a compound of general formula XXVI in which R$_3$ is as defined in general formula I of claim 1,

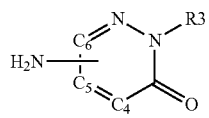
XXVI
in the presence of 4-nitrophenylchloroformate and triethylamine in THF to arrive at compounds XXVII
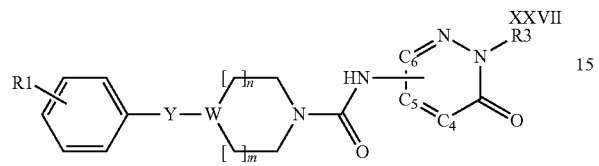
XXVII
in which Y, W, $R_1$, $R_4$, and $R_5$, are as defined in general formula I of claim 1.
18. A method of inhibiting SCD1 enzyme which comprise treating said enzyme with an effective amount of a compound of general formula (I) according to claim 1.
* * * * *

UNITED STATES PATENT AND TRADEMARK OFFICE
CERTIFICATE OF CORRECTION

PATENT NO.       : 8,946,225 B2
APPLICATION NO.  : 13/388884
DATED            : February 3, 2015
INVENTOR(S)      : Elisabeth Dupont-Passelaigue et al.

It is certified that error appears in the above-identified patent and that said Letters Patent is hereby corrected as shown below:

IN THE CLAIMS:

In claim 4, at column 80, lines 58-59, change "4-{24-([2-Chloro-fluoro-phenoxy)-piperidin-1-yl]-2-oxo-ethylamino}-2-methyl-2H-pyridazin-3-one" to --4-{2-[4-(2-Chloro-5-fluoro-phenoxy)-piperidin-1-yl]-2-oxo-ethylamino}-2-methyl-2H-pyridazin-3-one--.

In claim 4, at column 82, lines 58-59, change "4-(S-fluoro-2-trifluoromethyl-phenoxy)-piperidine-1-carboxylic acid (2-methyl-3-oxo-2,3-dihydro-pyridazin-4-yl)-amide" to --4-(5-fluoro-2-trifluoromethyl-phenoxy)-piperidine-1-carboxylic acid (2-methyl-3-oxo-2,3-dihydro-pyridazin-4-yl)-amide--.

In claim 12, at column 84, line 64, change "in a solvent such as comprising" to --in a solvent comprising--.

In claim 17, at column 88, lines 52-53, change "and $R_2$ represents which comprises" to --and $R_2$ represents H which comprises--.

Signed and Sealed this
Twenty-ninth Day of March, 2016

Michelle K. Lee
*Director of the United States Patent and Trademark Office*